(12) United States Patent
Becker-Pelster et al.

(10) Patent No.: US 9,624,198 B2
(45) Date of Patent: Apr. 18, 2017

(54) SUBSTITUTED PIPERIDINYLTETRAHYDROQUINOLINES

(71) Applicant: Bayer Pharma Aktiengesellschaft, Berlin (DE)

(72) Inventors: Eva Maria Becker-Pelster, Wuppertal (DE); Philipp Buchgraber, Berlin (DE); Anja Buchmüller, Essen (DE); Karen Engel, Roßdorf (DE); Volker Geiss, Ratingen (DE); Andreas Göller, Wuppertal (DE); Herbert Himmel, Essen (DE); Raimund Kast, Wuppertal (DE); Andreas Knorr, Erkrath (DE); Dieter Lang, Velbert (DE); Gorden Redlich, Bochum (DE); Carsten Schmeck, Mülheim (DE); Hanna Tinel, Wuppertal (DE); Frank Wunder, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/106,283

(22) PCT Filed: Dec. 16, 2014

(86) PCT No.: PCT/EP2014/077865
§ 371 (c)(1),
(2) Date: Jun. 18, 2016

(87) PCT Pub. No.: WO2015/091417
PCT Pub. Date: Jun. 25, 2015

(65) Prior Publication Data
US 2016/0304491 A1 Oct. 20, 2016

(30) Foreign Application Priority Data

Dec. 19, 2013 (EP) .................................. 13198388
Nov. 12, 2014 (EP) .................................. 14192878

(51) Int. Cl.
| | | |
|---|---|---|
| *C07D 401/14* | (2006.01) | |
| *A61K 31/4725* | (2006.01) | |
| *C07D 413/14* | (2006.01) | |
| *C07D 491/107* | (2006.01) | |
| *C07D 495/10* | (2006.01) | |
| *A61K 31/506* | (2006.01) | |
| *A61K 31/5377* | (2006.01) | |
| *A61K 31/541* | (2006.01) | |
| *A61K 45/06* | (2006.01) | |

(52) U.S. Cl.
CPC ........ *C07D 401/14* (2013.01); *A61K 31/4725* (2013.01); *A61K 31/506* (2013.01); *A61K 31/5377* (2013.01); *A61K 31/541* (2013.01); *A61K 45/06* (2013.01); *C07D 413/14* (2013.01); *C07D 491/107* (2013.01); *C07D 495/10* (2013.01)

(58) Field of Classification Search
CPC ............... C07D 401/14; C07D 413/14; C07D 491/107; C07D 495/10; A61K 31/4725; A61K 31/506; A61K 31/5377; A61K 31/541; A61K 45/06
USPC .................................................... 514/210.21
See application file for complete search history.

(56) References Cited

U.S. PATENT DOCUMENTS

| | | |
|---|---|---|
| 6,444,681 B1 | 9/2002 | Flavahan et al. |
| 6,495,555 B1 | 12/2002 | Kennis et al. |
| 2004/0010008 A1 | 1/2004 | Palani et al. |
| 2004/0092551 A1* | 5/2004 | Palani ............. C07D 401/14 514/316 |
| 2004/0092745 A1 | 5/2004 | Palani et al. |
| 2005/0182095 A1 | 8/2005 | Ting et al. |
| 2006/0025441 A1 | 2/2006 | Miller et al. |
| 2006/0223792 A1 | 10/2006 | Butler et al. |
| 2008/0214575 A1 | 9/2008 | Palani et al. |
| 2011/0262352 A1 | 10/2011 | Din Belle et al. |
| 2014/0023614 A1 | 1/2014 | Barawkar et al. |

FOREIGN PATENT DOCUMENTS

| | | |
|---|---|---|
| CA | 2371587 | 9/2005 |
| WO | 94/22826 | 10/1994 |
| WO | 97/26265 | 7/1997 |
| WO | 99/03861 | 1/1999 |
| WO | 00/06568 | 2/2000 |
| WO | 00/06569 | 2/2000 |
| WO | 00/66559 | 9/2000 |
| WO | 00/66559 | 11/2000 |
| WO | 01/19355 | 3/2001 |
| WO | 01/19776 | 3/2001 |

(Continued)

OTHER PUBLICATIONS

Chotani, et al., "Distinct cAMP signaling pathways differentially regulate alpha2C adrenenoxceptor expression: role in serum induction in human arteriolar smooth muscle cells", Am J Physiol Heart Circ Physiol 288, 2005, pp. H69-H76.

(Continued)

*Primary Examiner* — Yevegeny Valenrod
(74) *Attorney, Agent, or Firm* — Aseem Mehta

(57) ABSTRACT

The present application relates to novel substituted piperidinyltetrahydroquinolines, to processes for their preparation, to their use for the treatment and/or prevention of diseases and to their use for preparing medicaments for the treatment and/or prevention of diseases, in particular for the treatment and/or prevention of diabetic microangiopathies, diabetic ulcers on the extremities, in particular for promoting wound healing of diabetic foot ulcers, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

20 Claims, 3 Drawing Sheets

(56) References Cited

FOREIGN PATENT DOCUMENTS

| WO | 01/19780 | 3/2001 |
|---|---|---|
| WO | 01/19778 | 3/2002 |
| WO | 02/42301 | 5/2002 |
| WO | 02/070462 | 9/2002 |
| WO | 02/070510 | 9/2002 |
| WO | 02/081449 | 10/2002 |
| WO | 03/020716 | 3/2003 |
| WO | 03/095451 | 11/2003 |
| WO | 2004/067513 | 8/2004 |
| WO | 2005/042517 | 5/2005 |
| WO | 2005/077369 | 8/2005 |
| WO | 2010/058060 | 5/2010 |
| WO | 2012/127506 | 9/2012 |

OTHER PUBLICATIONS

Chotani, et al., "Silent alpha2C adrenergic receptors enable cold-induced vasoconstriction in cutaneous arteries", Am J Heart Circ Physiol 278, 2000, pp. H1075-H1083.

Cryan, et al., "Assessing antidepressant activity in rodents: recent developments and future needs", Trends Pharmacol. Sci. 23, 2002, pp. 238-245.

De Vry, et al., "Comparison of hypericum extracts with imipramine and fluoxetine in animal models of depression and alcoholism", Eur. Neuropsychopharmacology 9, 1999, pp. 461-468.

European Patent Office, Written Opinion (with English translation) for International Patent Application No. PCT/EP2014/077865, Jun. 25, 2015, 14 pages.

European Patent Office, International Search Report (with English translation) for International Patent Application No. PCT/EP2014/077865, Mar. 26, 2015, 7 pages.

Gyires, et al., "alpha2-Adrenoceptor subtypes-mediated physiological, pharmacological actions", Neurochemistry International 55, 2009, pp. 447-453.

International Bureau of WIPO, International Preliminary Report on Patentability for International Patent Application No. PCT/EP2014/077865, Jun. 21, 2016, 7 pages.

Kanagy, "alpha2-Adrenergic receptor signalling in hypertension", Clinical Science 109, 2005, pp. 431-437.

Keenan, et al., "alpha2-Adrenergic receptors in platelets from patients with Raynaud's syndrome", Surgery, V94(2), 1983, pp. 204-209.

Porsolt, et al., "Behavioural despair in rats: a new model sensitive to antidepressant treatments", European Journal of Pharmacology, 47, 1978, pp. 379-391.

Porsolt, et al., "Rodent models of depression: forced swimming and tail suspension behavioral despair tests in rats and mice", Current Protocols in Neuroscience, Chapter 8:Unit 8.10A, 2001, pp. 1-10.

Tan, et al., "The alpha2-Adrenergic Receptors", The Receptors: Adrenergic Receptors in the 21st Century, 2005, pp. 241-265.

Vogelsberger, "Neue Tiermodelle für die Indikation Claudicatio Intermittens", [Novel animal models for the indication intermittent claudication] (pocket book), publisher: VVB Laufersweiler Verlag ISBN-10: 383595007X, ISBN-13: 978-3835950078, Mar. 2006, 29 pages.

Witte, et al., "Experimental heart failure in rats: effects on cardiovascular circadian rhythms and on myocardial β-adrenergic signaling", Cardiovasc. Res. 47(2), 2000, pp. 203-405.

Wuitschik, et al., "Spirocyclic Oxetanes: Synthesis and Properties", Angew. Chem. Int. Ed., 47, 2008, pp. 4512-4515.

Shirley et al., "Some Observations Pertaining to the Mechanism of Metalation of Aromatic Substrates with Alkyllithium Reagents," Journal of Organometallic Chemistry, 69, pp. 327-344, 1974.

Bujalska et al., "$\alpha_1$- and $\alpha_2$- Adrenoreceptor antagonists in streptozotocin- and vincristine-induced hyperalgesia," Pharmacological Reports, vol. 60, No. 4, Jul. 1, 2008, pp. 499-507, Institute of Pharmacology, Polish Academy of Sciences.

European Patent Office, PCT International Search Report and Written Opinion received for PCT Application No. PCT/EP2014/077868 (Translations), Jun. 25, 2015, 31 pages.

PCT International Search Report and Written Opinion received in PCT Application No. PCT/EP2014/077863 (Translations), Jun. 25, 2015, 32 pages.

European Patent Office, International Search Report (with English translation) for International Patent Application No. PCT/EP2014/077862, Jun. 26, 2015, 8 pages.

European Patent Office, Written Opinion (with English translation) for International Patent Application No. PCT/EP2014/077862, Jun. 30, 2015, 25 pages.

International Bureau of WIPO, International Preliminary Report on Patentability for International Patent Application No. PCT/EP2014/077862, Jun. 21, 2016, 13 pages.

International Bureau of WIPO, International Preliminary Report on Patentability for International Patent Application No. PCT/EP2014/077863, Jun. 21, 2016, 10 pages.

International Bureau of WIPO, International Preliminary Report on Patentability for International Patent Application No. PCT/EP2014/077868, Jun. 21, 2016, 10 pages.

USPTO, Notice of Allowance fo U.S. Appl. No. 15/106,286, Sep. 14, 2016, 26 pages.

USPTO, Notice of Allowance for U.S. Appl. No. 15/106,286, Dec. 13, 2016, 7 pages.

\* cited by examiner

SUBSTITUTED PIPERIDINYLTETRAHYDROQUINOLINES

CROSS-REFERENCE TO RELATED APPLICATIONS

This application is a U.S. national phase application of International Patent Application No. PCT/EP2014/077865, filed Dec. 16, 2014 and titled SUBSTITUTED PIPERIDI-NYL-TETRAHYDROQUINOLINES, which claims priority to both European Patent Application No. 13198388.4, filed Dec. 19, 2013 and titled SUBSTITUTED PIPERIDI-NYL-TETRAHYDROQUINOLINES, and European Patent Application No. 14192878.8, filed Nov. 12, 2014 and titled SUBSTITUTED PIPERIDINYL-TETRAHYDROQUINO-LINES, the contents of all of which are incorporated herein by reference in their entirety.

The invention relates to novel substituted piperidinyltetrahydroquinolines, to processes for their preparation, to their use in a method for the treatment and/or prophylaxis of diseases and to their use for preparing medicaments for the treatment and/or prophylaxis of diseases, in particular of cardiovascular disorders, diabetic microangiopathies, diabetic ulcers on the extremities, in particular for promoting wound healing of diabetic foot ulcers, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

Adrenoreceptor cc receptors ($\alpha_2$-ARs) belong to the family of the G-protein-coupled receptors. They bind to the pertussis toxin-sensitive inhibitory G protein $G_i$ and $G_0$ and reduce adenylate cyclase activity. They are involved in the mediation of diverse physiological effects in various tissues following stimulation by endogenous katecholamines (adrenaline, noradrenaline) which are either released by synapses or reach their site of action via the blood. $\alpha_2$-AR play an important physiological role, mainly for the cardiovascular system, but also in the central nervous system. Biochemical, physiological and pharmacological studies have shown that, in addition to various $\alpha_1$-AR subtypes, there are three $\alpha_2$-AR subtypes ($\alpha_{2A}$, $\alpha_{2B}$ and $\alpha_{2C}$) in many target cells and tissues of cardiovascular relevance, which makes them attractive target proteins for therapeutic interventions. However, the elucidation of the precise physiological task of the receptor subtypes remains difficult because of a lack of highly selective ligands and/or antagonists of the respective $\alpha_2$-AR (Gyires et al., $\alpha_2$-Adrenoceptor subtypes-mediated physiological, pharmacological actions, Neurochemistry International 55, 447-453, 2009; Tan and Limbird, The $\alpha_2$-Adrenergic Receptors: Adrenergic Receptors in the 21st Century/Receptors, 2005, 241-265).

Cardiovascular changes such as, for example, the regulation of the contractility of the heart are regulated, firstly, by the central modulation of the sympathetic efferent nerves. Furthermore, the sympathetic efferent system also regulates direct effects on smooth muscle cells and the endothelial cells of the vessels. Thus, the sympathetic system is involved in the regulation of the output performance of the heart, but also in the control of local perfusion of various vascular beds. This is also controlled via $\alpha_2$-ARs involved in the regulation of the peripheral resistance. Thus, blood vessels are innervated by sympathetic nerve fibres which are located in the adventitia and whose endings are provided with varicosities for the release of noradrenalin. Released noradrenalin modulates, via the $\alpha_2$-AR in endothelial cells and smooth muscle cells, the respective local vascular tone.

In addition to the effects on the sympathetic efferent nerves, the peripheral cardiovascular function are also regulated by pre- and postsynaptic $\alpha_2$-AR. Smooth muscle cells and endothelial cells express different $\alpha_2$-AR subtypes. The activation of $\alpha_{2A}$, $\alpha_{2B}$ and $\alpha_{2C}$ receptors on smooth muscle cells leads to contraction with resulting vasoconstriction (Kanagy, Clinical Science 109:431-437, 2005). However, the distribution of the respective receptor subtypes varies in the different vascular beds, between the species and between different vessel sizes. Thus, $\alpha_{2A}$-AR appear to be expressed virtually exclusively in large arteries, whereas $\alpha_{2B}$-AR contribute more to the vascular tone in small arteries and veins. AR$\alpha_{2B}$ appear to play a role in salt-induced hypertension (Gyires et al., $\alpha_2$-Adrenoceptor subtypes-mediated physiological, pharmacological actions, Neurochemistry International 55, 447-453, 2009). The role of AR$\alpha_{2C}$ on haemodynamics is not yet completely understood; however, AR$\alpha_{2C}$ receptors appear to mediate venous vasoconstriction. They are also involved in cold-induced enhancement of adrenoceptor-induced vasoconstriction (Chotani et al., Silent $\alpha_{2C}$ adrenergic receptors enable cold-induced vasoconstriction in cutaneous arteries. Am J Physiol 278:H1075-H1083, 2000; Gyires et al., $\alpha_2$-Adrenoceptor subtypes-mediated physiological, pharmacological actions, Neurochemistry International 55, 447-453, 2009). Cold and other factors (e.g. tissue proteins, estrogen) regulate the functional coupling of AR$\alpha_{2C}$ to intracellular signal pathways (Chotani et al., Distinct cAMP signaling pathways differentially regulate $\alpha_{2C}$ adrenenoxceptor expression: role in serum induction in human arteriolar smooth muscle cells. Am J Physiol Heart Circ Physiol 288: H69-H76, 2005). For this reason, it appears to make sense to investigate selective inhibitors of AR-$\alpha_2$ subtypes for their perfusion-modulating effect on different vascular beds under different pathophysiological conditions.

Under pathophysiological conditions, the adrenergic system may be activated, which can lead, for example, to hypertension, heart failure, increased platelet activation, endothelial dysfunction, atherosclerosis, angina pectoris, myocardial infarction, thromboses, peripheral circulatory disturbances, stroke and sexual dysfunction. Thus, for example, the pathophysiology of Raynaud's syndrome and scleroderma is substantially unclear, but is associated with a changed adrenergic activity. Thus, patients suffering from spastic Raynaud's syndrome show, for example, a significantly elevated expression of AR$\alpha_2$ recptoren on their platelets. This may be connected with the vasospastic attacks observed in these patients (Keenan and Porter, $\alpha_2$-Adrenergic receptors in platelets from patients with Raynaud's syndrome, Surgery, V94(2), 1983).

By virtue of the expected high efficiency and low level of side effects, a possible treatment for such disorders targeting a modulation of the activated adrenergic system in organisms is a promising approach. In particular in diabetics, who frequently have elevated catecholamine levels, peripheral circulatory disturbances (microangiopathies) such as diabetic retinopathy, nephropathy or else pronounced wound healing disorders (diabetic foot ulcers) play a large role. In peripheral occlusive disease, diabetes is one of the most important comorbidities and also plays a crucial role in the progression of the disease (micro- and macroangiopathy). Higher expression of the adrenoreceptor $\alpha_{2C}$ receptors associated with elevated catecholamine levels may be involved in these pathophysiological processes in diabetics.

In 2011 there were 350 million diabetics world-wide (≈6.6% of the population), and this number is expected to double until 2028. Diabetic foot ulcers are the most frequent cause of hospitalisations of diabetics. The risk of a diabetic to develop diabetic foot ulcer in his or her lifetime is 15-25%, 15% of all diabetic foot ulcers lead to amputation. World-wide, 40-70% of all non-traumatic amputations are carried out on diabetics. Risk factors for diabetic foot ulcers are traumata, poor metabolic control, sensory, motoric and autonomous polyneuropathy, inappropriate footwear, infections and peripheral arterial disorders. The treatment of diabetic foot ulcers requires interdisciplinary teams and employs a multifactor approach: weight loss, revascularisation (in the case of peripheral arterial occlusive disease, PAOD), improvements in metabolic control, wound excision, dressings, dalteparin, Regranex (PDGF) and amputation. The treatment costs per diabetic foot ulcer (without amputation) are 7,000-10,000 USD. 33% of all diabetic foot ulcers do not heal within 2 years, and there is a high relapse rate (34% within the first year, 61% over 3 years).

Accordingly, it is an object of the present invention to provide novel selective adrenoreceptor $\alpha_{2C}$ receptor antagonists for the treatment and/or prophylaxis of diseases such as, for example, cardiovascular disorders, in humans and animals.

It is another object of the present invention to provide novel selective adrenoreceptor $\alpha_{2C}$ receptor antagonists for the treatment and/or prophylaxis of peripheal circulatory disturbances (microangiopathies) such as, for example, diabetic retinopathy, diabetic nephropathy and wound healing disorders (diabetic foot ulcers).

WO 2005/042517, WO 2003/020716, WO 2002/081449 and WO 2000/066559 describe structurally similar bipiperidinyl derivatives as inhibitors of the CCR5 receptor, inter alfa for the treatment of HIV. WO 2005/077369 describes structurally similar bipiperidinyl derivatives as inhibitors of the CCR3 receptor, inter alfa for the treatment of asthma. WO 94/22826 describes structurally similar piperidines as active compounds having peripheral vasodilating action.

The invention provides compounds of the formula (I)

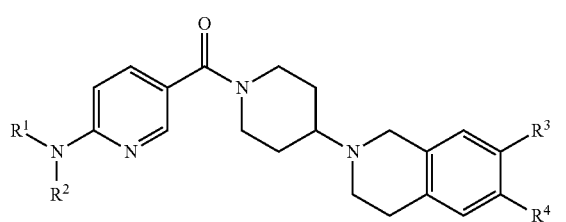

(I)

in which
$R^1$ represents $C_1$-$C_6$-alkyl or $C_3$-$C_5$-cycloalkyl,
  where alkyl is substituted by 1 to 2 substituents independently of one another selected from the group consisting of hydroxy, $C_1$-$C_4$-alkoxy and haloalkoxy
and
$R^2$ represents hydrogen or $C_1$-$C_4$-alkyl,
or
$R^1$ and $R^2$ together with the nitrogen atom to which they are attached form a 4- to 7-membered N-heterocycle,
  where the N-heterocycle may be substituted by 1 to 3 substituents independently of one another selected from the group consisting of oxo, hydroxy, monofluoromethyl, difluoromethyl, trifluoromethyl, hydroxycarbonyl, tert-butoxycarbonyl, aminocarbonyl, $C_1$-$C_4$-alkyl, $C_1$-$C_4$-alkoxy, $C_1$-$C_4$-alkoxy-$C_1$-$C_4$-alkyl, halogen and hydroxyalkyl,
or
where the N-heterocycle may have two substituents which, together with the carbon atom of the N-heterocycle to which they are jointly attached, form a 4- to 6-membered heterocycle,
  where this heterocycle for its part may be substituted by 1 to 3 substituents independently of one another selected from the group consisting of oxo, methyl and ethyl,
$R^3$ represents hydrogen, fluorine, methoxy or ethoxy,
and
$R^4$ represents hydrogen, fluorine, methoxy or ethoxy,
and the salts thereof, the solvates thereof and the solvates of the salts thereof.

DETAILED DESCRIPTION

Figure 1:
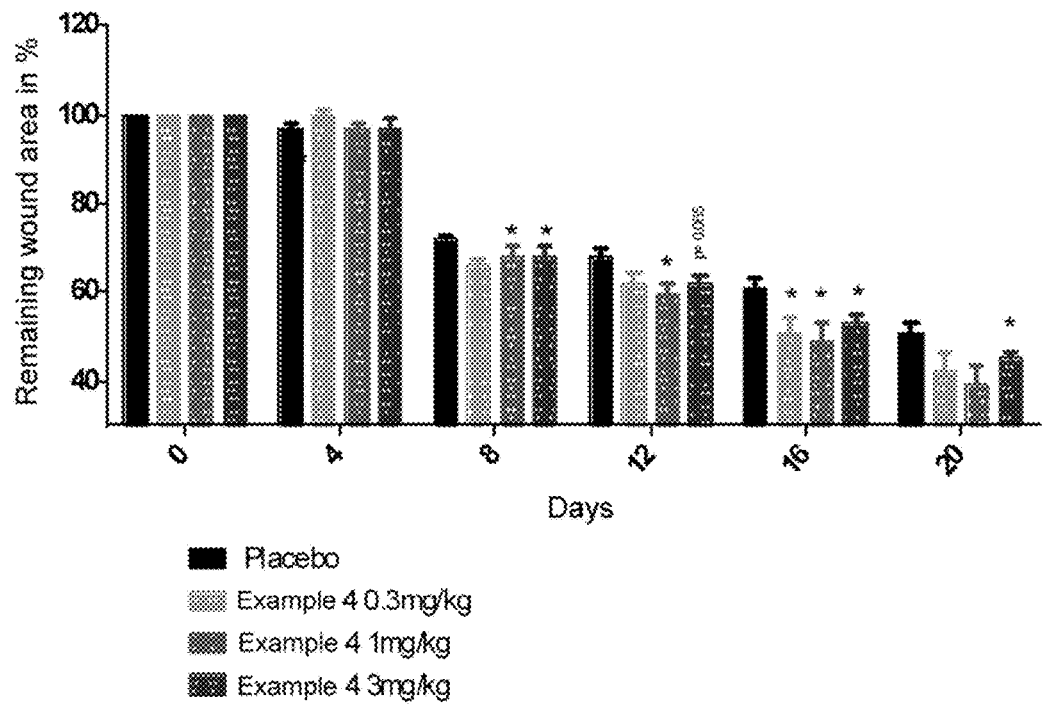
FIG. 1: B-2h) Examination of substances affecting wound healing (ulcer model). Remaining wound area in % compared to placebo-treated animals in dbdb mice. Mean±SEM (n=10).
Figure 2:
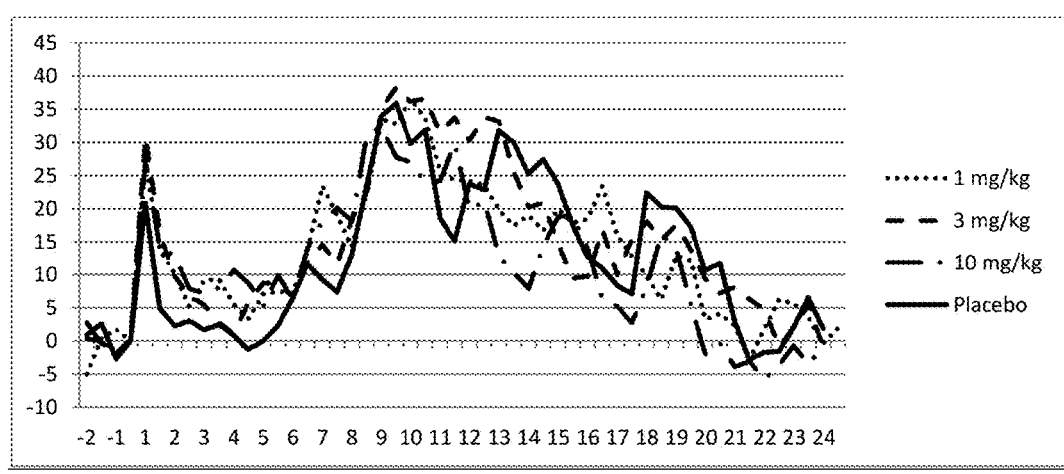
FIG. 2: B-2l) Heart rate in % deviation as a function of the time [h] after substance administration, compound of Example 4
Figure 3:
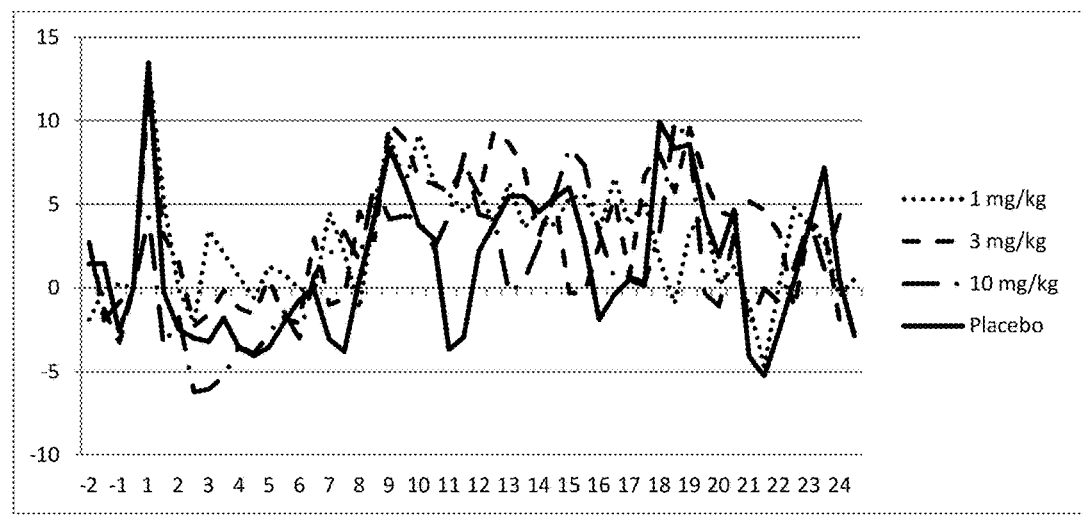
FIG. 3: B-2l) Mean arterial blood pressure in % deviation as a function of the time [h] after substance administration, compound of Example 4
Figure 4:
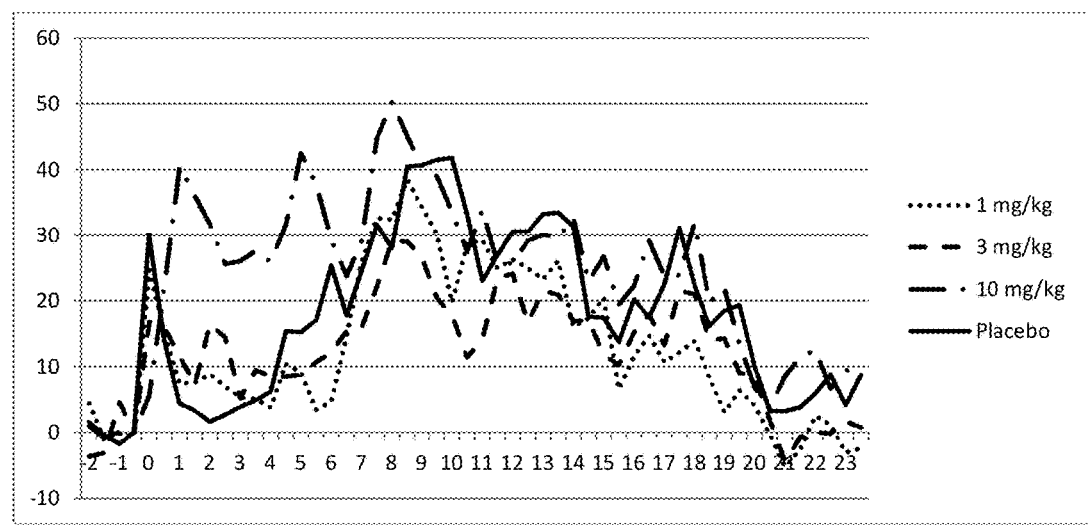
FIG. 4: B-2l) Heart rate in % deviation as a function of the time [h] after substance administration, Comparative Example ORM12741
Figure 5:
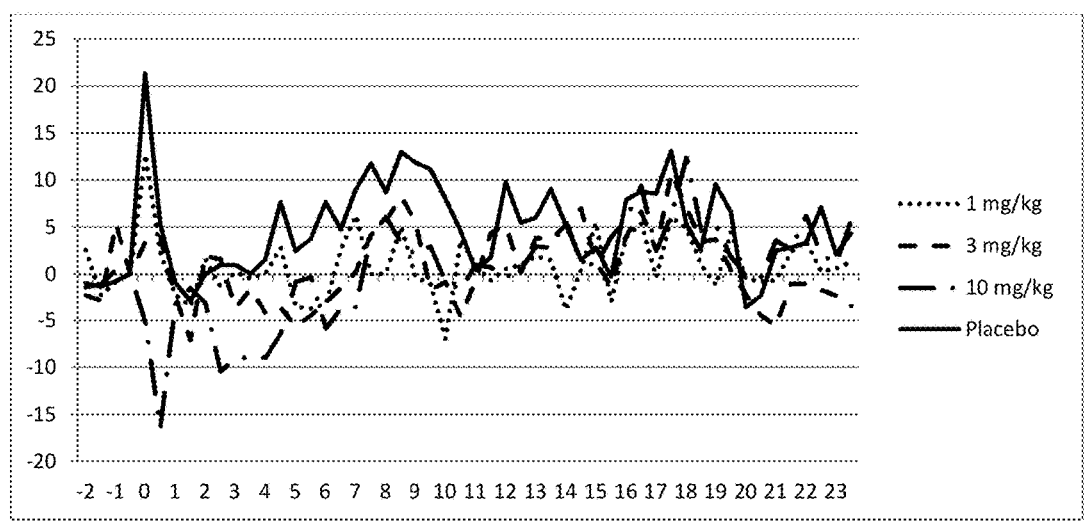
FIG. 5: B-2l) Mean arterial blood pressure in % deviation as a function of the time [h] after substance administration, Comparative Example ORM12741

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

In the context of the present invention, the term "x acid" in any formula does not mean a stoichiometrically defined ratio of acid to the respective substance. Depending, for example, on the basicity of the substance in question, the term "x acid" denotes various ratios of substance to acid, such as 10:1 to 1:10; 8:1 to 1:8; 7:1 to 1:7; 5:1 to 1:5; 4.5:1 to 1:4.5; 4:1 to 1:4; 3.5:1 to 1:3.5; 3:1 to 1:3; 2.5:1 to 1:2.5; 2:1 to 1:2; 1.5:1 to 1:1.5; and 1:1.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}$H (deuterium), $^{3}$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^{3}$H or $^{14}$C isotopes are suitable for this purpose. In addition, the incorporation of isotopes, for example of deuterium, can lead to particular therapeutic benefits as a consequence of greater metabolic stability of the compound, for example to an extension of the half-life in the body or to a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Preferred salts in the context of the present invention are physiologically acceptable salts of the compounds according to the invention. The invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates in the context of the invention are described as those forms of the compounds according to the invention which form a complex in the solid or liquid state by coordination with solvent molecules. Hydrates are a specific form of the solvates in which the coordination is with water.

In addition, the present invention also encompasses prodrugs of the compounds according to the invention. The term "prodrugs" includes compounds which may themselves be biologically active or inactive but are converted to compounds according to the invention while resident in the body (for example metabolically or hydrolytically).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, unless specified otherwise, the substituents are defined as follows:

Alkyl per se and "Alk" and "alkyl" in alkoxy, alkoxyalkyl, alkylamino and alkoxycarbonyl represent a straight-chain or branched alkyl radical having 1 to 6 carbon atoms, preferably 1 to 4 carbon atoms, by way of example and with preference methyl, ethyl, n-propyl, isopropyl, n-butyl, sec-butyl, tert-butyl, n-pentyl and n-hexyl.

Alkoxy, by way of example and with preference, represents methoxy, ethoxy, n-propoxy, isopropoxy, n-butoxy and tert-butoxy.

Alkoxyalkyl, by way of example and with preference, represents methoxymethyl, ethoxymethyl, n-propoxymethyl, isopropoxymethyl, n-butoxymethyl, tert-butoxymethyl, methoxyethyl, ethoxyethyl, n-propoxyethyl, isopropoxyethyl, n-butoxyethyl and tert-butoxyethyl.

N-Heterocycle in the definition of the radicals $R^1$ and $R^2$ represents a saturated and partially unsaturated monocyclic radical having 4 to 7 ring atoms having a nitrogen heteroatom and up to 3 further heteroatoms and/or hetero groups from the group consisting of S, O, N, SO and $SO_2$, where a nitrogen atom may also form an N-oxide, by way of example and with preference azetidine, pyrrolidine, piperidine, azepane, piperazine, morpholine, thiomorpholine, 1-oxidothiomorpholine and 1,1-dioxidothiomorpholine, particularly preferably azetidine, pyrrolidine, morpholine and 1,1-dioxidothiomorpholine.

Heterocycle in the definition of the radicals $R^1$ and $R^2$, having a joint carbon atom with the N-heterocycle to which it is attached, represents a saturated and partially unsaturated monocyclic radical having 4 to 6 ring atoms and up to 4 heteroatoms and/or hetero groups from the group consisting of S, O, N, SO and $SO_2$, where a nitrogen atom may also form an N-oxide, by way of example and with preference azetidine, oxetane, thietane, pyrrolidine, tetrahydrofuran, piperidine, morpholine, thiomorpholine, piperazine, tetrahydropyran and 1,1-dioxidothietane, particularly preferably azetidine, oxetane and 1,1-dioxidothietane, and even more preferably oxetane and 1,1-dioxidothietane.

Halogen represents fluorine, chlorine, bromine and iodine, preferably fluorine and chlorine.

Preference is given to compounds of the formula (I) in which
$R^1$ represents $C_1$-$C_6$-alkyl,
where alkyl is substituted by 1 to 2 substituents independently of one another selected from the group consisting of hydroxy and $C_1$-$C_4$-alkoxy
and
$R^2$ represents hydrogen or $C_1$-$C_4$-alkyl,
or
$R^1$ and $R^2$ together with the nitrogen atom to which they are attached form a 4- to 7-membered N-heterocycle,
where the N-heterocycle may be substituted by 1 to 3 substituents independently of one another selected from the group consisting of oxo, hydroxy, monofluoromethyl, difluoromethyl, trifluoromethyl, hydroxycarbonyl, tert-butoxycarbonyl, aminocarbonyl, $C_1$-$C_4$-alkyl, $C_1$-$C_4$-alkoxy and halogen,
or
where the N-heterocycle may have two substituents which, together with the carbon atom of the N-heterocycle to which they are jointly attached, form a 4- to 6-membered heterocycle,
where this heterocycle for its part may be substituted by 1 to 3 substituents independently of one another selected from the group consisting of oxo, methyl and ethyl,
$R^3$ represents hydrogen, fluorine, methoxy or ethoxy,
and
$R^4$ represents hydrogen, fluorine, methoxy or ethoxy,
and the salts thereof, the solvates thereof and the solvates of the salts thereof.

Preference is given to compounds of the formula (I) in which
$R^1$ represents $C_2$-$C_6$-alkyl,
where alkyl is substituted by a substituent selected from the group consisting of hydroxy, methoxy and ethoxy,
and
$R^2$ represents hydrogen,
or
$R^1$ and $R^2$ together with the nitrogen atom to which they are attached form an azetidine, pyrrolidine, piperidine, azepane, piperazine, morpholine, thiomorpholine, 1-oxidothiomorpholine or 1,1-dioxidothiomorpholine,
where azetidine, pyrrolidine, piperidine, azepane, piperazine, morpholine, thiomorpholine, 1-oxidothiomorpholine and 1,1-dioxidothiomorpholine may be substituted by 1 to 2 substituents independently of one another selected from the group consisting of hydroxy, hydroxycarbonyl, $C_1$-$C_3$-alkyl, trifluoromethyl, methoxy and methoxymethyl,
or
where azetidine, pyrrolidine, piperidine, azepane, piperazine and morpholine may have two substituents which, together with the carbon atom of the azetidine, pyrrolidine, piperidine, azepane, piperazine or morpholine to which they are jointly attached, form an azetidine, oxetane or 1,1-dioxidothietane,
where this azetidine, oxetane or 1,1-dioxidothietane for its part may be substituted by 1 to 2 substituents independently of one another selected from the group consisting of methyl and ethyl,
$R^3$ represents hydrogen,
and
$R^4$ represents hydrogen, fluorine or methoxy
or
$R^3$ represents hydrogen, fluorine or methoxy
and
$R^4$ represents hydrogen,
and the salts thereof, the solvates thereof and the solvates of the salts thereof.

Preference is given to compounds of the formula (I) in which
$R^1$ represents $C_2$-$C_4$-alkyl,
where alkyl is substituted by a substituent selected from the group consisting of hydroxy and methoxy,
and
$R^2$ represents hydrogen,
or
$R^1$ and $R^2$ together with the nitrogen atom to which they are attached form an azetidine, pyrrolidine, morpholine or 1,1-dioxidothiomorpholine,
where azetidine, pyrrolidine, morpholine or 1,1-dioxidothiomorpholine may be substituted by 1 to 2 substituents selected independently from the group consisting of hydroxycarbonyl, methyl, trifluoromethyl, methoxy and methoxymethyl
or
$R^1$ and $R^2$ together with the nitrogen atom to which they are attached form an azetidine,
where the azetidine may have two substituents which, together with the carbon atom of the azetidine to which they are jointly attached, form an oxetane or 1,1-dioxidothietane,
$R^3$ represents hydrogen, fluorine or methoxy
and
$R^4$ represents hydrogen,
or
$R^3$ represents hydrogen,
and
$R^4$ represents hydrogen, fluorine or methoxy
and the salts thereof, the solvates thereof and the solvates of the salts thereof.

Preference is given to compounds of the formula (I) in which
$R^1$ represents $C_2$-$C_4$-alkyl,
where alkyl is substituted by a substituent selected from the group consisting of hydroxy and methoxy,
and
$R^2$ represents hydrogen,
or
$R^1$ and $R^2$ together with the nitrogen atom to which they are attached form an azetidine, pyrrolidine, morpholine or 1,1-dioxidothiomorpholine,
where azetidine, pyrrolidine, morpholine or 1,1-dioxidothiomorpholine may be substituted by 1 to 2 substituents selected independently from the group consisting of hydroxycarbonyl, methyl, trifluoromethyl, methoxy and methoxymethyl
or
$R^1$ and $R^2$ together with the nitrogen atom to which they are attached form an azetidine,
where the azetidine may have two substituents which, together with the carbon atom of the azetidine to which they are jointly attached, form an oxetane or 1,1-dioxidothietane,
$R^3$ represents hydrogen or fluorine,
and
$R^4$ represents hydrogen, fluorine or methoxy,
and the salts thereof, the solvates thereof and the solvates of the salts thereof.

Preference is given to compounds of the formula (I) in which
$R^1$ and $R^2$ together with the nitrogen atom to which they are attached form a 1,1-dioxidothiomorpholine or azetidine,
where the azetidine has two substituents which, together with the carbon atom of the azetidine to which they are jointly attached, form an oxetane, $R^3$ represents hydrogen,
and
$R^4$ represents hydrogen,
and the salts thereof, the solvates thereof and the solvates of the salts thereof.

Preference is given to compounds of the formula (I) in which
$R^1$ represents $C_1$-$C_6$-alkyl,
where alkyl is substituted by 1 to 2 substituents independently of one another selected from the group consisting of hydroxy, $C_1$-$C_4$-alkoxy and cycloalkyloxy
and
$R^2$ represents hydrogen or $C_1$-$C_4$-alkyl,
or
$R^1$ and $R^2$ together with the nitrogen atom to which they are attached form a 4- to 7-membered N-heterocycle,
where the N-heterocycle may be substituted by 1 to 3 substituents independently of one another selected from the group consisting of oxo, hydroxy, monofluoromethyl, difluoromethyl, trifluoromethyl, hydroxycarbonyl, tert-butoxycarbonyl, aminocarbonyl, $C_1$-$C_4$-alkyl, $C_1$-$C_4$-alkoxy and halogen,
or
where the N-heterocycle may have two substituents which, together with the carbon atom of the N-heterocycle to which they are jointly attached, form a 4- to 6-membered heterocycle,
where this heterocycle for its part may be substituted by 1 to 3 substituents independently of one another selected from the group consisting of oxo, methyl and ethyl,
$R^3$ represents hydrogen, fluorine, methoxy or ethoxy,
and
$R^4$ represents hydrogen, fluorine, methoxy or ethoxy,
and the salts thereof, the solvates thereof and the solvates of the salts thereof.

Preference is given to compounds of the formula (I) in which
$R^1$ represents $C_2$-$C_6$-alkyl,
where alkyl is substituted by a substituent selected from the group consisting of hydroxy, methoxy and ethoxy,
and
$R^2$ represents hydrogen,
or
$R^1$ and $R^2$ together with the nitrogen atom to which they are attached form an azetidine, pyrrolidine, piperidine, azepane, piperazine, morpholine, thiomorpholine, 1-oxidothiomorpholine or 1,1-dioxidothiomorpholine,
where azetidine, pyrrolidine, piperidine, azepane, piperazine, morpholine, thiomorpholine, 1-oxidothiomorpholine and 1,1-dioxidothiomorpholine may be substituted by 1 to 2 substituents independently of one another selected from the group consisting of hydroxy, hydroxycarbonyl, $C_1$-$C_3$-alkyl, trifluoromethyl and methoxy,
or
where azetidine, pyrrolidine, piperidine, azepane, piperazine and morpholine may have two substituents which, together with the carbon atom of the azetidine, pyrrolidine, piperidine, azepane, piperazine or morpholine to which they are jointly attached, form an azetidine, oxetane or 1,1-dioxidothietane,
where this azetidine, oxetane or 1,1-dioxidothietane for its part may be substituted by 1 to 2 substituents independently of one another selected from the group consisting of methyl and ethyl,
$R^3$ represents hydrogen,
and
$R^4$ represents hydrogen, fluorine or methoxy
or
$R^3$ represents hydrogen, fluorine or methoxy
and
$R^4$ represents hydrogen,
and the salts thereof, the solvates thereof and the solvates of the salts thereof.

Preference is also given to compounds of the formula (I) in which
$R^1$ represents $C_2$-$C_6$-alkyl,
where alkyl is substituted by a substituent selected from the group consisting of hydroxy, methoxy and ethoxy,
and
$R^2$ represents hydrogen,
or
$R^1$ and $R^2$ together with the nitrogen atom to which they are attached form an azetidine, pyrrolidine, piperidine, azepane, piperazine, morpholine, thiomorpholine, 1-oxidothiomorpholine or 1,1-dioxidothiomorpholine,
where azetidine, pyrrolidine, piperidine, azepane, piperazine, morpholine, thiomorpholine, 1-oxidothiomorpholine and 1,1-dioxidothiomorpholine may be substituted by 1 to 2 substituents independently of one another selected from the group consisting of hydroxy, hydroxycarbonyl, $C_1$-$C_3$-alkyl, trifluoromethyl and methoxy,
or
where azetidine, pyrrolidine, piperidine and azepane may have two substituents which, together with the carbon atom of the azetidine, pyrrolidine, piperidine or azepane to which they are jointly attached, form an azetidine, oxetane or 1,1-dioxidothietane,
where this azetidine, oxetane or 1,1-dioxidothietane for its part may be substituted by 1 to 2 substituents independently of one another selected from the group consisting of methyl and ethyl,
$R^3$ represents hydrogen,
and
$R^4$ represents hydrogen, fluorine or methoxy
or
$R^3$ represents hydrogen, fluorine or methoxy
and
$R^4$ represents hydrogen,
and the salts thereof, the solvates thereof and the solvates of the salts thereof.

Preference is also given to compounds of the formula (I) in which
$R^1$ represents $C_2$-$C_4$-alkyl,
where alkyl is substituted by a substituent selected from the group consisting of hydroxy and methoxy,
and
$R^2$ represents hydrogen,
or
$R^1$ and $R^2$ together with the nitrogen atom to which they are attached form an azetidine, pyrrolidine, morpholine or 1,1-dioxidothiomorpholine,
where azetidine, pyrrolidine, morpholine or 1,1-dioxidothiomorpholine may be substituted by 1 to 2 substituents selected independently from the group consisting of oxo, hydroxy, hydroxycarbonyl, methyl and trifluoromethyl,
or
$R^1$ and $R^2$ together with the nitrogen atom to which they are attached form an azetidine, where the azetidine may have two substituents which, together with the carbon atom of the azetidine to which they are jointly attached, form an oxetane or 1,1-dioxidothietane, R³ represents hydrogen or fluorine, and R⁴ represents hydrogen, and the salts thereof, the solvates thereof and the solvates of the salts thereof.

Preference is also given to compounds of the formula (I) in which

R¹ represents C₂-C₆-alkyl,
where alkyl is substituted by a substituent selected from the group consisting of hydroxy, methoxy and ethoxy, and R² represents hydrogen, and the salts thereof, the solvates thereof and the solvates of the salts thereof.

Preference is also given to compounds of the formula (I) in which

R¹ and R² together with the nitrogen atom to which they are attached form an azetidine, pyrrolidine, morpholine or 1,1-dioxidothiomorpholine,
where azetidine, pyrrolidine, morpholine or 1,1-dioxidothiomorpholine may be substituted by 1 to 2 substituents selected independently from the group consisting of oxo, hydroxy, hydroxycarbonyl, methyl and trifluoromethyl, or R¹ and R² together with the nitrogen atom to which they are attached form an azetidine,
where the azetidine may have two substituents which, together with the carbon atom of the azetidine to which they are jointly attached, form an oxetane or 1,1-dioxidothietane, and the salts thereof, the solvates thereof and the solvates of the salts thereof.

Preference is also given to compounds of the formula (I) in which R² represents hydrogen.

Preference is also given to compounds of the formula (I) in which R¹ and R² together with the nitrogen atom to which they are attached represent 2-oxa-6-azaspiro[3.3]hept-6-yl.

Preference is also given to compounds of the formula (I) in which R¹ and R² together with the nitrogen atom to which they are attached represent 2,2-dioxido-2-thia-6-azaspiro[3.3]hept-6-yl.

Preference is also given to compounds of the formula (I) in which R¹ and R² together with the nitrogen atom to which they are attached represent 1,1-dioxidothiomorpholin-4-yl.

Preference is also given to compounds of the formula (I) in which R³ represents fluorine.

Preference is also given to compounds of the formula (I) in which R³ represents hydrogen.

Preference is also given to compounds of the formula (I) in which R⁴ represents hydrogen.

Preference is also given to compounds of the formula (I) in which R³ and R⁴ represent hydrogen.

Preference is also given to compounds of the formula (I) in which R³ represents fluorine and R⁴ represents hydrogen.

The individual radical definitions specified in the particular combinations or preferred combinations of radicals are, independently of the particular combinations of the radicals specified, also replaced as desired by radical definitions of other combinations.

Very particular preference is given to combinations of two or more of the abovementioned preferred ranges.

The invention further provides a process for preparing the compounds of the formula (I), or the salts thereof, solvates thereof and the solvates of the salts thereof, wherein

[A] compounds of the formula (II)

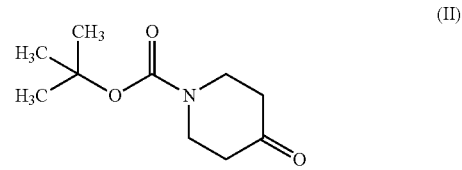

are reacted with compounds of the formula (III)

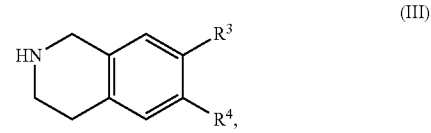

in which R³ and R⁴ have the meanings given above, in the presence of a reducing agent to give compounds of the formula (IV)

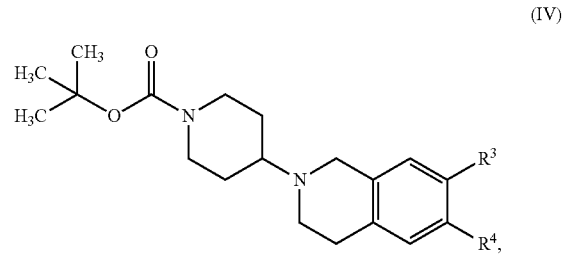

in which R³ and R⁴ have the meanings given above, or

[B] compounds of the formula (IV)

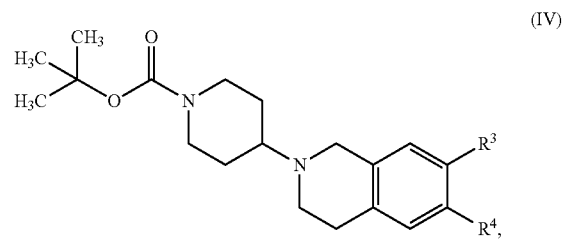

in which R³ and R⁴ have the meanings given above, are reacted in the presence of an acid to give compounds of the formula (V)

(V)

[structure: HN-piperidine-N-tetrahydroisoquinoline with R³, R⁴; x acid]

in which R³ and R⁴ have the meanings given above,
or
[C] compounds of the formula (VI)

(VI)

[structure: X-pyridine-C(=O)-O-R⁵]

in which
X represents halogen, preferably fluorine, chlorine or bromine, or sulphonylmethane and
R⁵ represents $C_1$-$C_4$-alkyl, preferably methyl or ethyl,
are reacted in the presence of a base with compounds of the formula (VII)

(VII)

[structure: R¹-NH-R²]

in which R¹ and R² have the meaning given above,
to give compounds of the formula (VIII)

(VIII)

[structure: R¹R²N-pyridine-C(=O)-O-R⁵]

in which R¹, R² and R⁵ have the meaning given above,
or
[D] compounds of the formula (IX)

(IX)

[structure: X-pyridine-COOH]

in which
X represents halogen, preferably fluorine, chlorine or bromine, or sulphonylmethane, are reacted with compounds of the formula (VII)

(VII)

[structure: R¹-NH-R²]

in which R¹ and R² have the meaning given above,
to give compounds of the formula (X)

(X)

[structure: R¹R²N-pyridine-COOH]

in which R¹ and R² have the meaning given above,
or
[E] compounds of the formula (X)

(X)

[structure: R¹R²N-pyridine-COOH]

in which R¹ and R² have the meaning given above,
are reacted with compounds of the formula (V)

(V)

[structure: HN-piperidine-N-tetrahydroisoquinoline with R³, R⁴; x acid]

in which R³ and R⁴ have the meanings given above,
in the presence of a dehydrating agent to give compounds of the formula (I)
or
[F] compounds of the formula (IX)

(IX)

[structure: X-pyridine-COOH]

in which
X represents halogen, preferably fluorine, chlorine or bromine, or sulphonylmethane are reacted with compounds of the formula (V)

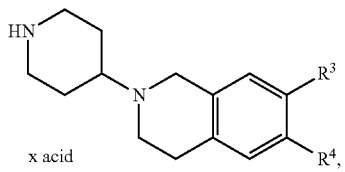

in which $R^3$ and $R^4$ have the meanings given above,
in the presence of a dehydrating agent to give compounds of the formula (XI)

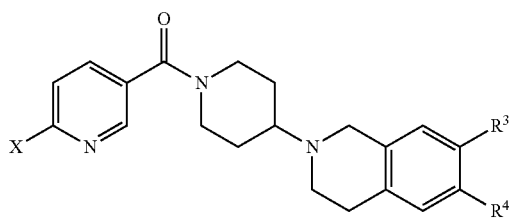

in which
$R^3$ and $R^4$ have the meanings given above and
X represents halogen, preferably fluorine, chlorine or bromine, or sulphonylmethane
or
[G] compounds of the formula (XI)

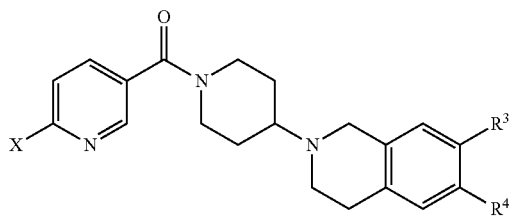

in which
$R^3$ and $R^4$ have the meanings given above and
X represents halogen, preferably fluorine, chlorine or bromine, or sulphonylmethane
are reacted with compounds of the formula (VII)

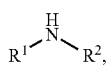

in which $R^1$ and $R^2$ have the meaning given above,
to give compounds of the formula (I).

The reaction according to process [A] is generally carried out in inert solvents, preferably in a temperature range of from −20° C. to 60° C. at atmospheric pressure and in the presence of a base.

Inert solvents are, for example, alcohols such as methanol, ethanol, n-propanol or isopropanol, or ethers such as diethyl ether, dioxane or tetrahydrofuran, or dimethylformamide, or acetic acid or glacial acetic acid, or dichloromethane, trichloromethane or 1,2-dichloroethane. It is also possible to use mixtures of the solvents mentioned. Preference is given to dichloromethane or tetrahydrofuran.

Bases are, for example, organic bases such as trialkylamines, for example triethylamine, N-methylmorpholine, N-methylpiperidine, 4-dimethylaminopyridine or diisopropylethylamine; preference is given to diisopropylethylamine.

Reducing agents are, for example, sodium borohydride, lithium borohydride, sodium cyanoborohydride, lithium aluminium hydride, sodium bis-(2-methoxyethoxy)aluminium hydride, sodium triacetoxyborohydride or borane/tetrahydrofuran; preference is given to sodium triacetoxyborohydride.

The compounds of the formulae (II) and (III) are known or can be synthesized by known processes from the appropriate starting materials.

Alternatively to process [A] described above, the preparation of the compounds of the formula (IV) may also comprise a process where
[H] compounds of the formula (II)

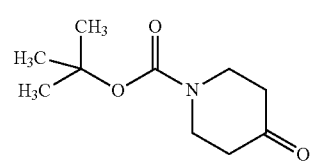

are reacted with compounds of the formula (III)

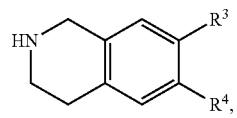

in which $R^3$ and $R^4$ have the meanings given above,
to give compounds of the formula (IVa)

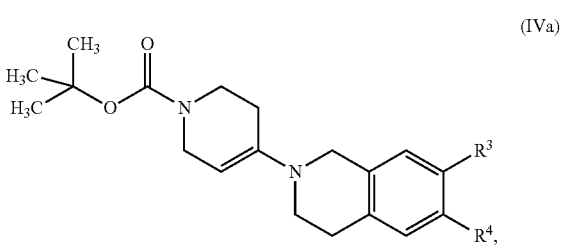

in which $R^3$ and $R^4$ have the meanings given above,
or
[I] compounds of the formula (IVa)

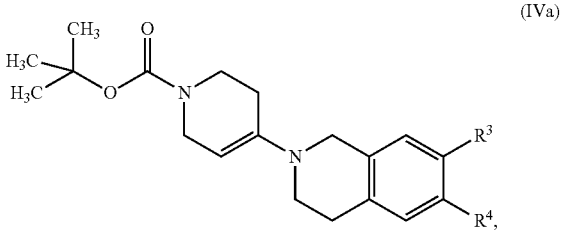

in which $R^3$ and $R^4$ have the meanings given above,
are reacted in the presence of a reducing agent to give compounds of the formula (IV).

Reducing agents in a reaction according to process [I] can be, for example, sodium borohydride, lithium borohydride, sodium cyanoborohydride, lithium aluminium hydride, sodium bis-(2-methoxyethoxy)aluminium hydride, sodium triacetoxyborohydride, borane/tetrahydrofuran, or hydrogen in the presence of palladium catalysts.

The reaction according to process [B] is generally carried out in inert solvents, preferably in a temperature range from −20° C. to 60° C. at atmospheric pressure.

Inert solvents are, for example, alcohols such as methanol, ethanol, n-propanol or isopropanol, or ethers such as diethyl ether, dioxane or tetrahydrofuran, or dimethylformamide, or dichloromethane, trichloromethane or 1,2-dichloroethane. It is also possible to use mixtures of the solvents mentioned. Preference is given to dichloromethane Acids are, for example, hydrogen chloride and trifluoroacetic acid; preference is given to hydrogen chloride. These acids are preferably added dissolved in an inert solvent. A solvent which is preferred for this purpose is dioxane.

The reaction according to process [C] is generally carried out in inert solvents, preferably in a temperature range from 0° C. to 80° C. at atmospheric pressure.

Inert solvents are, for example, alcohols such as isopropanol or ethers such as diethyl ether, dioxane, tetrahydrofuran or N-methylmorpholinone, or dimethylformamide, or dichloromethane, trichloromethane, 1,2-dichloroethane, or acetonitrile. Preference is given to acetonitrile. It is also possible to use mixtures of the solvents mentioned.

Bases are, for example, alkali metal carbonates, for example sodium carbonate, potassium carbonate or caesium carbonate, or sodium bicarbonate, potassium bicarbonate or caesium bicarbonate, or organic bases such as trialkylamines, for example triethylamine, N-methylmorpholine, N-methylpiperidine, 4-dimethylaminopyridine or diisopropylethylamine, with potassium carbonate and sodium carbonate being preferred.

The compounds of the formulae (VI) and (VII) are known or can be synthesized by known processes from the appropriate starting materials.

The reaction according to process [D] is generally carried out in inert solvents, if appropriate in a microwave apparatus, preferably in a temperature range of from 100° C. to 220° C. at from atmospheric pressure to 20 bar.

Inert solvents are, for example, alcohols, such as isopropanol, or ethers such as diethyl ether, dioxane, tetrohydrofuran, or N-methylmorpholinone, or dimethylformamide, or dichloromethane, trichloromethane, 1,2-dichloroethane or acetonitrile. It is also possible to use mixtures of the solvents mentioned. It is also possible to use at least one of the reaction partners, for example morpholines, as solvent. Preference is given to n-propanol or morpholine.

The compounds of the formulae (IX) and (VII) are known or can be prepared by known processes from the appropriate starting materials.

The reaction according to process [E] is generally carried out in inert solvents, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbons, such as benzene, nitromethane, dioxane, dimethylformamide or acetonitrile. It is also possible to use mixtures of the solvents mentioned. Particular preference is given to acetonitrile.

Suitable dehydrating agents are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride (T3P), or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates such as sodium carbonate, potassium carbonate, caesium carbonate, sodium bicarbonate, potassium bicarbonate or caesium bicarbonate, or organic bases such as trialkylamines, for example triethylamine, N-methylmorpholine, N-methylpiperidine, 4-dimethylaminopyridine or diisopropylethylamine, with diisopropylethylamine being preferred.

The condensation is preferably carried out using propanephosphonic anhydride.

The compounds of the formula (X) are obtained, for example, by a reaction according to process [D] or can be prepared by hydrolyzing the carboxylic ester in compounds of the formula (VIII).

The hydrolysis is generally carried out in inert solvents, in the presence of at least one base, preferably in a temperature range from 0° C. to 90° C. at atmospheric pressure.

Bases are, for example, alkali metal hydroxides such as lithium hydroxide or sodium hydroxide, which can each be employed in the form of an aqueous solution. Preference is given to aqueous solutions of lithium hydroxide and sodium hydroxide.

Inert solvents are, for example, polar solvents such as alcohols, for example methanol, ethanol, n-propanol or isopropanol, or ethers such as diethyl ether, dioxane, tetrahydrofuran or N-methylmorpholine. It is also possible to use mixtures of the solvents mentioned. Preference is given to dioxane, ethanol and mixtures of tetrahydrofuran and methanol.

The reaction according to process [F] is generally carried out in inert solvents, if appropriate in the presence of a base, preferably in a temperature range of from −30° C. to 50° C. at atmospheric pressure.

Inert solvents are, for example, halogenated hydrocarbons such as dichloromethane or trichloromethane, hydrocarbons such as benzine, nitromethane, dioxane, dimethylformamide or acetonitrile. It is also possible to use mixtures of the solvents mentioned. Particular preference is given to acetonitrile.

Here, suitable dehydrating agents are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride (T3P), or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates such as, for example, sodium carbonate, potassium carbonate or caesium carbonate or sodium bicarbonate, potassium bicarbonate or caesium bicarbonate, or organic bases such as trialkylamines, for example triethylamine, N-methylmorpholine, N-methylpiperidine, 4-dimethylaminopyridine or diisopropylethylamine, preferably diisopropylethylamine Preferably, the condensation is carried out using propane phosphonic anhydride.

The compounds of the formula (IX) are known or can be prepared by known processes from the appropriate starting materials.

The reaction according to process [G] is generally carried out in inert solvents, if appropriate in a microwave apparatus, preferably in a temperature range of from 100° C. to 250° C. at from atmospheric pressure to 20 bar.

Inert solvents are, for example, alcohols, such as isopropanol or ethers such as diethyl ether, dioxane, tetrahydrofuran, or N-methylmorpholinone or dimethylformamide, or dichloromethane, trichloromethane, 1,2-dichloroethane, or acetonitrile or N-methyl-2-pyrrolidone. It is also possible to use mixtures of the solvents mentioned. Preference is given to 2-propanol or N-methyl-2-pyrrolidone.

The compounds of the formula (VII) are known or can be synthesized by known methods from the appropriate starting materials.

Furthermore, the preparation according to the invention of the compounds of the formula (I) may also comprise a process where

[J] compounds of the formula (X)

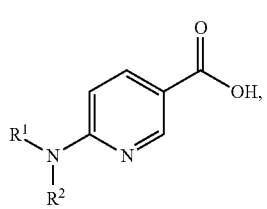

(X)

in which $R^1$ and $R^2$ have the meaning given above,
are reacted with 4-piperidinone
to give compounds of the formula (XII)

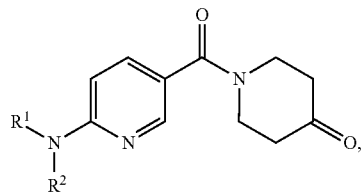

(XII)

in which $R^1$ and $R^2$ have the meanings given above,
or

[K] compounds of the formula (XII)

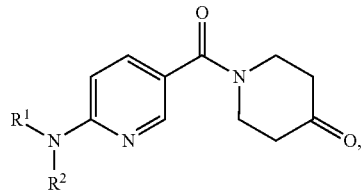

(XII)

in which $R^1$ and $R^2$ have the meanings given above,
are reacted with compounds of the formula (III)

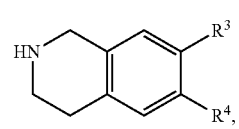

(III)

in which $R^3$ and $R^4$ have the meanings given above,
in the presence of a reducing agent to give compounds of the formula (I).

The reaction according to process [J] is carried out analogously to reactions according to process [E].

Reducing agents in a reaction according to process [K] can be, for example, sodium borohydride, lithium borohydride, sodium cyanoborohydride, lithium aluminium hydride sodium bis-(2-methoxyethoxy)aluminium hydride, sodium triacetoxyborohydride or borane/tetrahydrofuran.

The invention furthermore provides a process for preparing the compounds of the formula (I) or the salts thereof, the solvates thereof or the solvates of the salts thereof, where this process comprises reactions according to the processes described, selected from a group comprising the combinations

[A] and [B],
[H], [I] and [B],
[F] and [G],
[A], [B] and [E],
[H], [I], [B] and [E],
[A], [B] and [F],
[A], [B], [F], and [G],
[H], [I], [B] and [F],
[H], [I], [B], [F] and [G],
[C] and [E],
[D] and [E],
[A], [B], [C] and [E],
[H], [I], [B], [C] and [E],
[A], [B], [D] and [E], and
[H], [I], [B], [D] and [E].

The preparation of the compounds of the formula (I) can be illustrated by the synthesis schemes below.

Synthesis Scheme 1:
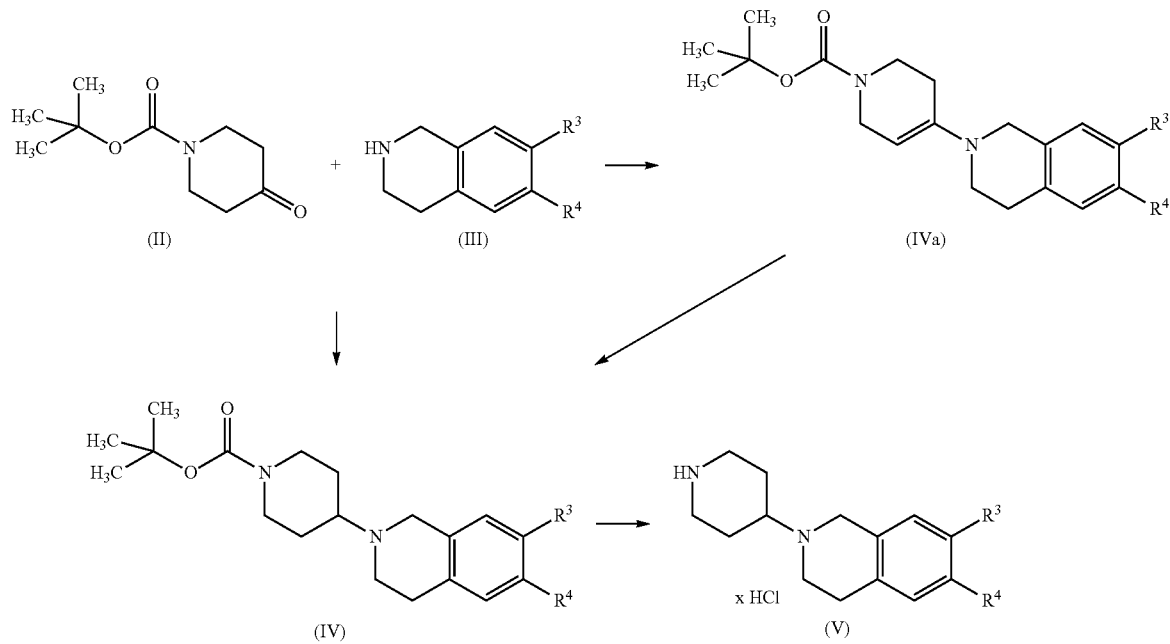
Synthesis Scheme 2:
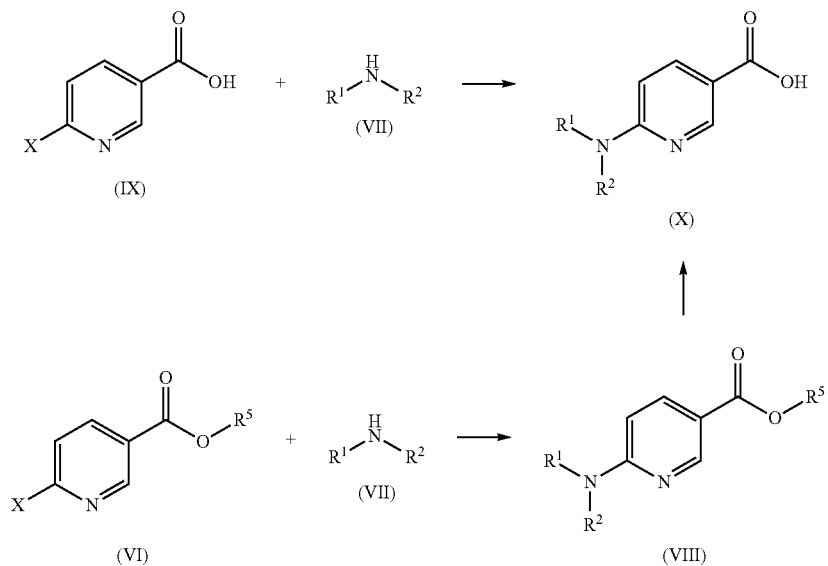
Synthesis Scheme 3:
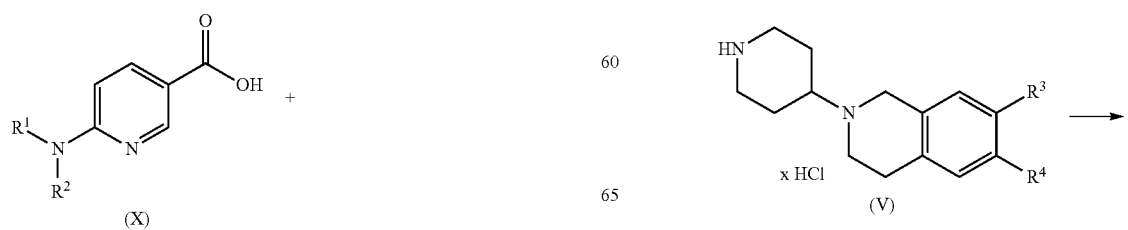

Synthesis Scheme 4:

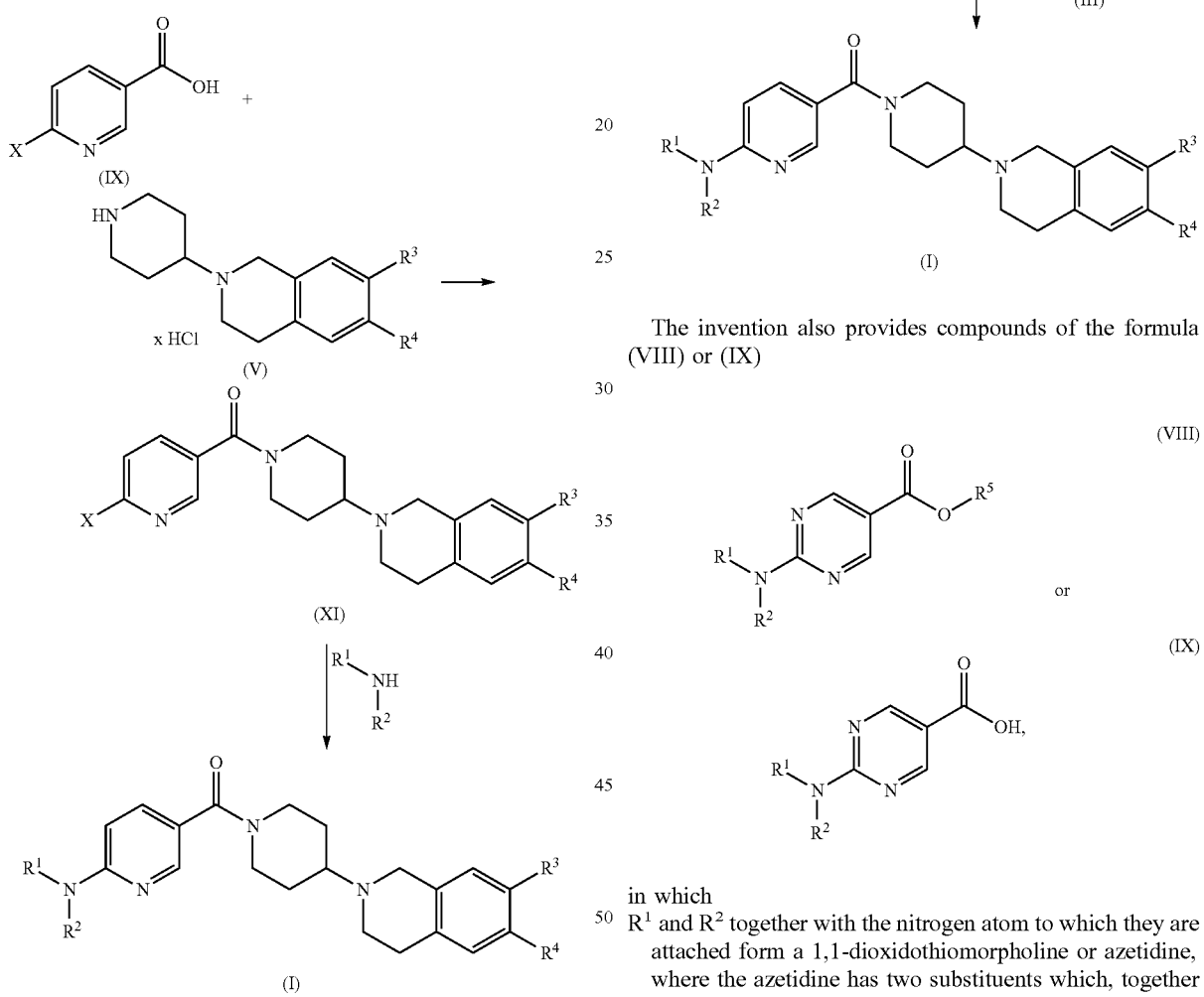

Synthesis Scheme 5:

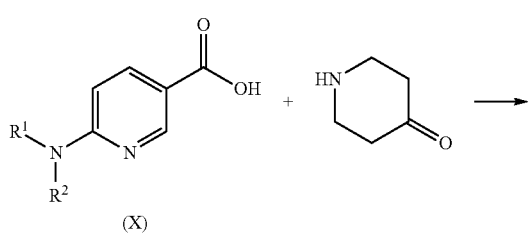

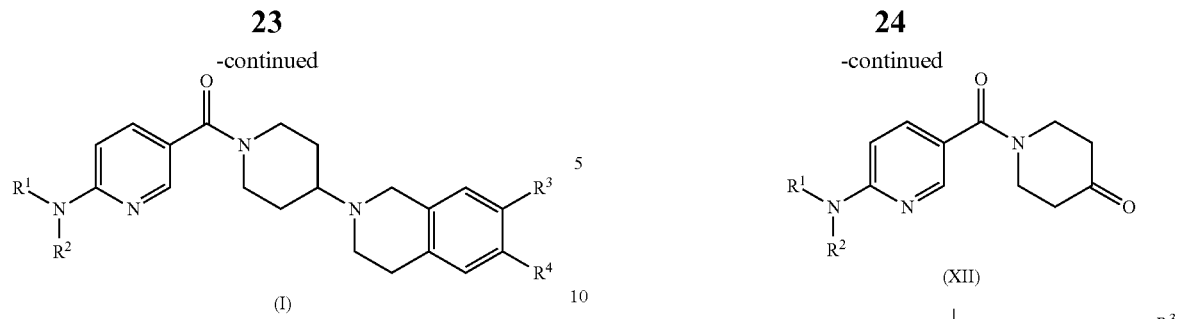

The invention also provides compounds of the formula (VIII) or (IX)

in which
R$^1$ and R$^2$ together with the nitrogen atom to which they are attached form a 1,1-dioxidothiomorpholine or azetidine, where the azetidine has two substituents which, together with the carbon atom of the azetidine to which they are jointly attached, form an oxetane,
and
R$^5$ represents C$_1$-C$_4$-alkyl, preferably methyl or ethyl,
and the salts thereof, the solvates thereof and the solvates of the salts thereof.

The compounds according to the invention have an unforeseeable useful spectrum of pharmacological activity, including useful pharmacokinetic properties. They are selective adrenoreceptor α$_{2C}$ receptor antagonists which lead to vasorelaxation and/or inhibit platelet aggregation and/or lower the blood pressure and/or increase coronary or peripheral blood flow. Accordingly, they are suitable for the treatment and/or prophylaxis of diseases, preferably cardiovascular disorders, diabetic microangiopathies, diabetic ulcers on the extremities, in particular for promoting wound healing of diabetic foot ulcers, diabetic heart failure, diabetic coronary microvascular heart disoders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies in humans and animals In particular, the compounds according to the invention show a disease-selective improvement of peripheral blood flow (micro- and macrocirculation) under pathophysiologically changed conditions, for example as a consequence of diabetes or atherosclerosis.

The compounds according to the invention are therefore suitable for use as medicaments for the treatment and/or prophylaxis of diseases in humans and animals.

Accordingly, the compounds according to the invention are suitable for the treatment of cardiovascular disorders such as, for example, for the treatment of high blood pressure, for primary and/or secondary prevention, and also for the treatment of heart failure, for the treatment of stable and unstable angina pectoris, pulmonary hypertension, peripheral and cardiac vascular disorders (e.g. peripheral occlusive disease), arrhythmias, for the treatment of thromboembolic disorders and ischemias such as myocardial infarction, stroke, transistoric and ischemic attacks, disturbances of peripheral blood flow, for the prevention of restenoses such as after thrombolysis therapies, percutaneous transluminal angioplasties (PTAs), percutaneous transluminal coronary angioplasties (PTCAs) and bypass, and also for the treatment of ischemia syndrome, arteriosclerosis, asthmatic disorders, diseases of the urogenital system such as, for example, prostate hypertrophy, erectile dysfunction, female sexual dysfunction and incontinence.

Moreover, the compounds according to the invention can be used for the treatment of primary and secondary Raynaud's phenomenon, of microcirculation impairments, intermittent claudication, peripheral and autonomic neuropathies, diabetic microangiopathies, diabetic nephropathy, diabetic retinopathy, diabetic ulcers on the extremities, diabetic erectile dysfunction, CREST syndrome, erythematosis, onychomycosis, tinnitus, dizzy spells, sudden deafness, Meniére's disease and of rheumatic disorders.

The compounds according to the invention are furthermore suitable for the treatment of respiratory distress syndromes and chronic-obstructive pulmonary disease (COPD), of acute and chronic kidney failure and for promoting wound healing and here in particular diabetic wound healing.

Moreover, the compounds of the formula (I) according to the invention are suitable for the treatment and/or prophylaxis of comorbidities and/or sequelae of diabetes mellitus. Examples of comorbidities and/or sequelae of diabetes mellitus are diabetic heart disorders such as, for example, diabetic coronary heart disorders, diabetic coronary microvascular heart disorders (coronary microvascular disease, MVD), diabetic heart failure, diabetic cardiomyopathy and myocardial infarction, hypertension, diabetic microangiopathy, diabetic retinopathy, diabetic neuropathy, stroke, diabetic nephropathy, diabetic erectile dysfunction, diabetic ulcers on the extremities and diabetic foot syndrome. Moreover, the compounds of the formula (I) according to the invention are suitable for promoting diabetic wound healing, in particular for promoting wound healing of diabetic foot ulcers. Promotion of wound healing of diabetic foot ulcers is defined, for example, as improved wound closure.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be employed for controlling states of pain.

In addition, the compounds according to the invention can also be employed for the treatment and/or prevention of micro- and macrovascular damage (vasculitis), reperfusion damage, arterial and venous thromboses, oedemas, neoplastic disorders (skin cancer, liposarcomas, carcinomas of the gastrointestinal tract, of the liver, of the pancreas, of the lung, of the kidney, of the ureter, of the prostate and of the genital tract), of disorders of the central nervous system and neurodegenerative disorders (stroke, Alzheimer's disease, Parkinson's disease, dementia, epilepsy, depressions, multiple sclerosis, schizophrenia), of inflammatory disorders, autoimmune disorders (Crohn's disease, ulcerative colitis, lupus erythematosus, rheumatoid arthritis, asthma), kidney disorders (glomerulonephritis), thyroid disorders (hyperthyreosis), hyperhydrosis, disorders of the pancreas (pancreatitis), liver fibrosis, skin disorders (psoriasis, acne, eczema, neurodermitis, dermatitis, keratitis, formation of scars, formation of warts, chilblains), skin grafts, viral disorders (HPV, HCMV, HIV), cachexia, osteoporosis, avascular bone necrosis, gout, incontinence, for wound healing, for wound healing in patients having sickle cell anaemia and for angiogenesis.

The present invention furthermore provides the use of the compounds according to the invention for the treatment and/or prophylaxis of disorders, preferably of thromboembolic disorders and/or thromboembolic complications.

"Thromboembolic disorders" in the sense of the present invention include in particular disorders such as ST-segment elevation myocardial infarction (STEMI) and non-ST-segment elevation myocardial infarction (non-STEMI), stable angina pectoris, unstable angina pectoris, reocclusions and restenoses after coronary interventions such as angioplasty, stent implantation or aortocoronary bypass, peripheral arterial occlusion diseases, pulmonary embolisms, deep venous thromboses and renal vein thromboses, transitory ischemic attacks and also thrombotic and thromboembolic stroke and pulmonary hypertension.

Accordingly, the substances are also suitable for the prevention and treatment of cardiogenic thromboembolisms, such as, for example, brain ischemias, stroke and systemic thromboembolisms and ischemias, in patients with acute, intermittent or persistent cardiac arrhythmias, such as, for example, atrial fibrillation, and those undergoing cardioversion, furthermore in patients with heart valve disorders or with intravasal objects, such as, for example, artificial heart valves, catheters, intraaortic balloon counterpulsation and pacemaker probes. In addition, the compounds according to the invention are suitable for the treatment of disseminated intravasal coagulation (DIC).

Thromboembolic complications are furthermore encountered in connection with microangiopathic haemolytic anaemias, extracorporeal circulation, such as, for example, haemodialysis, haemofiltration, ventricular assist devices and artificial hearts, and also heart valve prostheses.

The compounds according to the invention are particularly suitable for the primary and/or secondary prevention and for the treatment of heart failure.

In the context of the present invention, the term heart failure also includes more specific or related types of disease, such as right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are particularly suitable for the treatment and/or prophylaxis of cardiovascular disorders, in particular heart failure, and/or circulatory disturbances and microangiopathies associated with diabetes.

The compounds according to the invention are also suitable for the primary and/or secondary prevention and for the treatment of the abovementioned disorders in children.

The present invention further provides the compounds according to the invention for use in a method for treatment and/or prophylaxis of disorders, especially the disorders mentioned above.

The present invention further provides for the use of the compounds according to the invention for treatment and/or prophylaxis of disorders, especially the disorders mentioned above.

The present invention further provides for the use of the compounds according to the invention for production of a medicament for treatment and/or prophylaxis of disorders, especially the disorders mentioned above.

The present invention further provides a method for treatment and/or prophylaxis of disorders, especially the disorders mentioned above, using a therapeutically effective amount of a compound according to the invention.

The present invention further provides adrenoreceptor α2C receptor antagonists for use in a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides adrenoreceptor α2C receptor antagonists for use in a method for the treatment and/or prophylaxis of diabetic microangiopathy, diabetic retinopathy, diabetic neuropathy, diabetic nephropathy, diabetic erectile dysfunction, diabetic heart failure, diabetic coronary microvascular heart disorders, diabetic ulcers on the extremities, diabetic foot ulcers, for promoting diabetic wound healing, and for promoting wound healing of diabetic foot ulcers.

The present invention further provides competitive adrenoreceptor α2C receptor antagonists for use in a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides medicaments comprising at least one adrenoreceptor α2C receptor antagonist, in combination with one or more inert non-toxic pharmaceutically suitable auxiliaries for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides medicaments comprising at least one adrenoreceptor α2C receptor antagonist, in combination with one or more inert non-toxic pharmaceutically suitable auxiliaries for the treatment and/or prophylaxis of diabetic microangiopathy, diabetic retinopathy, diabetic neuropathy, diabetic nephropathy, diabetic erectile dysfunction, diabetic heart failure, diabetic coronary microvascular heart disorders, diabetic ulcers on the extremities, diabetic foot ulcers, for promoting diabetic wound healing, and for promoting wound healing of diabetic foot ulcers.

The present invention further provides medicaments comprising at least one competitive adrenoreceptor α2C receptor antagonist, in combination with one or more inert non-toxic pharmaceutically suitable auxiliaries for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides medicaments comprising at least one adrenoreceptor α2C receptor antagonist, in combination with one or more further active compounds selected from the group consisting of lipid metabolism-modulating active compounds, antidiabetics, hypotensive agents, agent which lower the sympathetic tone, perfusion-enhancing and/or antithrombotic agents and also antioxidants, aldosterone and mineralocorticoide receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressives and other psychopharmaceuticals.

The present invention further provides medicaments comprising at least one competitive adrenoreceptor α2C receptor antagonist, in combination with one or more further active compounds selected from the group consisting of lipid metabolism-modulating active compounds, antidiabetics, hypotensive agents, agent which lower the sympathetic tone, perfusion-enhancing and/or antithrombotic agents and also antioxidants, aldosterone and mineralocorticoide receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressives and other psychopharmaceuticals.

The present invention further provides a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers in humans and animals by administration of an effective amount of at least one adrenoreceptor α2C receptor antagonist or of a medicament comprising at least one adrenoreceptor α2C receptor antagonist.

The present invention further provides a method for the treatment and/or prophylaxis of diabetic microangiopathy, diabetic retinopathy, diabetic neuropathy, diabetic nephropathy, diabetic erectile dysfunction, diabetic heart failure, diabetic coronary microvascular heart disorders, diabetic ulcers on the extremities, diabetic foot ulcers, for promoting diabetic wound healing, and for promoting wound healing of diabetic foot ulcers.

The present invention further provides a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers in humans and animals by administration of an effective amount of at least one competitive adrenoreceptor α2C receptor antagonist or of a medicament comprising at least one competitive adrenoreceptor α2C receptor antagonist.

Adrenoreceptor α2C receptor antagonists according to the invention are receptor ligands or compounds that block or inhibit the biological responses induced by adrenoreceptor α2C receptor agonists. Adrenoreceptor α2C receptor antagonists according to the invention include competitive antagonists, non-competitive antagonists, inverse agonists, and allosteric modulators.

The compounds according to the invention can be used alone or, if required, in combination with other active compounds. The present invention further provides medicaments comprising a compound according to the invention and one or more further active compounds, in particular for treatment and/or prophylaxis of the disorders mentioned above. Suitable active ingredients for combination are, by way of example and by way of preference: active ingredients which modulate lipid metabolism, antidiabetics, hypotensive agents, perfusion-enhancing and/or antithrombotic agents, and also antioxidants, aldosterone- and mineralocorticoid receptor antagonists, vasopressin receptor antagonists, organic nitrates and NO donors, IP receptor agonists, positively inotropically active compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophile elastase, signal transduction cascade-inhibiting compounds, compounds that modulate the energy metabolism of the heart, chemokine receptor antagonists, p38 kinase inhibitors, NPY agonists, orexin agonists, anorectics, PAF-AH inhibitors, antiphlogistics (COX inhibitors, $LTB_4$ receptor antagonists, inhibitors of $LTB_4$ synthesis), analgesics (aspirin), antidepressants and other psychopharmaceuticals.

The present invention provides in particular combinations of at least one of the compounds according to the invention and at least one lipid metabolism-modifying active compound, antidiabetic, hypotensive active compound and/or agent having antithrombotic action.

The compounds according to the invention may preferably be combined with one or more of the active compounds mentioned below:

lipid metabolism-modulating active ingredients, by way of example and by way of preference from the group of the HMG-CoA reductase inhibitors from the class of the statins such as, by way of example and by way of preference, lovastatin, simvastatin, pravastatin, fluvastatin, atorvastatin, rosuvastatin, cerivastatin or pitavastatin, inhibitors of HMG-CoA reductase expression, squalene synthesis inhibitors such as, by way of example and by way of preference, BMS-188494 or TAK-475, ACAT inhibitors such as, by way of example and by way of preference, melinamide, pactimibe, eflucimibe or SMP-797, LDL receptor inductors, cholesterol absorption inhibitors such as, by way of example and by way of preference, ezetimibe, tiqueside or pamaqueside, polymeric bile acid adsorbers such as, by way of example and by way of preference, cholestyramine, colestipol, colesolvam, CholestaGel or colestimide, bile acid reabsorption inhibitors such as, by way of example and by way of preference, ASBT (=IBAT) inhibitors such as elobixibat (AZD-7806), S-8921, AK-105, canosimibe (BARI-1741, AVE-5530), SC-435 or SC-635, MTP inhibitors such as, by way of example and by way of preference, implitapide or JTT-130, lipase inhibitors such as, by way of example and by way of preference, orlistat, LpL activators, fibrates, niacin, CETP inhibitors such as, by way of example and by way of preference, torcetrapib, dalcetrapib (JTT-705) or CETP vaccine (Avant), PPAR-γ and/or PPAR-δ agonists such as, by way of example and by way of preference, pioglitazone or rosiglitazone and/or endurobol (GW-501516), RXR modulators, FXR modulators, LXR modulators, thyroid hormones and/or thyroid mimetics such as, by way of example and by way of preference, D-thyroxine or 3,5,3'-triiodothyronine (T3), ATP citrate lyase inhibitors, Lp(a) antagonists, cannabinoid receptor 1-antagonists such as, by way of example and by way of preference, rimonabant or surinabant (SR-147778), leptin receptor agonists, bombesin receptor agonists, histamine receptor agonists, agonists of the niacin receptor such as, by way of example and by way of preference, niacin, acipimox, acifran or radecol, and the antioxidants/radical scavengers such as, by way of example and by way of preference, probucol, succinobucol (AGI-1067), BO-653 or AEOL-10150;

antidiabetics mentioned in Die Rote Liste 2014, chapter 12. Antidiabetics are preferably understood as meaning insulin and insulin derivatives and also orally effective hypoglycemically active compounds. Here, insulin and insulin derivatives include both insulins of animal, human or biotechnological origin and mixtures thereof. The orally effective hypoglycaemically active compounds preferably include sulphonylureas, biguanides, meglitinide derivatives, glucosidase inhibitors and PPAR-gamma agonists. Sulfonylureas which may be mentioned are, by way of example and by way of preference, tolbutamide, glibenclamide, glimepiride, glipizide or gliclazide, biguanides which may be mentioned are, by way of example and by way of preference, metformin, meglitinide derivatives which may be mentioned are, by way of example and by way of preference, repaglinide or nateglinide, glucosidase inhibitors which may be mentioned are, by way of example and by way of preference, miglitol or acarbose, oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and potassium channel openers such as, for example, those disclosed in WO 97/26265 and WO 99/03861;

hypotensive active compounds, by way of example and by way of preference from the group of the calcium antagonists such as, by way of example and by way of preference, nifedipine, amlodipine, verapamil or diltiazem, angiotensin AII antagonists such as, by way of example and by way of preference, losartan, valsartan, candesartan, embusartan or telmisartan, ACE inhibitors such as, by way of example and by way of preference, enalapril, captopril, ramipril, delapril, fosinopril, quinopril, perindopril or trandopril, beta receptor blockers such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol, alpha receptor blockers such as, by way of example and by way of preference, prazosin, ECE inhibitors, rho-kinase inhibitors and of the vasopeptidase inhibitors, and also of the diuretics such as, by way of example and by way of preference, a loop diuretic such as furosemide, bumetanide or torsemide, or a thiazide or thiazide-like diuretic such as chlorothiazide or hydrochlorothiazide or A1 antagonists such as rolofylline, tonopofylline and SLV-320;

agents which lower the symphathetic tone such as, by way of example and by way of preference, reserpin, clonidine or alpha-methyldopa, or in combination with a potassium channel agonist such as, by way of example and by way of preference, minoxidil, diazoxide, dihydralazine or hydralazine;

agents with antithrombotic action such as, by way of example and by way of preference, from the group of the platelet aggregation inhibitors such as, by way of example and by way of preference, aspirin, clopidogrel, ticlopidine, cilostazol or dipyridamole, or of the anticoagulants such as thrombin inhibitors such as, by way of example and by way of preference, ximelagatran, melagatran, bivalirudin or clexane, a GPIIb/IIIa antagonist such as, by way of example and by way of preference, tirofiban or abciximab, a factor Xa inhibitor such as, by way of example and by way of preference, rivaroxaban, edoxaban (DU-176b), apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428, with heparin or a low molecular weight (LMW) heparin derivative or with a vitamin K antagonist such as, by way of example and by way of preference, coumarin;

aldosterone and mineralocorticoid receptor antagonists such as, by way of example and by way of preference, spironolactone or eplerenone;

vasopressin receptor antagonists such as, by way of example and by way of preference, conivaptan, tolvaptan, lixivaptan or satavaptan (SR-121463);

organic nitrates and NO donors such as, by way of example and by way of preference, sodium nitroprusside, nitroglycerol, isosorbide mononitrate, isosorbide dinitrate, molsidomine or SIN-1, or in combination with inhalative NO;

IP receptor agonists, preferred examples being iloprost, treprostinil, beraprost and selexipag (NS-304);

compounds having a positive inotropic effect, preferred examples being cardiac glycosides (digoxin), beta-adrenergic and dopaminergic agonists such as isoproterenol, adrenaline, noradrenaline, dopamine and dobutamine;

calcium sensitizers, a preferred example being levosimendan;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil, and PDE 3 inhibitors such as milrinone;

natriuretic peptides, for example atrial natriuretic peptide (ANP, anaritide), B-type natriuretic peptide or brain natriuretic peptide (BNP, nesiritide), C-type natriuretic peptide (CNP) and urodilatin;

NO-independent but haem-dependent stimulators of guanylate cyclase, such as especially the compounds described in WO 00/06568, WO 00/06569, WO 02/42301 and WO 03/095451;

NO- and haem-independent activators of guanylate cyclase, such as especially the compounds described in WO 01/19355, WO 01/19776, WO 01/19778, WO 01/19780, WO 02/070462 and WO 02/070510;

inhibitors of human neutrophil elastase (HNE), for example sivelestat and DX-890 (Reltran);

compounds which inhibit the signal transduction cascade, for example tyrosine kinase inhibitors and multikinase inhibitors, especially sorafenib, imatinib, gefitinib and erlotinib; and/or compounds which influence the energy metabolism of the heart, such as, for example, etomoxir, dichloroacetate, ranolazine and trimetazidine In the context of the present invention, particular preference is given to combinations comprising at least one of the compounds according to the invention and one or more further active compounds selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

Particular preference in the context of the present invention is given to combinations comprising at least one of the compounds according to the invention and one or more further active compounds selected from the group consisting of heparin, antidiabetics, ACE inhibitors, diuretics and antibiotics, and also to their use in a method for promoting diabetic wound healing and for the treatment and/or prevention of diabetic ulcers on the extremities, in particular for promoting wound healing of diabetic foot ulcers.

Particular preference in the context of the present invention is given to the use of at least one of the compounds according to the invention in a method for promoting diabetic wound healing and for the treatment and/or prevention of diabetic ulcers on the extremities, in particular for promoting wound healing of diabetic foot ulcers, where the compound of the formula (I) is additionally employed for one or more of the following physical and/or topical therapies: wound management such as dressings, wound excision, weight reduction with appropriate footwear, PDGF (Regranex), hyperbaric oxygen therapy, wound therapy with negative pressure.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

Suitable administration forms for oral administration are those which function according to the prior art and deliver the compounds according to the invention rapidly and/or in modified fashion, and which contain the compounds according to the invention in crystalline and/or amorphized and/or dissolved form, for example tablets (uncoated or coated tablets, for example having enteric coatings or coatings which are insoluble or dissolve with a delay and control the release of the inventive compound), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

Oral administration is preferred.

In the exemplary use of the compounds of the formula (I) for promoting diabetic wound healing, in particular for promoting wound healing of diabetic foot ulcers, preference, in addition to oral administration, is also given to administration in the form of a topical formulation.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds according to the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention further provides medicaments comprising at least one inventive compound, preferably together with one or more inert nontoxic pharmaceutically suitable excipients, and the use thereof for the purposes mentioned above.

In general, it has been found to be advantageous in the case of oral administration to administer amounts of from about 0.1 to 250 mg per 24 hours, preferably 0.1 to 50 mg per 24 hours, to achieve effective results. The dose may be divided into a plurality of administrations per day. Examples are administrations twice or three times per day.

It may nevertheless be necessary where appropriate to deviate from the stated amounts, specifically as a function of the body weight, route of administration, individual response to the active compound, nature of the preparation and time or interval over which administration takes place.

The present invention further provides a compound of the formula (I) as described above for use in a method for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

The present invention further provides a compound of the formula (I) as described above for use in a method for the treatment and/or prophylaxis of primary and secondary forms of heart failure, peripheral and cardiac circulatory disturbances, thromboembolic disorders and ischaemias, peripheral circulatory disturbances, Raynaud's phenomenon, microcirculatory disturbances, intermittent claudication, peripheral and autonomous neuropathies, diabetic microangiopathies, diabetic nephropathies, diabetic retinopathy, diabetic ulcers on the extremities and CREST syndrome, and also for diabetic wound healing, in particular for promoting wound healing of diabetic foot ulcers.

The present invention further provides a compound of the formula (I) as described above for preparing a medicament for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

The present invention further provides the use of a compound of the formula (I) as described above for preparing a medicament for the treatment and/or prophylaxis of primary and secondary forms of heart failure, peripheral and cardiac circulatory disturbances, thromboembolic disorders and ischaemias, peripheral circulatory disturbances, Raynaud's phenomenon, microcirculatory disturbances, intermittent claudication, peripheral and autonomous neuropathies, diabetic microangiopathies, diabetic nephropathies, diabetic retinopathy, diabetic ulcers on the extremities and CREST syndrome, and also for diabetic wound healing, in particular for promoting wound healing of diabetic foot ulcers.

The present invention further provides a medicament comprising a compound of the formula (I) as described above in combination with one or more inert non-toxic pharmaceutically suitable auxiliaries.

The present invention further provides a medicament comprising a compound of the formula (I) as described above in combination with one or more further active compounds selected from the group consisting of lipid metabolism-modulating active compounds, antidiabetics, hypotensive agents, agent which lower the sympathetic tone, perfusion-enhancing and/or antithrombotic agents and also antioxidants, aldosterone and mineralocorticoide receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressives and other psychopharmaceuticals.

The present invention further provides a medicament as described above for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

The present invention further provides a medicament as described above for the treatment and/or prophylaxis of primary and secondary forms of heart failure, peripheral and cardiac circulatory disturbances, thromboembolic disorders and ischaemias, peripheral circulatory disturbances, Raynaud's phenomenon, microcirculatory disturbances, intermittent claudication, peripheral and autonomous neuropathies, diabetic microangiopathies, diabetic nephropathies, diabetic retinopathy, diabetic ulcers on the extremities and CREST syndrome, and also for diabetic wound healing, in particular for promoting wound healing of diabetic foot ulcers.

The present invention further provides a method for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies in humans and animals by administration of an effective amount of at least one compound of the formula (I) as described above or of a medicament as described above.

The present invention further provides a method for the treatment and/or prophylaxis of primary and secondary forms of heart failure, peripheral and cardiac circulatory disturbances, thromboembolic disorders and ischaemias, peripheral circulatory disturbances, Raynaud's phenomenon, microcirculatory disturbances, intermittent claudication, peripheral and autonomous neuropathies, diabetic microangiopathies, diabetic nephropathies, diabetic retinopathy, diabetic ulcers on the extremities and CREST syndrome, and also for diabetic wound healing, in particular for promoting wound healing of diabetic foot ulcers, in humans and animals by administration of an effective amount of at least one compound of the formula (I) as described above or of a medicament as described above.

Unless stated otherwise, the percentages in the tests and examples which follow are percentages by weight; parts are parts by weight. Solvent ratios, dilution ratios and concentration data for the liquid/liquid solutions are in each case based on volume. "w/v" means "weight/volume". For example, "10% w/v" means: 100 ml of solution or suspension comprise 10 g of substance.

If, in the synthesis intermediates and working examples of the invention described below, a compound is given in the form of a salt of the corresponding base or acid, the exact stoichiometric composition of such a salt as obtained by the respective preparation and/or purification process is generally not known. Unless specified in more detail, additions to names and structural formulae, such as "hydrochloride", "trifluoroacetate", "oxalate salt", "sodium salt" or "x HCl", "x CF$_3$COOH", "xC$_2$O$_4^{2-}$", "x Na$^+$" are not to be understood stoichiometrically in the case of such salts, but have only descriptive character with regard to the salt-forming components comprised therein.

This applies correspondingly if synthesis intermediates or working examples or salts thereof were obtained by the preparation and/or purification processes described in the form of solvates, for example hydrates, of unknown stoichiometric composition (if of a defined type).

A) EXAMPLES

Abbreviations:

| | |
|---|---|
| ca. | circa |
| CDI | carbonyldiimidazole |
| d | day(s), doublet (in NMR) |
| TLC | thin-layer chromatography |
| DCI | direct chemical ionization (in MS) |
| dd | doublet of doublets (in NMR) |
| DMAP | 4-dimethylaminopyridine |
| DMF | N,N-dimethylformamide |
| DMSO | dimethyl sulphoxide |
| DSC | disuccinimidyl carbonate |
| of th. | of theory (in yield) |

-continued

Abbreviations:

| | |
|---|---|
| eq. | equivalent(s) |
| ESI | electrospray ionization (in MS) |
| h | hour(s) |
| HATU | O-(7-azabenzotriazol-1-yl)-N,N,N',N'-tetramethyluronium hexafluorophosphate |
| HPLC | high-pressure high-performance liquid chromatography |
| HV | high vacuum |
| LDA | lithium diisopropylamide |
| m | multiplet (in NMR) |
| min | minute(s) |
| MS | mass spectroscopy |
| NMR | nuclear magnetic resonance spectroscopy |
| PYBOP | benzotriazol-1-yloxy-tris(pyrrolidino)phosphonium hexafluorophosphate |
| q | quartet (in NMR) |
| RP | reverse phase (in HPLC) |
| RT | room temperature |
| $R_t$ | retention time (in HPLC) |
| s | singlet (in NMR) |
| t | triplet (in NMR) |
| T3P | propylphosphonic anhydride 50% strength in ethyl acetate or DMF |
| THF | tetrahydrofuran |

LC-MS and HPLC Methods:
Method 1 (LC-MS):
Instrument: Waters ACQUITY SQD UPLC system; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.
Method 2 (LC-MS):
Instrument: Waters ACQUITY SQD UPLC system; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.
Method 3 (LC-MS):
Instrument: Waters ACQUITY SQD UPLC system; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.60 ml/min; UV detection: 208-400 nm.
Method 4 (LC-MS):
Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.
Method 5 (LC-MS):
MS instrument: Waters (Micromass) Quattro Micro; HPLC instrument type: Agilent 1100 series; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate: 2.5 ml)→5.00 min 100% A; oven: 50° C.; flow rate: 2 ml/min; UV detection: 210 nm.

Method 6 (LC-MS):
MS instrument type: Waters ZQ; HPLC instrument type: Agilent 1100 Series; UV DAD; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100%; oven: 55° C.; flow rate: 2 ml/min; UV detection: 210 nm.
Method 7 (LC-MS):
MS instrument: Waters (Micromass) QM; HPLC instrument: Agilent 1100 series; column. Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.
Method 8 (LC-MS):
MS instrument: Waters (Micromass) Quattro Micro; HPLC instrument: Agilent 1100 series; column: YMC-Triart C18 3μ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm
Method 9 (Preparative HPLC):
Column: Waters XBridge, 50×19 mm, 10 μm, mobile phase A: water+0.5% ammonium hydroxide, mobile phase B: acetonitrile, 5 min=95% A, 25 min=50% A, 38 min=50% A, 38.1 min=5% A, 43 min=5% A, 43.01 min=95% A, 48.0 min=5% A; flow rate 20 ml/min, UV detection: 210 nm.
Method 10 (Preparative HPLC):
Column: Waters XBridge, 50×19 mm, 10 μm, mobile phase A: water, mobile phase B: acetonitrile, mobile phase C: constant+0.1% ammonium hydroxide, 0.0 min 95% A→1 min=95% A→6 min=50% A→6.1 min 5 A→7.0 min 5% A→7.1 min 95% A→100 min 95%; flow rate 25 ml/min, UV detection: 210 nm
Method 11 (Preparative HPLC):
Column: Waters XBridge, 50×19 mm, 10 μm, mobile phase A: water+0.5% ammonium hydroxide, mobile phase B: acetonitrile, 0.0 min 95% A→5.0 min=95% A→25 min=70% A→38 min=70% A→38.1 min=5% A→43 min=5% A→43.01 min=95% A→48.0 min=95% A; flow rate 20 ml/min, UV detection: 210 nm The NMR data are assigned unless the signals are obscured by solvent.

The microwave reactor used was an instrument of the Biotage Initiator™ type.

Starting Materials

Example 1A tert-Butyl 4-(3,4-dihydroisoquinoline-2(1H)-yl)piperidine-1-carboxylate

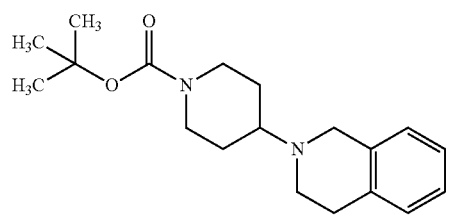 [SMILES: CC(C)(C)OC(=O)N1CCC(N2CCc3ccccc3C2)CC1]

150 g (753 mmol) of tert-butyl 4-oxopiperidine-1-carboxylate and 120 g (903 mmol) of 1,2,3,4-tetrahydroisoquinoline were dissolved in 1500 ml of THF, and 239 g (1129 mmol) of sodium triacetoxyborohydride were added with the temperature of the mixture being kept at about 30° C. The mixture was stirred at RT for about another 1 h, and about 1000 ml of saturated sodium bicarbonate solution were then added. The mixture was extracted with about 500 ml of ethyl acetate. The organic phase was washed with a further 500 ml of saturated sodium bicarbonate solution and with 200 ml of saturated sodium chloride solution. The organic phase was then dried over sodium sulphate, filtered and concentrated. This gave 234 g (98% of theory) of the target product which was processed further without further purification.

LC-MS [Method 1]: $R_t$=0.72 min; MS (ESIpos): m/z=317 (M+H)$^+$ $^1$H-NMR (400 MHz, CDCl$_3$): δ [ppm]=1.47 (s, 9H) 1.48-1.60 (m, 2H) 1.75-1.94 (m, 3H) 2.56-2.66 (m, 1H) 2.67-2.81 (m, 2H) 2.81-2.93 (m, 4H) 3.78 (s, 2H) 4.08-4.27 (m, 1H) 6.98-7.05 (m, 1H) 7.07-7.14 (m, 3H).

Example 2A 2-(Piperidin-4-yl)-1,2,3,4-tetrahydroisoquinoline hydrochloride

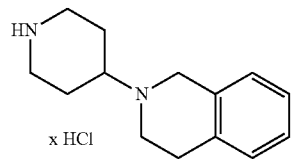 [SMILES: c1ccc2c(c1)CCN(C1CCNCC1)C2]

210 g (664 mmol) of the compound from Example 1A were dissolved in 1600 ml of dichloromethane, and 830 ml (3318 mmol) of 4M hydrogen chloride in dioxane were added, with the temperature of the mixture being kept at 25-30° C. The product started to crystallize after the addition was about ⅓ complete. The mixture was stirred at RT for about another 20 h, and about 2000 ml of tert-butyl methyl ether were then added. The resulting precipitate was filtered off with suction, washed with tert-butyl methyl ether and dried under reduced pressure. This gave 185 g (97% of theory) of the target product as a white solid.

LC-MS [Method 7]: $R_t$=2.08 min; MS (ESIpos): m/z=217 (M+H)$^+$ $^1$H-NMR (400 MHz, DMSO-d$_6$): δ [ppm]=1.96-2.20 (m, 2H), 2.28-2.44 (m, 2H), 2.81-3.51 (m, 6H), 3.51-3.80 (m, 3H), 4.33-4.51 (m, 2H), 7.17-7.35 (m, 4H), 8.92-9.10 (m, 1H), 9.12-9.32 (m, 1H), 11.47 (br. s, 1H).

Example 3A tert-Butyl 4-(6-fluoro-3,4-dihydroisoquinolin-2(1H)-yl)piperidine-1-carboxylate

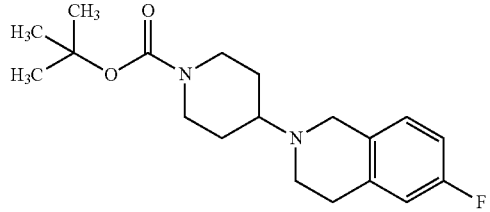 [SMILES: CC(C)(C)OC(=O)N1CCC(N2CCc3cc(F)ccc3C2)CC1]

1.73 g (8.66 mmol) of tert-butyl 4-oxopiperidine-1-carboxylate, 1.95 g (10.39 mmol) of 6-fluoro-1,2,3,4-tetrahydroisoquinoline hydrochloride and 3.02 ml (17.32 mmol) of N,N-diisopropylethylamine were dissolved in 50 ml of dichloromethane, and about 10 g of molecular sieve (4 Å) were added. The suspension was stirred at RT for 1 h. 2.75 g (12.99 mmol) of sodium triacetoxyborohydride were then added, and the mixture was stirred at RT for 18 h. For work-up, the mixture was diluted with about 50 ml of dichloromethane and washed twice with about 100 ml of saturated sodium bicarbonate solution. The combined aqueous phases were extracted once with about 50 ml of dichloromethane. The mixture was extracted with about 500 ml of ethyl acetate. The organic phase was washed with a further 500 ml of saturated sodium bicarbonate solution and with 200 ml of saturated sodium chloride solution. The combined organic phases were then dried over sodium sulphate, filtered and concentrated. The resulting residue was purified by chromatography on silica gel (elution with cyclohexane/ethyl acetate 2:1-1:1). This gave 2.73 g (94% of theory) of the target product.

LC-MS [Method 1]: $R_t$=0.70 min; MS (ESIpos): m/z=335 (M+H)$^+$

Example 4A

6-Fluoro-2-(piperidin-4-yl)-1,2,3,4-tetrahydroisoquinoline hydrochloride

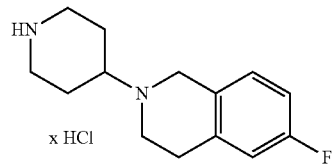 [SMILES: Fc1ccc2c(c1)CCN(C1CCNCC1)C2]

2.73 g (8.16 mmol) of the compound from Example 3A were dissolved in about 60 ml of dichloromethane, and 10.2 ml (40.82 mmol) of 4M hydrogen chloride in dioxane were added. The mixture was stirred at RT for about another 20 h, and about 100 ml of diethyl ether were then added. The resulting precipitate was filtered off with suction, washed with diethyl ether and dried under HV. This gave 2.24 g (89% of theory) of the target product as a white solid.

LC-MS MS [Method 8]: $R_t$=2.20 min; MS (ESIpos): m/z=235 (M+H)$^+$ $^1$H-NMR (400 MHz, DMSO-d$_6$): δ [ppm]=1.99-2.15 (m, 2H), 2.28-2.42 (m, 2H), 2.85-3.11 (m, 3H), 3.50-3.62 (m, 1H), 3.24-3.48 (m, 3H), 3.50-3.72 (m, 2H), 4.30-4.50 (m, 2H), 7.10-7.19 (m, 2H), 7.25-7.34 (m, 1H), 9.04 (s br, 1H), 9.24 (s br, 1H), 11.65 (s br, 1H).

Example 5A tert-Butyl 4-(6-methoxy-3,4-dihydroisoquinolin-2(1H)-yl)piperidine-1-carboxylate

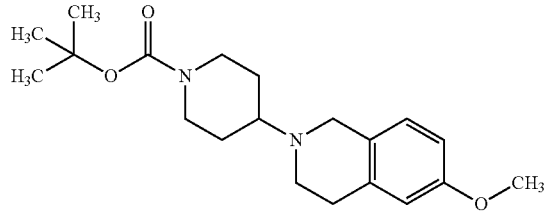 [SMILES: COc1ccc2c(c1)CCN(C1CCN(C(=O)OC(C)(C)C)CC1)C2]

Analogously to the compound from Example 3A, 2.59 g (13.02 mmol) of tert-butyl 4-oxopiperidine-1-carboxylate and 2.55 g (15.62 mmol) of 6-methoxy-1,2,3,4-tetrahydroquinoline were reacted with 4.14 g (19.53 mmol) of sodium triacetoxyborohydride. This gave 4.28 g (91% of theory) of the target product.

LC-MS [Method 1]: $R_t$=0.65 min; MS (ESIpos): m/z=347 (M+H)$^+$

Example 6A

6-Methoxy-2-(piperidin-4-yl)-1,2,3,4-tetrahydroisoquinoline hydrochloride

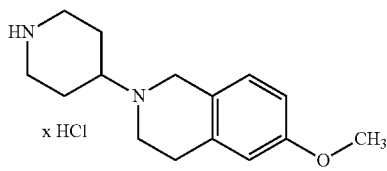 [SMILES: COc1ccc2c(c1)CCN(C1CCNCC1)C2]

Analogously to the compound from Example 4A, 4.28 g (11.86 mmol) of the compound from Example 9A were reacted with 17.79 mg (71.15 mmol) of 4M hydrogen chloride in dioxane. This gave 3.50 g (92% of theory) of the target product as a white solid.

LC-MS MS [Method 8]: $R_t$=2.62 min; MS (ESIpos): m/z=247 (M+H)$^+$ $^1$H-NMR (400 MHz, DMSO-$d_6$): δ [ppm]=1.97-2.13 (m, 2H), 2.27-2.41 (m, 2H), 2.85-3.06 (m, 3H), 3.11-3.49 (m, 4H), 3.49-3.71 (m, 2H), 3.75 (s, 3H), 4.26-4.43 (m, 2H), 6.81-6.89 (m, 2H), 7.15 (d, 1H), 8.88-9.20 (m, 2H), 11.31 (br. s, 1H).

Example 7A

6-[(2-Methoxyethyl)amino]nicotinic acid

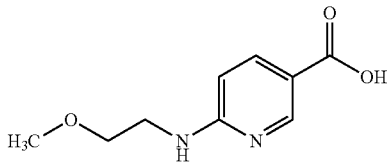

5.00 g (31.7 mmol) of 6-chloronicotinic acid, 27.6 ml (317 mmol) of 2-methoxyethylamine and 35 ml of 2-propanol were, divided into 5 portions, heated in the microwave at 180° C. for 1 h. After cooling to RT, the batches were combined and extracted with 500 ml of tert-butyl methyl ether and filtered off. The solid was taken up in 30 ml of water and acidified to pH 4 using 10% strength acetic acid and the resulting precipitate was filtered off with suction, washed with tert-butyl methyl ether and dried under HV, giving 2.20 g (35% of theory) of the title compound. Concentration of the filtrate to about ⅓ of the solvent volume gave, by crystallization, a further 1.00 g (16% of theory) of the title compound.

$^1$H-NMR (400 MHz, DMSO-$d_6$): δ [ppm]=2.81 (td, 2H), 3.40 (td, 2H), 3.45 (br. s., 3H), 6.41-6.52 (m, 1H), 7.07 (br. s., 1H), 7.76 (d, 1H), 8.49 (s, 1H).

Example 8A 6-(Morpholin-4-yl)nicotinic acid

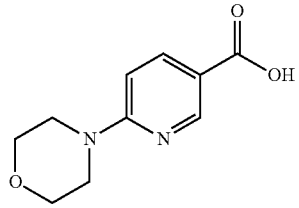 [SMILES: O=C(O)c1ccc(N2CCOCC2)nc1]

A mixture of 5.00 g (31.7 mmol) of 6-chloronicotinic acid and 27.7 ml (317 mmol) of morpholine was heated under reflux for 18 h. After cooling to RT, the mixture was extracted with tert-butyl methyl ether and filtered off. The solid was taken up in a little water and acidified to pH 4 using 10% strength acetic acid and the resulting precipitate was filtered off with suction, washed with tert-butyl methyl ether and dried in a vacuum drying cabinet, giving 5.94 g (85% of theory) of the title compound.

LC-MS [Method 8]: $R_t$=1.35 min; MS (ESIpos): m/z=209 (M+H)$^+$ $^1$H-NMR (400 MHz, DMSO-$d_6$): δ [ppm]=3.55-3.63 (m, 4H), 3.64-3.73 (m, 4H), 6.86 (d, 1H), 7.95 (dd, 1H), 8.64 (d, 1H), 11.53-13.28 (m, 1H).

Example 9A

[4-(3,4-Dihydroisoquinolin-2(1H)-yl)piperidin-1-yl](6-fluoropyridin-3-yl)methanone

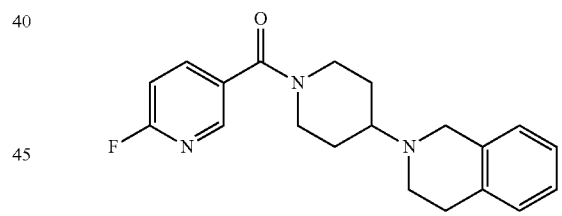

13.8 ml (79 mmol) of N,N-diisopropylethylamine were added to a mixture of 2.23 g (15.8 mmol) of 6-fluoronicotinic acid and 4.00 g (15.8 mmol) of the compound from Example 2A in 100 ml of acetonitrile. 11.1 ml (19 mmol) of T3P (50% by weight solution in ethyl acetate) were then added dropwise, and the mixture was stirred at RT for 18 h. For work-up, 50 ml of saturated sodium bicarbonate solution were added, and the mixture was stirred for 10 min, then diluted with water and extracted with ethyl acetate. The organic phase was dried over magnesium sulphate, filtered and concentrated. This gave 3.64 g (66% of theory) of the title compound.

LC-MS [Method 8]: $R_t$=2.50 min; MS (ESIpos): m/z=340 (M+H)$^+$ $^1$H-NMR (400 MHz, DMSO-$d_6$): δ [ppm]=1.47-1.63 (m, 2H), 1.70-1.98 (m, 2H), 2.65-6.96 (m, 6H), 3.00-3.24 (m, 1H), 3.50-3.67 (m, 1H), 3.71 (s, 2H), 4.33-4.62 (m, 1H), 6.97-7.14 (m, 4H), 7.27 (dd, 1H), 8.07 (td, 1H), 8.34 (d, 1H).

Example 10A

[4-(6-Fluoro-3,4-dihydroisoquinolin-2(1H)-yl)piperidin-1-yl](6-fluoropyridin-3-yl)methanone

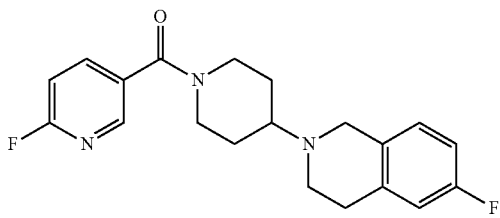 [SMILES: O=C(c1ccc(F)nc1)N1CCC(N2CCc3cc(F)ccc3C2)CC1]

1.7 ml (9.9 mmol) of N,N-diisopropylethylamine were added to a mixture of 398 mg (2.8 mmol) of 6-fluoronicotinic acid and 867 mg (15.8 mmol) of the compound from Example 4A in 40 ml of acetonitrile. 2.0 ml (3.4 mmol) of T3P (50% by weight solution in ethyl acetate) were then added dropwise, and the mixture was stirred at RT for 18 h. For work-up, saturated sodium bicarbonate solution was added and the mixture was stirred for 10 min and then diluted with water and extracted with ethyl acetate. The organic phase was dried over magnesium sulphate, filtered and concentrated, giving 724 mg (71% of theory) of the title compound.

LC-MS [Method 1]: $R_t$=0.48 min; MS (ESIpos): m/z=358 (M+H)$^+$ $^1$H-NMR (400 MHz, DMSO-d$_6$): δ [ppm]=1.34-1.62 (m, 2H), 1.66-2.05 (m, 2H), 2.63-2.95 (m, 8H), 3.02-3.20 (m, 1H), 3.52-3.62 (m, 1H), 3.64-3.73 (m, 2H), 4.30-4.76 (m, 1H), 6.84-6.96 (m, 2H), 7.02-7.15 (m, 1H), 7.22-7.34 (m, 1H), 7.98-8.12 (m, 1H), 8.23-8.40 (m, 1H).

Example 11A (6-Fluoropyridin-3-yl) [4-(6-methoxy-3,4-dihydroisoquinolin-2(1H)-yl)piperidin-1-yl]methanone

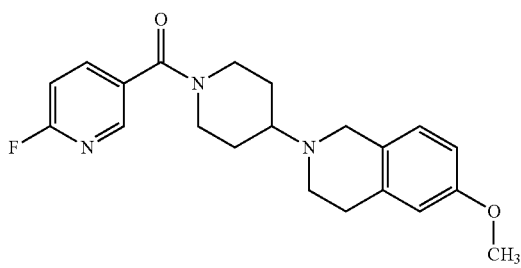 [SMILES: COc1ccc2c(c1)CCN(C1CCN(C(=O)c3ccc(F)nc3)CC1)C2]

1.6 ml (9.4 mmol) of N,N-diisopropylethylamine were added to a mixture of 377 mg (2.7 mmol) of 6-fluoronicotinic acid and 853 mg (2.7 mmol) of the compound from Example 6A in 30 ml of acetonitrile. 1.9 ml (3.2 mmol) of T3P (50% by weight solution in ethyl acetate) were then added dropwise, and the mixture was stirred at RT for 18 h. For work-up, saturated sodium bicarbonate solution was added and the mixture was stirred for 10 min and then diluted with water and extracted with ethyl acetate. The organic phase was dried over magnesium sulphate, filtered and concentrated. The product was then purified by preparative HPLC [method 9]. This gave 203 mg (21% of theory) of the title compound.

LC-MS [Method 1]: $R_t$=0.52 min; MS (ESIpos): m/z=370 (M+H)$^+$ $^1$H-NMR (400 MHz, DMSO-d$_6$): δ [ppm]=1.44-1.60 (m, 2H), 1.70-1.97 (m, 2H), 2.74 (s, 5H), 2.79-2.96 (m, 1H), 3.01-3.21 (m, 1H), 3.63 (s, 3H), 3.69 (s, 3H), 4.40-4.63 (m, 1H), 6.65 (s, 2H), 6.87-7.04 (m, 1H), 7.16-7.36 (m, 1H), 7.95-8.17 (m, 1H), 8.28-8.43 (m, 1H).

Example 12A

Ethyl 6-(2-oxa-6-azaspiro[3.3]hept-6-yl)nicotinate

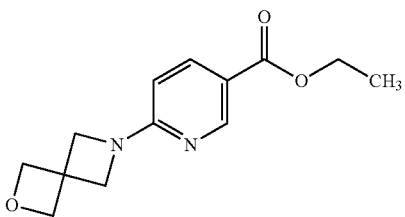 [SMILES: CCOC(=O)c1ccc(N2CC3(COC3)C2)nc1]

15 g (81 mmol) of ethyl 6-chloronicotinate were dissolved in 150 ml of acetonitrile, and 39 mg of potassium carbonate (283 mmol) were added. 23 g (121 mmol) of 2-oxa-6-azaspiro[3.3]heptane oxalate salt, prepared according to Angew. Chem. Int. Ed. 2008, 47, 4512-4515, were then added and the mixture was stirred at 60° C. for 18 h. The mixture was then stirred with water and extracted with ethyl acetate. The organic phase was washed with water, then dried over sodium sulphate, filtered off and concentrated. This gave 18 g (92% of theory) of the desired compound which was reacted further directly without further purification.

LC-MS [Method 1]: $R_t$=0.65 min; MS (ESIpos): m/z=248 (M+H)$^+$

Example 13A 6-(2-Oxa-6-azaspiro[3.3]hept-6-yl)nicotinic acid

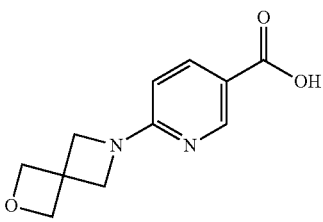 [SMILES: O=C(O)c1ccc(N2CC3(COC3)C2)nc1]

18.4 g (74 mmol) of the compound from Example 12A were initially charged in 150 ml of ethanol, 148 ml of 1 molar solution of sodium hydroxide were added and the mixture was stirred at RT for 5 h. The mixture was concentrated and then initially dissolved in about 150 ml of water and then adjusted to pH 5 with 1 molar hydrochloric acid. The precipitated product was filtered off and washed with water. This gave 12.6 g (77% of theory) of the title compound.

LC-MS [Method 7]: $R_t$=0.69 min; MS (ESIpos): m/z=221 (M+H)$^+$

Example 14A

Methyl-[6-(2,6-dimethyl)morpholin-4-yl]nicotinate (cis and trans isomer)

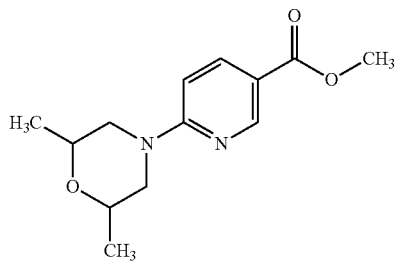

250 mg (1.5 mmol) of methyl-6-chloronicotinate were initially charged in 3 ml of acetonitrile, 705 mg (5.1 mmol) of potassium carbonate and 252 mg (2.2 mmol) of 2,6-dimethylmorpholine were added and the mixture was stirred at 60° C. for 20 h. Water was then added, and the mixture was extracted with ethyl acetate. The organic phase was dried over sodium sulphate, subsequently filtered off and then concentrated. The crude product was purified on silica gel (mobile phase: cyclohexane/ethyl acetate 8:1-5:1). This gave 226 mg (62% of theory) of cis isomer and 64 mg (18% of theory) of trans isomer.

cis Isomer: LC-MS [Method 1]: Rt=0.94 min; MS (ESIpos): m/z=251 (M+H)$^+$ trans Isomer: LC-MS [method 1]: Rt=0.89 min; MS (ESIpos): m/z=251 (M+H)$^+$

Example 15A 6-(2,6-Dimethylmorpholin-4-yl)nicotinic acid (cis isomer)

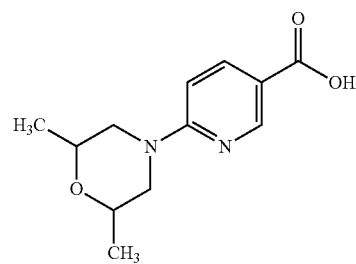 [SMILES: CC1CN(c2ccc(C(=O)O)cn2)CC(C)O1]

124 mg (0.3 mmol) of the compound from Example 14A—cis isomer—were initially charged in 2 ml of methanol/THF 1/1, and 0.5 ml of a 2 molar solution of sodium hydroxide was then added. The mixture was stirred at 70° C. for 1 h. The mixture was concentrated and taken up in water. The mixture was subsequently acidified with 1 molar aqueous hydrochloric acid and extracted twice with ethyl acetate. The combined organic phases were dried over sodium sulphate, filtered and then concentrated. This gave 106 mg (91% of theory) of the target compound which was reacted further without further purification.

LC-MS [Method 1]: R$_t$=0.72 min; MS (ESIpos): m/z=238 (M+H)$^+$

Example 16A 6-(2,6-Dimethylmorpholin-4-yl]nicotinic acid (trans isomer)

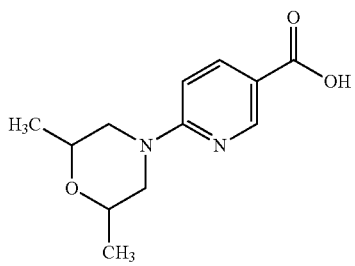 [SMILES: CC1CN(c2ccc(C(=O)O)cn2)CC(C)O1]

64 mg (0.3 mmol) of the compound from Example 14A—trans isomer—were initially charged in 2 ml of methanol/THF 1/1, and 0.3 ml of a 2 molar solution of sodium hydroxide was then added. The mixture was stirred at 70° C. for 1 h. The mixture was concentrated and taken up in water. The mixture was subsequently acidified with 1 molar aqueous hydrochloric acid and extracted twice with ethyl acetate. The combined organic phases were dried over sodium sulphate, filtered and then concentrated. This gave 23 mg (31% of theory) of the target compound which was reacted further without further purification.

LC-MS [Method 1]: R$_t$=0.62 min; MS (ESIpos): m/z=238 (M+H)$^+$

Example 17A

Methyl 6-(2,2-dimethylmorpholin-4-yl)nicotinate

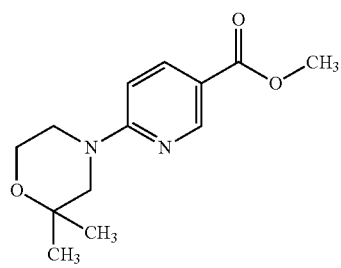 [SMILES: COC(=O)c1ccc(N2CCOC(C)(C)C2)nc1]

250 mg (1.5 mmol) of methyl 6-chloronicotinate were initially charged in 3 ml of acetonitrile, 1007 mg (7.3 mmol) of potassium carbonate and 331 mg (2.2 mmol) of 2,2-dimethylmorpholine hydrochloride were added and the mixture was stirred at 60° C. for 20 h. The mixture was then mixed with water and extracted with ethyl acetate. The organic phase was dried over sodium sulphate, filtered and concentrated. The crude product was purified on silica gel (mobile phase: cyclohexane/ethyl acetate 8:1-5:1). This gave 179 mg of product (49% of theory).

LC-MS [Method 1]: R$_t$=0.86 min; MS (ESIpos): m/z=251 (M+H)$^+$

Example 18A 6-(2,2-Dimethylmorpholin-4-yl)nicotinic acid

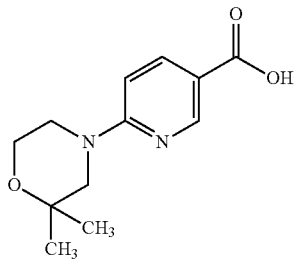 [SMILES: CC1(C)CN(c2ccc(C(=O)O)cn2)CCO1]

179 mg (0.72 mmol) of the compound from Example 17A were initially charged in 2 ml of methanol/THF 1/1, and 0.72 ml of 2 molar sodium hydroxide solution was then added. The mixture was stirred at 70° C. for 1 h. The mixture was concentrated and taken up in water. The mixture was subsequently acidified with 1 molar aqueous hydrochloric acid and extracted twice with ethyl acetate. The combined organic phases were dried over sodium sulphate, filtered and concentrated. This gave 100 mg (60% of theory) of the target compound, which was reacted further without further purification.

LC-MS [Method 1]: Rt=0.62 min; MS (ESIpos): m/z=237 (M+H)$^+$

Example 19A

Methyl 6-[2-(trifluoromethyl)morpholin-4-yl]nicotinate

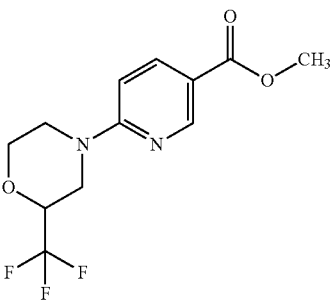 [SMILES: COC(=O)c1ccc(N2CCOC(C(F)(F)F)C2)nc1]

250 mg (1.5 mmol) of methyl 6-chloronicotinate were initially charged in 3 ml of acetonitrile, 705 mg (5.1 mmol) of potassium carbonate and 331 mg (2.2 mmol) of 2-(trifluoromethyl)morpholine hydrochloride (1:1) were added and the mixture was stirred at 60° C. for 20 h. Water was then added, and the mixture was extracted with ethyl acetate. The organic phase was dried over sodium sulphate, filtered and concentrated. The crude product was purified on silica gel (mobile phase: cyclohexane/ethyl acetate 8:1-5:1). This gave 47 mg (11% of theory) of product.

LC-MS [Method 1]: Rt=1.02 min; MS (ESIpos): m/z=291 (M+H)$^+$

Example 20A

6-[2-(Trifluoromethyl)morpholin-4-yl]nicotinic acid

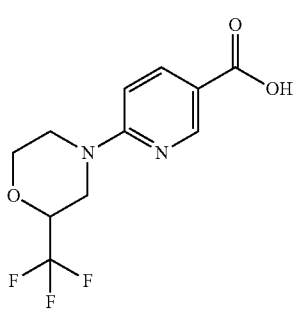 [SMILES: O=C(O)c1ccc(N2CCOC(C(F)(F)F)C2)nc1]

46 mg (0.16 mmol) of the compound from Example 19A were initially charged in 2 ml of methanol/THF 1/1, and 0.16 ml of 2 molar sodium hydroxide solution was then added. The mixture was stirred at 70° C. for 1 h. The mixture was concentrated and taken up in water. The mixture was then acidified with 1 molar aqueous hydrochloric acid and extracted twice with ethyl acetate. The combined organic phases were dried over sodium sulphate, filtered and concentrated. This gave 45 mg (44% of theory) of the target compound which were reacted further without further purification.

LC-MS [Method 1]: Rt=0.83 min; MS (ESIpos): m/z=277 (M+H)$^+$

Example 21A

Methyl 6-(2-thia-6-azaspiro[3.3]hept-6-yl)nicotinate

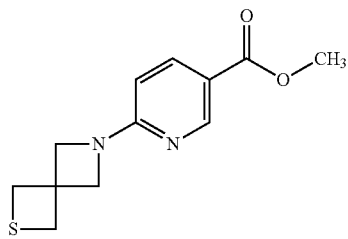 [SMILES: COC(=O)c1ccc(N2CC3(CSC3)C2)nc1]

250 mg (1.5 mmol) of methyl 6-chloronicotinate were initially charged in 3 ml of acetonitrile, 705 mg (5.1 mmol) of potassium carbonate and 173 mg (1.5 mmol) of 2-thia-6-azaspiro[3.3]heptane were added and the mixture was stirred at 60° C. for 20 h. Water was then added, and the mixture was extracted with ethyl acetate. The organic phase was dried over sodium sulphate, filtered and concentrated. The crude product was purified on silica gel (mobile phase: cyclohexane/ethyl acetate 8:1-5:1). This gave 307 mg (84% of theory) of the title compound, which were directly reacted further.

LC-MS [Method 1]: Rt=0.80 min; MS (ESIpos): m/z=251 (M+H)$^+$

Example 22A

Methyl 6-(2,2-dioxido-2-thia-6-azaspiro[3.3]hept-6-yl)nicotinate

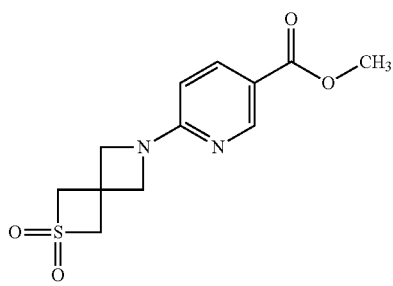 [SMILES: COC(=O)c1ccc(N2CC3(C2)CS(=O)(=O)C3)nc1]

0.25 ml of water was added to 1.2 g (5.6 mmol) of aluminium oxide, followed by 7 ml of dichloromethane. 0.74 g (1.2 mmol) of Oxone (potassium peroxomonosulphate triple salt) and 0.30 g (1.2 mmol) of the compound from Example 21A were added to the suspension. The suspension was then stirred under reflux for 1 h. The mixture was cooled to RT, filtered and concentrated. The entire procedure was repeated once more using the crude mixture obtained. After 1 h of stirring under reflux, the mixture was filtered again and washed thoroughly with dichloromethane. The filtrate gave, after concentration and drying under HV, a total of 182 mg (44% of theory) of the target compound with a purity of 80%, which were directly reacted further.

LC-MS [Method 1]: Rt=0.56 min; MS (ESIpos): m/z=282 (M+H)+

Example 23A 6-(2,2-Dioxido-2-thia-6-azaspiro[3.3]hept-6-yl)nicotinic acid

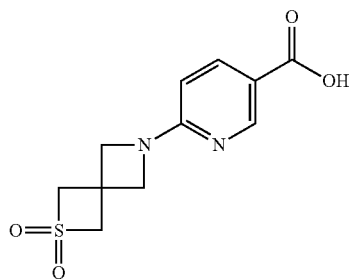 [SMILES: O=C(O)c1ccc(N2CC3(C2)CS(=O)(=O)C3)nc1]

182 mg (0.65 mmol) of the compound from Example 22A were initially charged in 2 ml of methanol/THF 1/1, and 0.65 ml of a 2 molar solution of sodium hydroxide was then added. The mixture was stirred at 70° C. for 1 h. The mixture was concentrated and taken up in water. The mixture was subsequently acidified with 1 molar aqueous hydrochloric acid and extracted twice with ethyl acetate. The combined organic phases were dried over sodium sulphate, filtered and concentrated. This gave 138 mg (80% of theory) of the title compound which was reacted further without further purification.

LC-MS [Method 1]: MS (ESIpos): m/z=268 (M+H)+

WORKING EXAMPLES

Example 1

[4-(3,4-Dihydroisoquinolin-2-(1H)-yl)piperidin-1-yl]{6-[(2-methoxyethyl)amino]pyridin-3-yl}-methanone

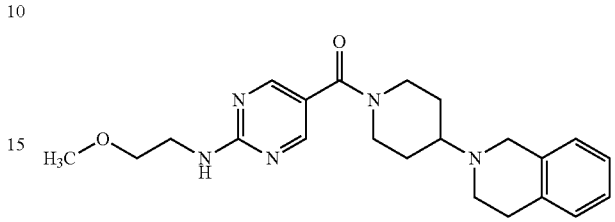

0.44 ml (2.5 mmol) of N,N-diisopropylethylamine and 0.39 ml (0.66 mmol) of T3P (50% by weight strength solution in ethyl acetate) were added to a mixture of 100 mg (0.51 mmol) of the compound from Example 7A and 154 mg (0.61 mmol) of the compound from Example 2A in 3.0 ml of acetonitrile, and the mixture was then stirred at RT for 18 h. For work-up, 2 ml of saturated sodium bicarbonate solution were added, the mixture was stirred for 15 min, filtered through an Extrelut cartridge and eluted with ethyl acetate and the filtrate was concentrated. The resulting crude product was purified by preparative HPLC [Method 9], giving 83 mg (39% of theory) of the title compound.

LC-MS [Method 8]: R$_t$=2.40 min; MS (ESIpos): m/z=395 (M+H)+

$^1$H-NMR (400 MHz, DMSO-d$_6$): δ [ppm]=1.44-1.56 (m, 2H), 1.77-1.90 (m, 2H), 2.61-2.81 (m, 5H), 2.81-3.08 (m, 2H), 3.27 (s, 3H), 3.44-3.47 (m, 4H), 3.68-3.72 (m, 2H), 3.81-4.45 (m, 2H), 6.51 (d, 1H), 7.00-7.13 (m, 5H), 7.43 (dd, 1H), 8.08 (d, 1H).

Example 2

[4-(7-Fluoro-3,4-dihydroisoquinolin-2(1H)-yl)piperidin-1-yl]{6-[(2-methoxyethyl)amino]pyridin-3-yl}methanone

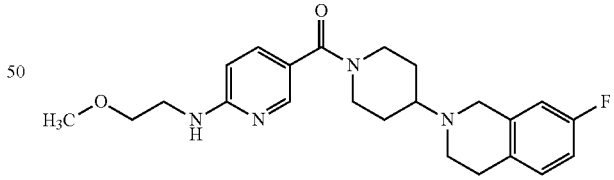

0.444 ml (2.5 mmol) of N,N-diisopropylethylamine and 0.387 ml (0.66 mmol) of T3P (50% by weight strength solution in ethyl acetate) were added to a mixture of 100 mg (0.510 mmol) of the compound from Example 7A and 188 mg (0.612 mmol) of the compound from Example 4A in 3.0 ml of acetonitrile, and the mixture was then stirred at RT for 18 h. For work-up, 2 ml of saturated sodium bicarbonate solution were added, the mixture was stirred for 15 min, filtered through an Extrelut cartridge and eluted with ethyl acetate and the filtrate was concentrated. The resulting crude product was purified by preparative HPLC [Method 9], giving 64 mg (30% of theory) of the title compound.

LC-MS [Method 2]: $R_t$=0.35 min; MS (ESIpos): m/z=413 (M+H)$^+$ $^1$H-NMR (400 MHz, DMSO-d$_6$): δ [ppm]=1.40-1.56 (m, 2H), 1.78-1.88 (m, 2H), 2.61-2.80 (m, 5H), 2.80-3.06 (m, 2H), 3.27 (s, 3H), 3.42-3.48 (m, 4H), 3.70 (s, 2H), 3.78-4.41 (m, 2H), 6.51 (d, 1H), 6.85-6.97 (m, 2H), 7.00-7.07 (m, 1H), 7.07-7.14 (m, 1H), 7.43 (dd, 1H), 8.07 (d, 1H).

Example 3

[4-(3,4-Dihydroisoquinolin-2(1H)-yl)piperidin-1-yl][6-(morpholin-4-yl)pyridin-3-yl]methanone

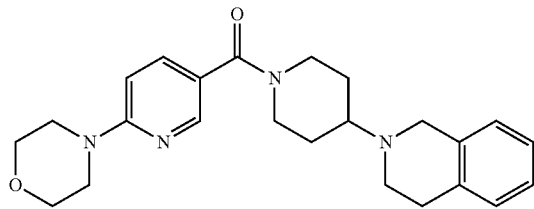 [SMILES: O=C(c1ccc(N2CCOCC2)nc1)N1CCC(N2CCc3ccccc3C2)CC1]

0.314 ml (1.8 mmol) of N,N-diisopropylethylamine and 0.252 ml (0.432 mmol) of T3P (50% by weight strength solution in ethyl acetate) were added to a mixture of 75 mg (0.360 mmol) of the compound from Example 8A and 109 mg (0.432 mmol) of the compound from Example 2A in 2.5 ml of acetonitrile, and the mixture was then stirred at RT for 18 h. For work-up, 2 ml of a saturated sodium bicarbonate solution were added, the mixture was stirred for 15 min, filtered through an Extrelut cartridge and eluted with ethyl acetate and the filtrate was concentrated. The resulting crude product was purified by preparative HPLC [Method 9], giving 104 mg (70% of theory) of the title compound.

LC-MS [Method 8]: $R_t$=2.51 min; MS (ESIpos): m/z=407 (M+H)$^+$ $^1$H-NMR (400 MHz, DMSO-d$_6$): δ [ppm]=1.44-1.60 (m, 2H), 1.75-1.95 (m, 2H), 2.64-2.74 (m, 1H), 2.77 (s, 4H), 2.83-3.08 (m, 2H), 3.48-3.56 (m, 4H), 3.65-3.74 (m, 6H), 3.75-4.52 (m, 2H), 6.85 (d, 1H), 7.00-7.14 (m, 4H), 7.62 (dd, 1H), 8.21 (d, 1H).

Example 4

[4-(3,4-Dihydroisoquinolin-2(1H)-yl)piperidin-1-yl][6-(1,1-dioxidothiomorpholin-4-yl)pyridin-3-yl]methanone

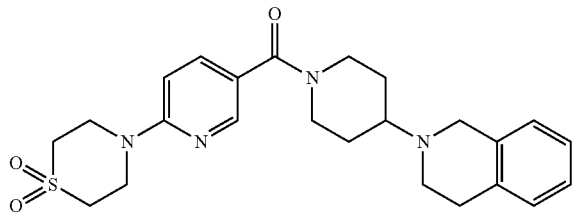 [SMILES: O=C(c1ccc(N2CCS(=O)(=O)CC2)nc1)N1CCC(N2CCc3ccccc3C2)CC1]

A mixture of 150 mg (0.40 mmol) of the compound from Example 9A, 108 mg (0.80 mmol) of thiomorpholine 1,1-dioxide and 0.35 ml (2.0 mmol) of N,N-diisopropylethylamine in 1.4 ml of N-methyl-2-pyrrolidone was heated in the microwave at 220° C. for 2.5 h. After cooling to RT, water was added and the mixture was extracted twice with ethyl acetate. The combined organic phases were washed with saturated sodium chloride solution, dried over magnesium sulphate, filtered and concentrated. The resulting residue was purified by preparative HPLC [Method 9], giving 86.0 mg (46% of theory) of the title compound.

LC-MS [Method 8]: $R_t$=2.41 min; MS (ESIpos): m/z=455 (M+H)$^+$ $^1$H-NMR (400 MHz, DMSO-d$_6$): δ [ppm]=1.43-1.58 (m, 2H), 1.76-1.92 (m, 2H), 2.65-2.74 (m, 1H), 2.77 (s, 4H), 2.83-3.08 (m, 2H), 3.10-3.20 (m, 4H), 3.71 (s, 2H), 3.78-4.58 (m, 6H), 7.00-7.13 (m, 5H), 7.66 (dd, 1H), 8.24 (d, 1H).

Example 5

[4-(3,4-Dihydroisoquinolin-2(1H)-yl)piperidin-1-yl]{6-[(2R)-2-(methoxymethyl)pyrrolidin-1-yl]pyridin-3-yl}methanone

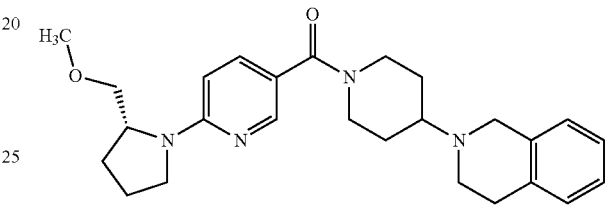

A mixture of 100 mg (0.23 mmol) of the compound from Example 9A, 102 mg (0.884 mmol) of (2R)-2-(methoxymethyl)pyrrolidine and 0.348 ml (2.0 mmol) of N,N-diisopropylethylamine in 1.4 ml of N-methyl-2-pyrrolidone was heated in the microwave at 180° C. for 1.5 h. After cooling to RT, the reaction mixture was purified directly by preparative HPLC [Method 9], giving 110 mg (80% of theory) of the title compound.

LC-MS [Method 8]: $R_t$=2.77 min; MS (ESIpos): m/z=435 (M+H)$^+$ $^1$H-NMR (400 MHz, DMSO-d$_6$): δ [ppm]=1.43-1.59 (m, 2H), 1.79-2.11 (m, 6H), 2.63-2.74 (m, 1H), 2.77 (s, 4H), 2.82-3.05 (m, 2H), 3.21-3.30 (m, 5H), 3.42-3.53 (m, 2H), 3.71 (s, 2H), 3.77-4.58 (m, 3H), 6.51 (d, 1H), 7.00-7.12 (m, 4H), 7.57 (dd, 1H), 8.18 (d, 1H).

Example 6

1-(5-{[4-(3,4-Dihydroisoquinolin-2(1H)-yl)piperidin-1-yl]carbonyl}pyridin-2-yl)-D-proline

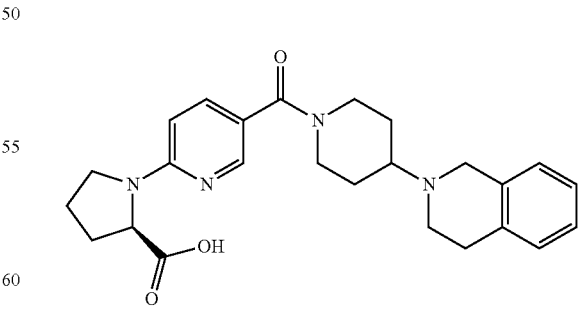

A mixture of 300 mg (0.88 mmol) of the compound from Example 9A, 203 mg (1.77 mmol) of D-proline and 0.77 ml (4.4 mmol) of N,N-diisopropylethylamine in 3.0 ml of 2-propanol was heated in the microwave at 120° C. for 5 h. After cooling to RT, the reaction mixture was concentrated and then purified by preparative HPLC [Method 10], giving 265 mg (69% of theory) of the title compound.

LC-MS [Method 1]: $R_t$=0.47 min; MS (ESIpos): m/z=435 (M+H)⁺

¹H-NMR (400 MHz, DMSO-d₆): δ [ppm]=1.44-1.57 (m, 2H), 1.78-1.89 (m, 2H), 1.92-2.08 (m, 3H), 2.18-2.32 (m, 1H), 2.63-2.74 (m, 1H), 2.77 (s, 4H), 2.81-3.07 (m, 2H), 3.49-3.59 (m, 1H), 3.71 (s, 2H), 3.77-4.36 (m, 2H), 4.39-4.48 (m, 1H), 6.48 (d, 1H), 6.99-7.13 (m, 4H), 7.59 (dd, 1H), 8.14 (d, 1H).

Example 7

[4-(3,4-Dihydroisoquinolin-2(1H)-yl)piperidin-1-yl] (6-{[(2S)-1-hydroxybutan-2-yl]amino}pyridin-3-yl) methanone

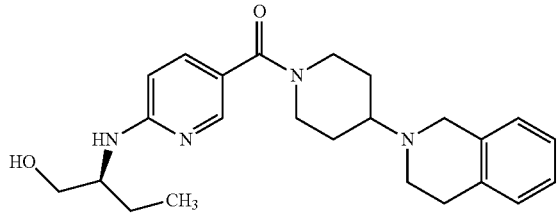 [SMILES: CC[C@@H](CO)Nc1ccc(C(=O)N2CCC(N3CCc4ccccc4C3)CC2)cn1]

A mixture of 100 mg (0.30 mmol) of the compound from Example 9A, 53 mg (0.59 mmol) of (S)-(+)-2-amino-1-butanol and 0.257 ml (1.5 mmol) of N,N-diisopropylethylamine in 1.0 ml of 2-propanol was heated in the microwave at 180° C. for 1 h and then at 200° C. for 3 h. After cooling to RT, the reaction mixture was concentrated and the crude product was purified chromatographically on silica gel (elution with dichloromethane/methanol 98:2-80:20). The resulting product was re-purified by preparative HPLC [Method 11], giving 37 mg (22% of theory) of the title compound.

LC-MS [Method 8]: $R_t$=2.41 min; MS (ESIpos): m/z=409 (M+H)⁺

¹H-NMR (400 MHz, DMSO-d₆): δ [ppm]=0.88 (t, 3H), 1.35-1.57 (m, 3H), 1.60-1.73 (m, 1H), 1.79-1.89 (m, 2H), 2.63-2.72 (m, 1H), 2.77 (s, 4H), 2.85-3.01 (m, 2H), 3.33-3.38 (m, 1H), 3.42-3.50 (m, 1H), 3.70 (s, 2H), 3.78-3.91 (m, 1H), 3.96-4.27 (m, 2H), 4.59-4.69 (m, 1H), 6.51 (d, 1H), 6.67 (d, 1H), 7.01-7.12 (m, 4H), 7.41 (dd, 1H), 8.05 (d, 1H).

Example 8

[4-(6-Fluoro-3,4-dihydroisoquinolin-2(1H)-yl)piperidin-1-yl][6-(3-methoxypyrrolidin-1-yl)pyridin-3-yl]methanone

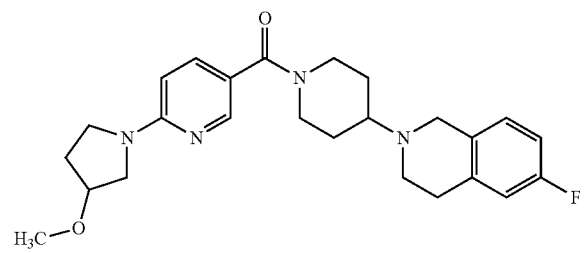 [SMILES: COC1CCN(c2ccc(C(=O)N3CCC(N4CCc5cc(F)ccc5C4)CC3)cn2)C1]

70 mg (0.20 mmol) of the compound from Example 10A and 54 mg of 3-methoxypyrrolidine hydrochloride (0.40 mmol) were dissolved in 0.8 ml of N-methyl-2-pyrrolidone and 0.2 ml of N,N-diisopropylethylamine (0.98 mmol), and the mixture was stirred in the microwave at 180° C. for 45 min. The mixture was then diluted with methanol and purified by preparative HPLC [Method 9]. This gave 63 mg (73% of theory) of the title compound.

LC-MS [Method 1]: $R_t$=0.44 min; MS (ESIpos): m/z=439 (M+H)⁺

¹H-NMR (400 MHz, DMSO-d₆): δ [ppm]=0.98-1.12 (m, 1H), 1.31-1.60 (m, 1H), 1.75-1.90 (m, 1H), 1.96-2.17 (m, 1H), 2.61-2.82 (m, 6H), 2.84-3.03 (m, 2H), 3.27 (s, 2H), 3.34-3.43 (m, 1H), 3.51 (d, 3H), 3.67 (s, 2H), 3.93-4.32 (m, 3H), 6.46 (d, 1H), 6.91 (d, 2H), 7.02-7.11 (m, 1H), 7.47-7.61 (m, 1H), 8.17 (d, 1H).

Example 9

[4-(6-Methoxy-3,4-dihydroisoquinolin-2(1H)-yl) piperidin-1-yl][6-(3-methoxypyrrolidin-1-yl)pyridin-3-yl]methanone

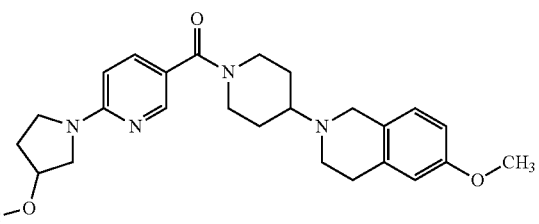

80 mg (0.20 mmol) of the compound from Example 11a and 68 mg of 3-methoxypyrrolidine hydrochloride (0.49 mmol) were dissolved in 0.8 ml of N-methyl-2-pyrrolidone and 0.2 ml of N,N-diisopropylethylamine (1.18 mmol, 6.0 eq.), and the mixture was stirred in the microwave at 180° C. for 45 min. The mixture was then diluted with methanol and purified by preparative HPLC [Method 9]. This gave 67 mg (75% of theory) of the title compound.

LC-MS [Method 1]: $R_t$=0.45 min; MS (ESIpos): m/z=451 (M+H)⁺

¹H-NMR (400 MHz, DMSO-d₆): δ [ppm]=1.35-1.61 (m, 2H), 1.74-1.90 (m, 2H), 1.96-2.12 (m, 2H), 2.61-2.70 (m, 1H), 2.74 (s, 4H), 2.83-3.02 (m, 2H), 3.27 (s, 3H), 3.33-3.44 (m, 1H), 3.51 (d, 3H), 3.63 (s, 2H), 3.69 (s, 3H), 3.93-4.34 (m, 3H), 6.35-6.53 (m, 1H), 6.64 (s, 2H), 6.88-7.00 (m, 1H), 7.49-7.62 (m, 1H), 8.01-8.27 (m, 1H).

Example 10

[4-(3,4-Dihydroisoquinolin-2(1H)-yl)piperidin-1-yl] [6-(2-oxa-6-azaspiro[3.3]hept-6-yl)pyridin-3-yl] methanone 12.6 g (57.2 mmol) of the compound in Example 13A and 16.5 mg (57.2 mmol) of the compound from Example 2A were dissolved in 250 ml of acetonitrile, and 50 ml of N,N-diisopropylethylamine (286.1 mmol) were added. 41 ml of T3P (50% strength solution in ethyl acetate) (68.7 mmol) were then added dropwise, and the mixture was stirred at RT for 18 h. After concentration of the solvent, saturated aqueous sodium bicarbonate solution was added to the residue. After 10 min, the mixture was diluted with water and extracted twice with ethyl acetate. The combined organic phases were dried over sodium sulphate and then filtered, and the filtrate was concentrated. The residue was extracted with 30 ml of methanol and then diluted with 250 ml of diethyl ether. After 30 min, the precipitated product was filtered off and washed with a mixture of methanol and diethyl ether (4/1). This gave 15.7 g of product (66% of theory).

LC-MS [Method 7]: $R_t$=2.01 min; MS (ESIpos): m/z=420 (M+H)$^+$ $^1$H-NMR (400 MHz, DMSO-d$_6$): δ [ppm]=1.31-1.61 (m, 2H), 1.73-1.94 (m, 2H), 2.63-2.72 (m, 1H), 2.77 (s, 4H), 2.83-3.07 (m, 2H), 3.70 (s, 2H), 4.16 (s, 4H), 4.72 (s, 4H), 6.38 (d, 1H), 6.97-7.13 (m, 4H), 7.49-7.64 (m, 1H), 8.15 (d, 1H).

Example 11

[4-(3,4-Dihydroisoquinolin-2(1H)-yl)piperidin-1-yl] [6-(2,6-dimethylmorpholin-4-yl)pyridin-3-yl]methanone (cis isomer)

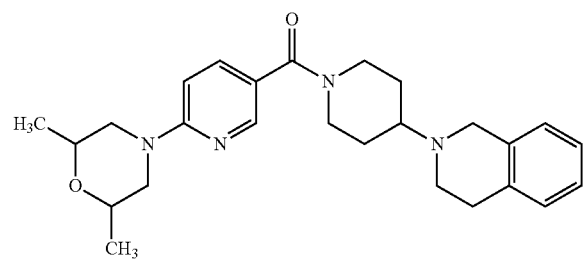 [SMILES: CC1CN(c2ccc(C(=O)N3CCC(N4CCc5ccccc5C4)CC3)cn2)CC(C)O1]

173 mg (0.73 mmol) of the compound in Example 15A and 212 mg (0.73 mmol) of the compound from Example 2A were initially charged in 2 ml of acetonitrile, and 0.64 ml of N,N-diisopropylethylamine (3.66 mmol) was added. 0.52 ml of T3P (50% strength solution in ethyl acetate) (0.88 mmol) was then added dropwise, and the mixture was stirred at RT for 18 h. After concentration under reduced pressure, saturated aqueous sodium bicarbonate solution was added to the residue. After 10 min, the mixture was diluted with water and extracted twice with ethyl acetate. The combined organic phases were dried over sodium sulphate, filtered and concentrated. The crude product was purified by preparative HPLC [Method 9]. This gave 238 mg (75% of theory) of the target compound.

LC-MS [Method 1]: $R_t$=0.61 min; MS (ESIpos): m/z=435 (M+H)$^+$ $^1$H-NMR (400 MHz, DMSO-d$_6$): δ [ppm]=$^1$H-NMR (400 MHz, DMSO-d$_6$): δ [ppm]=1.16 (d, 6H), 1.50 (dd, 2H), 1.84 (d, 2H), 2.45 (dd, 2H), 2.69 (br. s., 1H), 2.77 (s, 5H), 2.82-3.09 (m, 2H), 3.59 (ddd, 2H), 3.70 (s, 2H), 4.22 (d, 2H), 6.86 (d, 1H), 6.97-7.13 (m, 4H), 7.61 (dd, 1H), 8.20 (d, 1H).

Example 12

[4-(3,4-Dihydroisoquinolin-2(1H)-yl)piperidin-1-yl] [6-(2,6-dimethylmorpholin-4-yl)pyridin-3-yl]methanone (trans isomer)

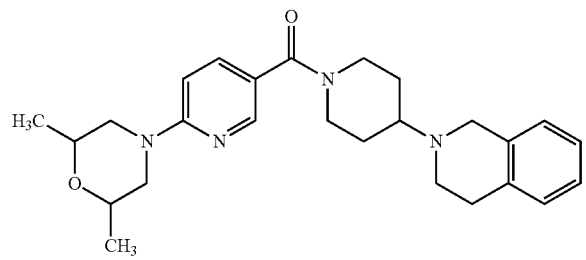 [SMILES: CC1CN(c2ccc(C(=O)N3CCC(N4CCc5ccccc5C4)CC3)cn2)CC(C)O1]

23 mg (0.10 mmol) of the compound from Example 16A and 28 mg (0.10 mmol) of the compound from Example 2A were initially charged in 2 ml of acetonitrile, and 0.09 ml of N,N-diisopropylethylamine (0.49 mmol) was added. 0.07 ml of T3P (50% strength solution in ethyl acetate) (0.12 mmol) was then added dropwise, and the mixture was stirred at RT for 18 h. After concentration under reduced pressure, saturated aqueous sodium bicarbonate solution was added to the residue. After 10 min, the mixture was diluted with water and extracted twice with ethyl acetate. The combined organic phases were dried over sodium sulphate, filtered and concentrated. The crude product was purified by preparative HPLC [Method 9]. This gave 16 mg (37% of theory) of the target compound.

LC-MS (MCW_SQ-HSST3): $R_t$=0.58 min; MS (ESIpos): m/z=435 (M+H)$^+$ $^1$H-NMR (400 MHz, DMSO-d$_6$): δ [ppm]=1.15 (d, 6H), 1.38-1.57 (m, 2H), 1.69-1.94 (m, 2H), 2.62-2.73 (m, 1H), 2.77 (s, 4H), 2.82-3.08 (m, 2H), 3.28 (dd, 2H), 3.61-3.74 (m, 4H), 4.01 (d, 3H), 6.83 (d, 1H), 6.94-7.16 (m, 4H), 7.43-7.67 (m, 1H), 8.18 (d, 1H).

Example 13

[4-(3,4-Dihydroisoquinolin-2(1H)-yl)piperidin-1-yl] [6-(2,2-dimethylmorpholin-4-yl)pyridin-3-yl]methanone

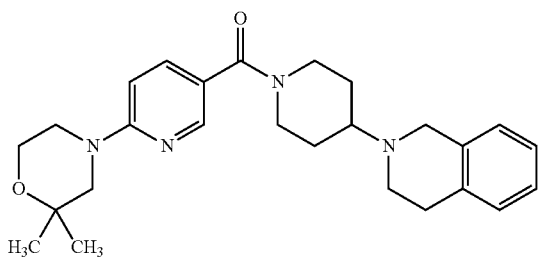 [SMILES: CC1(C)CN(c2ccc(C(=O)N3CCC(N4CCc5ccccc5C4)CC3)cn2)CCO1]

100 mg (0.42 mmol) of the compound from Example 17A and 122 mg (0.42 mmol) of the compound from Example 2A were initially charged in 2 ml of acetonitrile, and 0.37 ml of N,N-diisopropylethylamine (2.12 mmol) was added. 0.30 ml of T3P (50% strength solution in ethyl acetate) (0.51 mmol) was then added dropwise, and the mixture was stirred at RT for 18 h. After concentration under reduced pressure, saturated aqueous sodium bicarbonate solution was added to the residue. After 10 min, the mixture was diluted with water and extracted twice with ethyl acetate. The combined organic phases were dried over sodium sulphate, filtered and concentrated. The crude product was purified by preparative HPLC [Method 9]. This gave 134 mg (73% of theory) of the title compound.

LC-MS [Method 1]: $R_t$=0.64 min; MS (ESIpos): m/z=435 (M+H)$^+$ $^1$H-NMR (400 MHz, DMSO-d$_6$): δ [ppm]=1.18 (s, 6H), 1.39-1.61 (m, 2H), 1.83 (br. s., 2H), 2.63-2.73 (m, 1H), 2.77 (s, 4H), 2.82-3.09 (m, 2H), 3.36-3.45 (m, 3H), 3.52 (t, 2H), 3.67-3.75 (m, 4H), 6.85 (d, 1H), 7.00-7.11 (m, 4H), 7.60 (dd, 1H), 8.18 (d, 1H).

Example 14

[4-(3,4-Dihydroisoquinolin-2(1H)-yl)piperidin-1-yl] {6-[2-(trifluoromethyl)morpholin-4-yl]pyridin-3-yl}methanone

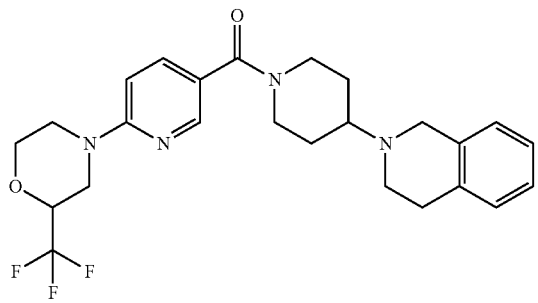 [SMILES: O=C(c1ccc(N2CCOC(C(F)(F)F)C2)nc1)N1CCC(N2CCc3ccccc3C2)CC1]

45 mg (0.16 mmol) of the compound from Example 20A and 47 mg (0.16 mmol) of the compound from Example 2A were initially charged in 2 ml of acetonitrile, and 0.14 ml of N,N-diisopropylethylamine (0.82 mmol) was added. 0.12 ml of T3P (50% strength solution in ethyl acetate) (0.20 mmol) was then added dropwise, and the mixture was stirred at RT for 18 h. After concentration under reduced pressure, saturated aqueous sodium bicarbonate solution was added to the residue. After 10 min, the mixture was diluted with water and extracted twice with ethyl acetate. The combined organic phases were dried over sodium sulphate, filtered and concentrated. Purification of the crude product was carried out by preparative HPLC [Method 9]. This gave 42 mg (54% of theory) of the target product.

LC-MS [Method 1]: $R_t$=0.78 min; MS (ESIpos): m/z=475 (M+H)$^+$ $^1$H-NMR (400 MHz, DMSO-d$_6$): δ [ppm]=1.36-1.61 (m, 2H), 1.74-1.97 (m, 2H), 2.63-2.72 (m, 1H), 2.77 (s, 4H), 2.85-3.11 (m, 4H), 3.70 (s, 3H), 4.01-4.16 (m, 3H), 4.23-4.38 (m, 1H), 4.42-4.54 (m, 1H), 6.98 (s, 1H), 7.01-7.12 (m, 4H), 7.54-7.73 (m, 1H), 8.25 (d, 1H).

Example 15

[4-(3,4-Dihydroisoquinolin-2(1H)-yl)piperidin-1-yl] [6-(2,2-dioxido-2-thia-6-azaspiro[3.3]hept-6-yl)pyridin-3-yl]methanone

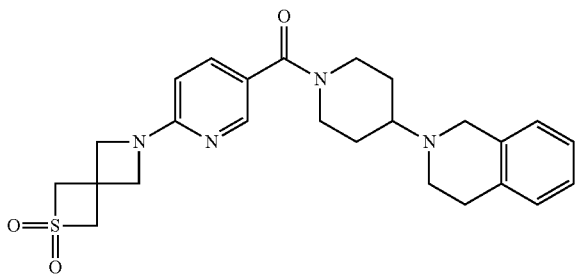 [SMILES: O=C(c1ccc(N2CC3(C2)CS(=O)(=O)C3)nc1)N1CCC(N2CCc3ccccc3C2)CC1]

138 mg (0.51 mmol) of the compound from Example 23A and 149 mg (0.51 mmol) of the compound from Example 2A were initially charged in 2 ml of acetonitrile, and 0.45 ml of N,N-diisopropylethylamine (2.57 mmol) was added. 0.37 ml of T3P (50% strength solution in ethyl acetate) (0.62 mmol) was then added dropwise, and the mixture was stirred at RT for 18 h. After concentration under reduced pressure, saturated aqueous sodium bicarbonate solution was added to the residue. After 10 min, the mixture was diluted with water and extracted twice with ethyl acetate. The combined organic phases were dried over sodium sulphate, filtered and concentrated. Purification of the crude product was carried out by preparative HPLC [Method 9]. This gave 140 mg (55% of theory) of the target product.

LC-MS [Method 1]: $R_t$=0.49 min; MS (ESIpos): m/z=467 (M+H)$^+$ $^1$H-NMR (400 MHz, DMSO-d$_6$): δ [ppm]=1.35-1.58 (m, 2H), 1.75-1.90 (m, 2H), 2.62-2.72 (m, 1H), 2.77 (s, 4H), 2.80-3.09 (m, 2H), 3.62-3.72 (m, 2H), 4.22 (s, 4H), 4.51 (s, 4H), 6.40-6.49 (m, 1H), 7.08 (s, 4H), 7.51-7.68 (m, 1H), 8.02-8.22 (m, 1H).

B) ASSESSMENT OF PHYSIOLOGICAL EFFICACY

The suitability of the compounds according to the invention for treating cardiovascular disorders can be demonstrated in the following assay systems:

B-1) In Vitro Assays

B-1a) Antagonism Against Adrenoreceptors

Antagonism against the adrenoreceptor $α_{1A}$ was tested using a recombinant human $α_{1A}$ receptor CHO cell line which additionally also recombinantly expresses mtAeq (mitochondrial aequorin). Antagonism against the adrenoreceptor $α_{2A}$ was tested using a recombinant human $α_{2A}$-Gα16 receptor fusion protein CHO cell line (PerkinElmer Life Sciences) which additionally also recombinantly expresses mtAeq. Antagonism against the adrenoreceptor $α_{2B}$ was tested using a recombinant human $α_{2B}$ receptor CHO cell line (PerkinElmer Life Sciences) which additionally also recombinantly expresses mtAeq. Antagonism against the adrenoreceptor $α_{2C}$ was tested using a recombinant human $α_{2C}$ receptor CHO cell line which additionally also recombinantly expresses a chimaric G protein (Gαqi3) and mtOb (mitochondrial obelin).

The cells were cultivated at 37° C. and 5% $CO_2$ in Dulbecco's modified Eagle's Medium/NUT mix F12 with L-glutamine which additionally contains 10% (v/v) inactivated foetal calf serum, 1 mM sodium pyruvate, 0.9 mM sodium bicarbonate, 50 U/ml penicillin, 50 μg/ml streptomycin, 2.5 μg/ml amphotericin B and 1 mg/ml Geneticin. The cells were passaged with enzyme-free Hank's-based cell dissociation buffer. All cell culture reagents used were from Invitrogen (Carlsbad, USA).

Luminescence measurements were carried out on white 384-well microtitre plates. 2000 cells/well were plated in a volume of 25 μl and cultivated for one day at 30° C. and 5% $CO_2$ in cell culture medium with coelenterazine ($\alpha_{2A}$ and $\alpha_{2B}$: 5 μg/ml; $\alpha_{1a/c}$ and $\alpha_{2C}$: 2.5 μg/ml). Serial dilutions of the test substances (10 μl) were added to the cells. After 5 minutes, noradrenaline was added to the cells (35 μl; final concentrations: 20 nM ($\alpha_{1a/c}$ and $\alpha_{2C}$) or 200 nM ($\alpha_{2A}$ and $\alpha_{2B}$)), and the emitted light was measured for 50 seconds using a CCD (charge-coupled device) camera (Hamamatsu Corporation, Shizuoka, Japan) in a light-tight box. The test substances were tested up to a maximum concentration of 10 The $IC_{50}$ values were calculated from the appropriate dose-response curves. The results for the antagonism against the adrenoreceptor $\alpha_{2C}$ are shown in Table 1:

TABLE 1

| Example No. | $IC_{50}$ [nM] | Example No. | $IC_{50}$ [nM] | Example No. | $IC_{50}$ [nM] |
|---|---|---|---|---|---|
| 1 | 22 | 2 | 13 | 3 | 9 |
| 4 | 24 | 5 | 65 | 6 | 27 |
| 7 | 21 | 8 | 58 | 9 | 11 |
| 10 | 11 | 11 | 11 | 12 | 21 |
| 13 | 53 | 14 | 23 | 15 | 53 |

B-1b) Binding Studies on Human α1- and α2-Adrenergic Receptors

To prepare cell membranes with human $\alpha_1$- and $\alpha_2$-adrenergic receptors, CHO cells stably overexpressing $\alpha_1$- and $\alpha_2$-adrenergic receptors are lysed and then subjected to differential centrifugation. After lysis in binding buffer (50 mM tris(hydroxymethyl)aminomethane/1 N hydrochloric acid, 5 mM magnesium chloride, pH 7.4) using an Ultra Turrax (Jahnke&Kunkel, Ika-Werk), the homogenate is centrifuged at 1000 g and at 4° C. for 10 min. The resulting sediment is discarded and the supernatant is centrifuged at 20000 g and at 4° C. for 30 min. The supernatant is discarded and the sediment is resuspended in binding buffer and stored at −70° C. until the binding test. For the binding test the radioligands $^3$H-MK-912 (2.2-3.2 TBq/mmol, PerkinElmer) (0.4 nM for $\alpha_{2C}$-adrRez and 1 nM for $\alpha_{2A}$-adrRez), 0.25 nM $^3$H-prazosin ($\alpha_{1AC}$-adrRez; 2.6-3.3 TBq/mmol, PerkinElmer), 0.25 nM $^3$H-rauwolscine ($\alpha_{2B}$-adrRez, 2.6-3.2 TBq/mmol, PerkinElmer) are incubated for 60 minutes with 5-20 μg cell membranes in binding buffer (total test volume 0.2 ml) in the presence of the test substances at 30° C. in 96-well filter plates (FC/B glass fibre, Multiscreen Millipore). The incubating is terminated by aspiration of the unbound radioactivity and the plates are then washed with binding buffer and subsequently dried at 40° C. for 1 hour. Liquid scintillator (Ultima Gold, PerkinElmer) is then added and the radioactivity that remained on the plates is measured in a liquid scintillation counter (Microbeta, Wallac). Non-specific binding is defined as radioactivity in the presence of 1-10 μM WB-4101 ($\alpha_{2C}$-adrRez and $\alpha_{2A}$-adrRez), prazosin ($\alpha_{2B}$-adrRez and $\alpha_{1AC}$-adrRez) (all from Sigma) and is generally <25% of the bound total radioactivity. The binding data ($IC_{50}$ and dissociation constant K) are determined using the program GraphPad Prism Version 4.0.

B-2) In Vivo Assays

B-2a) Relaxation Measurement on Isolated Rat Tail Arteries

Male Wistar rats (200-250 g) were euthanized with carbon dioxide. The tail artery is prepared and incubated in Krebs-Henseleit buffer at 4° C. for 17 h (composition in mmol/l: NaCl 112, KCl 5.9, $CaCl_2$ 2.0 $MgCl_2$ 1.2, $NaH_2PO_4$ 1.2, $NaHCO_3$ 25, glucose 11.5). The artery is cut into rings of length 2 mm, transferred to an organ bath filled with 5 ml of Krebs-Henseleit buffer and connected to a wire myograph (DMT, Denmark). The buffer is warmed to 27° C. and sparged with 95% $O_2$, 5% $CO_2$. Before each experiment, the responsiveness of the preparation is tested by adding potassium-containing Krebs-Henseleit solution (50 mmol/l KCl). After an equilibration phase of 60 minutes, contraction of the vessel rings is induced with 30 nmol/l UK 14.304. The test substance is then added cumulatively in increasing concentration. Relaxation is shown as a reduction in the contraction induced by UK 14.304.

B-2b) Haemodynamics CHF Rat

Male old Wistar, ZDF/Crl-Lepr fa/fa, SHR-SP or Sprague Dawley rats (Charles River; 250-300 g) are anaesthetized with 5% isoflurane in an anaesthesis cage, intubated and then ventilated artificially (rate: 60 breaths/min; ratio inspiration to expiration: 50:50; positive end-expiratory pressure: 1 cm H2O; tidal volume: 10 ml/kg of body weight; $FIO_2$: 0.5; 2% isoflurane). The body temperature is maintained at 37-38° C. by a heating mat. 0.05 mg/kg Temgesic is given subcutaneously as analgesic. For the haemodynamic measurement, the rats are tracheotomized and ventilated artificially (rate: 60 breaths/min; ratio inspiration to expiration: 50:50; positive end-expiratory pressure: 1 cm $H_2O$; tidal volume: 10 ml/kg of body weight; $FIO_2$: 0.5). Anaesthesia is maintained by inhalative isofluran anaesthesia. The left-ventricular pressure is determined via the left carotid artery using a Millar microtip catheter (Millar SPR-320 2F). Systolic left-ventricular pressure (sLVP), end-diastolic ventricular pressure (LVEDP), contractility (+dPdt) and relaxation force (−dPdt) are determined as derived parameters. Following the haemodynamic measurements, the heart is removed and the ratio of right to left ventricle including septum is determined. Furthermore, plasma samples are obtained to determine plasma biomarkers and plasma substance concentrations.

B-2c) Measurement of Blood Flow and Blood Pressure in Rats

Wistar rats (Hsd Cpb:Wu) of a weight of 250-350 g or ZDF rats (ZDF/Crl-Lepr fa/fa) of a weight of 330-520 g are anesthetized using 2.5% isoflurane in an oxygen/laughing gas mixture (40:60). To determine the blood flow in the carotid artery and the femoral artery, the anesthetized rat is brought into a supine position, and the left carotid artery and the right femoral artery are then carefully exposed. Blood flow is measured by placing flow probes (Transonic Flowprobe) at the vessels. By introducing a PESO artery catheter into the left femoral artery, blood pressure and heart rate are determined (Transducer Ref. 5203660: from Braun CH). The substances are administered as a bole injection or a continuous infusion via a venous catheter in the left femoral vein.

Following the preparation of the animals, there is a 5 min baseline interval. Infusion of the AR alpha2C antagonist is then started. In the steady state (32 min after the start of the experiment), the femoral flow is determined in relation (% difference) to the initial flow.

B-2d) Assay of Perfusion-Enhancing Substances (Haemodynamics)

To reduce perfusion, the right external iliac artery in anesthetized (for example anesthesia by inhalating isoflurane, enflurane) rats (for example ZDF/Crl-Lepr fa/fa) is ligated under sterile conditions. Depending on the degree of collateralization of the animals, it may additionally be necessary to ligate the femoral artery to reduce perfusion. After the operation or else preventatively, the test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day over a period of up to 50 weeks, or administration is continuous via subcutaneously implanted osmotic mini-pumps (for example Alzet pumps). During the experiment, microperfusion and temperature of the lower extremities are documented. Here, under anesthesia, a temperature-sensitive laser doppler probe (Periflux) is fastened with adhesive to the paws of the rats, allowing the measurement of microperfusion and skin temperature. Depending on the test protocol, samples such as blood (interim diagnostics) and other bodily fluids, urine or organs are removed to carry out further in vitro examinations, or, to document haemodynamics, blood pressure and heart rate are measured via a catheter in the carotid artery. At the end of the experiment, the animals are painlessly sacrificed.

B-2e) Assay of Perfusion-Enhancing Substances (Microcirculation)

In diabetic (ZDFfa/fa) and healthy rats (Wistar), a laser doppler probe was fastened under anaesthesia conditions (isoflurane anaesthesia) at the sole of the paw for measuring cutaneous microcirculation. The test animals were once treated orally with the test substances. During the experiment, microperfusion and temperature of the lower extremities were documented continuously. Here, a temperature-sensitive laser doppler probe (Periflux, O2C) was fastened with adhesive to the paws of the animals, allowing the measurement of microperfusion and skin temperature. The microcirculation measurement values were measured on both paws 30 min after oral administration of the test substance. From these data, means were calculated and compared to those of placebo-treated animals. What is shown are the minimum effective doses (MED) where the test substances showed a significantly improved microcirculation compared with placebo and the factor by which microcirculation is improved at this dose compared to placebo. Also stated is the MED for the significant increase of skin temperature (ttest).

Microcirculation data for adrenoreceptor α2c antagonist of Example 8 and for the comparative substance ORM12741, an AR α2c antagonist from Orion, are shown in Table 2:

TABLE 2

| Example No. | MED [mg/kg] microcirculation | MED [mg/kg] skin temperature |
| --- | --- | --- |
| 1 | 1 (1.8×) | 1 |
| 4 | 0.1 (2.4×) | 0.1 |
| 6 | no effect (max 1.3×) | no effect |
| 10 | 0.03 (2.1×) | 0.03 |
| ORM-12741 (Orion) | 0.1 (1.9×) | 0.01 |

B-2f) Assay of Perfusion-Enhancing Substances (Motoric Function) in the Treadmill Test To determine the motor function, the running behaviour of mice (for example eNOS knock out mice, wild-type mice C-57 B16 or ApoE knock out mice) is examined on treadmills. To get the mice used to using the treadmill voluntarily, 4-5 weeks before the start of the experiment the animals are put singly into cages with the treadmill and trained. 2 weeks before the start of the experiment, the movements of the mice on the treadmill are recorded by a computer-linked photo cell, and various running parameters such as, for example, daily distance run, individual distances covered, but also their temporal distribution over the day are determined According to their natural running behaviour, the animals are randomized into groups (8-12 animals) (control group, sham group and one or more substance groups). After the customization phase of 2 weeks, to reduce perfusion in the hind legs the femoral arteries on both sides are ligated under anaesthesia and under sterile conditions (for example anaesthesia by inhaling isoflurane). After the operation or else preventatively, the test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day over a period of up to 5 weeks, or administration is continuous via subcutaneously implanted osmotic mini-pumps. The running behaviour of the animals is monitored and recorded over a period of several weeks after the operation. At the end of the experiment, the animals are painlessly sacrificed. Depending on the test protocol, samples such as blood and other bodily fluids or organs are removed to carry out further in vitro examinations (S. Vogelsberger Neue Tiermodelle für die Indikation Claudicatio Intermittens [Novel animal models for the indication intermittent claudication] (pocket book), publisher: VVB Laufersweiler Verlag (March 2006), ISBN-10: 383595007X, ISBN-13: 978-3835950078).

B-2g) Assay of Perfusion-Enhancing Substances (Measurement of the Occlusion Pressure)

To reduce perfusion, the right external iliac artery in anaesthetized (for example anaesthesia by inhaling isoflurane) rats (for example ZDF rats) is ligated under sterile conditions. Depending on the degree of collateralization of the animals, it may additionally be necessary to ligate the femoral artery to reduce perfusion. After the operation or else preventatively, the test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day over a period of up to 5 weeks, or administration is continuous via subcutaneously implanted osmotic mini-pumps (for example Alzet pumps). The occlusion pressures of the animals are measured before the operation (subsequent randomization) and once every week over a period of up to 2 months after the operation. Here, under anaesthesia an inflatable cuff is placed around the hind legs of the rats, and a temperature-adjustable laser doppler probe (Periflux) is fastened with adhesive on the paws. The cuffs are inflated until the laser doppler probes do no longer measure any blood flow. The pressure in the cuffs is then continuously reduced and the pressure at which blood flow is detected again is determined. Depending on the test protocol, samples such as blood (interim diagnostics) and other bodily fluids or organs are removed for further in vitro examinations. At the end of the experiment, the animals are sacrificed painlessly (S. Vogelsberger Neue Tiermodelle fin die Indikation Claudicatio Intermittens [New Animal Models for the Indication Intermittent Claudication] (pocket book), publisher: VVB Laufersweiler Verlag (March 2006), ISBN-10: 383595007X, ISBN-13: 978-3835950078.)

B-2h) Examination of Substances Affecting Wound Healing (Ulcer Model)

To induce a superficial wound, diabetic mice (db/db, i.e. BKS.Cg-m Dock7m+/+Leprdb/J mice) were anaesthetized with isoflurane. A continuous lesion (10 mm×10 mm) was placed on the left side of a skin area where the hairs had been removed and which had been disinfected. The animals were then randomized to the different treatment groups. In all groups, the wounds were covered with dressings (Systagenix Wound Management, UK). Daily (from day 1 after wound placing) the animals were treated by gavage (200 vehicle=10% EtOH+30% PEG400+60% water for injection) with the substances at the stated dosages. On days 4, 8, 12, 16 and 20, the animals were anaesthetized, the dressings were removed and the wound size was measured using digital photos. The photos were evaluated by an automatic calibrated planimetric process.

The results for the compound of Example 4 are shown in FIG. 1 as remaining wound sizes over the course of the experiment. To this end, all individual values were referenced in percent to the individual animal at the day the wound was placed. What is shown are means+/−SEM.

B-2i) Examination of Substances Affecting Kidney Function

In animals suffering from acute or disease-related kidney damage (e.g. STZ rat, ZDF rat, ZDF rat with DOCA implantat, UUO kidney damage model, glomerulonephritis model, diabetes, atherosclerosis), diuresis is carried out at regular intervals before or during continuous treatment with the test substances. The test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day, or administration is continuous via subcutaneously implanted osmotic mini-pumps (for example Alzet pumps). Over the entire duration of the test, plasma and urine parameters are determined.

B-2j) Haemodynamics in the Anesthetized Dog

Healthy Mongrel® dogs (Marshall BioResources, Marshall Farms Inc; Clyde N.Y.; USA) or Mongrel® dogs suffering from heart failure of both sexes and having a weight of 25-35 kg are used. Anesthesia is initiated by slow i.v. administration of 25 mg/kg sodium thiopental (Trapanal) and 0.15 mg/kg alcuronium chloride (Alloferin®) and maintained during the experiment by means of a continuous infusion of 0.04 mg/kg*h fentanyl (Fentanyl®), 0.25 mg/kg*h droperidol (Dihydrobenzperidol) and 15 μg/kg/h alcuronium chloride (Alloferin®). After intubation, the animals are ventilated by the ventilator at a constant respiratory volume such that an end-tidal $CO_2$ concentration of about 5% is achieved. Ventilation is performed with room air, enriched with about 30% oxygen (normoxia). To measure the haemodynamic parameters, a liquid-filled catheter is implanted into the femoral artery for measuring blood pressure. A Swan-Ganz® catheter having two lumens is introduced in a flow-directed manner via the jugular vein into the pulmonary artery (distal lumen for measuring the pressure in the pulmonary artery, proximal lumen for measuring the central vein pressure). Using a temperature sensor at the tip of the catheter, the continuous cardiac output (CCO) is determined. Blood flow is measured at various vascular beds such as the coronary artery, the carotid artery or the femoral artery by placing flow probes (Transonic Flowprobe) at the vessels in question. The pressure in the left ventricle is measured after introduction of a microtip catheter (Millar® Instruments) via the carotid artery into the left ventricle, and the dP/dt ratio as a measure of contractility is derived therefrom. Substances are administered i.v. via the femoral vein or intraduodenally as cumulative dose/activity curve (bole or continuous infusion). The haemodynamic signals are recorded and evaluated by means of pressure transducers/amplifiers and PONEMAH® as data aquisition software.

To induce heart failure, a pacemaker is implanted into the dogs under sterile conditions. After induction of anesthesia with pentobarbital-Na (15 to 30 mg kg-1 i.v.) followed by intubation and subsequent ventilation (room air; Sulla 808, Dräger®, Germany), anesthesia is maintained by continuous infusion of pentobarbital (1-5 mg kg-1 h-1) and fentanyl (10-40 μg $kg^{-1}$ $h^{-1}$). A pacemaker cable (Setrox S60®, Biotronik, Germany) is implanted via an incision of the left jugular vein and placed in the right ventricle. The cable is connected to the pacemaker (Logos®, Biotronik, Germany), which is positioned in a small subcutaneous pocket between the shoulder blades. Ventricular pacing is started only 7 days after the surgical intervention, to obtain heart failure at a frequency of 220 beats/min over a period of 10-28 days.

B-2k) Determination of the Antidepressive Effect in the Rat-Forced-Swimming-Test Rats which are forced to swim in a narrow room from which there is no escape adapt after an initial phase of increased activity by adopting a characteristic rigid posture and only carry out those movements which are absolutely required to keep the head over the water. This immobility can be reduced by a number of clinically active antidepressants (e.g. Cryan J F, Markou A, Lucki I. Assessing antidepressant activity in rodents: recent developments and future needs. Trends Pharmacol. Sci. 2002; 23:238-245). The method used here is based on the protocol of Porsolt et al. (Porsolt R D, Anton G, Blavet N, Jalfre M. Behavioural despair in rats: a new model sensitive to antidepressant treatments. Eur. J. Pharmacol. 1978; 47:379-91; and Porsolt R D, Brossard G, Hautbois C, Roux S. Rodent models of depression: forced swimming and tail suspension behavioral despair tests in rats and mice. Curr. Protoc. Neurosci. 2001; Chapter 8:Unit 8.10A, 1-10) and De Vry et al. (De Vry J, Maurel S, Schreiber R, de Beun R, Jentzsch K R. Comparison of hypericum extracts with imipramine and fluoxetine in animal models of depression and alcoholism. Eur. Neuropsychopharmacology 1999; 9:461-468). In two sessions (training and test) at an interval of 24 h, the rats are forced to swim in a narrow cylinder filled with water from which there is no escape. The training session (duration 15 min) is carried out before the treatment with substance without recording the behaviour in order to familiarize the rats with the 5-minute test session 24 h later. During both sessions, the rats are individually placed into the cylinders filled with water, which are optically separated from one another. After the session, the rats are removed from the water and dried. About 24, 5 and 1 h prior to the test session, the rats are treated with test substance or vehicle solution; the first administration takes place immediately after the training session. 3 substance administrations prior to the test session lead to more stable pharmacological results than a single administration. The test sessions are recorded electronically using a surveillance video camera and, after storage, analyzed off-line using a computer. For each animal, the behaviour is analyzed by 3-4 independent observers who score the total time of immobility in seconds over the 5-minute test session.

Passive behaviour or immobility is defined as a rat which drifts in the water in an upright position and makes only small movements to keep the head over the water or to maintain its body in a balanced stable position. In contrast, active behaviour is characterized by active swimming movements, e.g. forceful movements of front or hind legs and/or tail, climbing or diving.

For each animal and treatment group, the mean of the duration of immobility determined by the observers is calculated. Differences in the duration of immobility between the groups are examined statistically by ANOVA or a suitable non-parametric test with p<0.05 as significance level.

B-2l) Radiotelemetric Measurement of Blood Pressure and Heart Rate of Conscious Rats A commercially available telemetry system from Data Sciences International DSI, USA, was employed for the measurements on conscious rats described below. The system consists of 3 main components: (1) implantable transmitters (Physiotel® telemetry transmitter), (2) receivers (Physiotel® receiver), which are linked via a multiplexer (DSI Data Exchange Matrix) to a (3) data acquisition computer. The telemetry system makes it possible to continuously record blood pressure, heart rate and body motion of conscious animals in their usual habitat.

The studies were conducted on adult female Wistar rats with a body weight of >200 g. After transmitter implantation, the experimental animals were housed singly in type III Makrolon® cages. They had free access to standard feed and water. The day/night rhythm in the test laboratory was set by changing the illumination of the room.

Transmitter Implantation:

The telemetry transmitters used (PA-C40, DSI) were surgically implanted under aseptic conditions in the experimental animals at least 14 days before the first experimental use.

For the implantation, the fasted animals were anaesthetized with isoflurane (IsoFlo®, Abbott, initiation 5%, maintenance 2%) and shaved and disinfected over a large area of their abdomens. After the abdominal cavity had been opened along the linea alba, the liquid-filled measuring catheter of the system was inserted into the descending aorta in the cranial direction above the bifurcation and fixed with tissue glue (VetBond™, 3M). The transmitter housing was fixed intraperitoneally to the abdominal wall muscle, and the wound is closed layer by layer. Post-operatively, an antibiotic (Ursocyclin® 10%, 60 mg/kg s.c., 0.06 ml/100 g body weight, Serumwerk Bernburg AG, Germany) for infection prophylaxis and an analgesic (Rimadyl®, 4 mg/kg s.c., Pfizer, Germany) were administered.

Substances and Solutions:

Unless stated otherwise, the substances to be studied were administered orally to a group of animals in each case (n=6). In accordance with an administration volume of 2 ml/kg of body weight, the test substances were dissolved in suitable solvent mixtures. A solvent-treated group of animals (placebo/vehicle=diethylene glycol monoethyl ether, Transcutol, 2 ml/kg p.o.) was used as control.

Test Procedure:

The telemetry measuring system is configured for 24 animals.

Each of the instrumented rats living in the system was assigned a separate receiving antenna (RPC-1 Receiver, DSI). The implanted transmitters were activated externally via an installed magnetic switch and were switched to transmission during the pre-run of the experiment. The signals emitted were detected online by a data acquisition system (Dataquest™ A.R.T. for Windows, DSI) and processed accordingly.

In the standard procedure, the following were measured for 10-second periods in each case: (1) systolic blood pressure (SBP), (2) diastolic blood pressure (DBP), (3) mean arterial pressure (MAP) and (4) heart rate (HR) and (5) activity (ACT). These parameters were measured over 24 hours after administration.

The acquisition of measurements was repeated under computer control at 5-minute intervals. The source data obtained as absolute values were corrected in the diagram with the currently measured barometric pressure (Ambient Pressure Reference Monitor, APR-1, DSI).

Evaluation:

After the end of the experiment, the acquired individual data were sorted using the analysis software (Dataquest™ A.R.T. 4.1 Analysis). The blank value was taken to be the mean of the pre-run (i.e. before substance administration) (4 absolute values) and this was compared to the absolute value of the measurement, giving the deviation in %. The data were smoothed over a presettable period by determination of the means (15 minute mean).

LITERATURE

K. Witte, K. Hu, J. Swiatek, C. Müssig, G. Ertl and B. Lemmer, Experimental heart failure in rats: effects on cardiovascular circadian rhythms and on myocardial β-adrenergic signaling, Cardiovasc. Res. 47 (2): 203-405, 2000.

Results:

The results are shown in FIGS. 2 to 5 for the compound of Example 4 in comparison to an adrenoreceptor $\alpha_{2C}$ receptor antagonist from Orion (ORM-12741) which has been tested for the therapy of Alzheimer's disease and Raynaud's syndrome.

Example No. 4 showed no haemodynamic effects (blood pressure, heart rate). At an oral dose of 3 and 10 mg/kg a slight transient increase in the heart rate was observed. In contrast, the comparative substance ORM-12741, an AR α2c receptor antagonist from Orion, showed an additional reduction in blood pressure at 10 mg/kg.

C) WORKING EXAMPLES OF PHARMACEUTICAL COMPOSITIONS

The substances according to the invention can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg Diameter 8 mm, radius of curvature 12 mm

Production:

The mixture of the compound of Example 1, lactose and starch is granulated with a 5% strength solution (m/m) of the PVP in water. After drying, the granules are mixed with the magnesium stearate for 5 min. This mixture is compressed in a conventional tablet press (see above for format of the tablet).

Oral Suspension:
Composition:
1000 mg of the compound of Example 1, 1000 mg of ethanol (96%), 400 mg of Rhodigel (xanthan gum) (from FMC, USA) and 99 g of water.
10 ml of oral suspension correspond to a single dose of 100 mg of the compound according to the invention.
Production:
The Rhodigel is suspended in ethanol, and the compound of Example 1 is added to the suspension. The water is added while stirring. The mixture is stirred for approx. 6 h until the Rhodigel has finished swelling.
Intravenously Administrable Solution:
Composition:
1 mg of the compound of Example 1, 15 g of polyethylene glycol 400 and 250 g of water for injection purposes.
Production:
The compound of Example 1 is dissolved together with polyethylene glycol 400 by stirring in the water. The solution is sterilized by filtration (pore diameter 0.22 μm) and dispensed under aseptic conditions into heat-sterilized infusion bottles. The latter are closed with infusion stoppers and crimped caps.

The invention claimed is:
1. A compound of the formula (I)

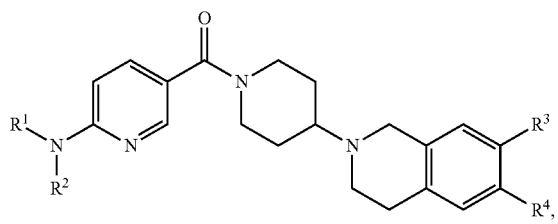

(I)

in which
$R^1$ represents $C_1$-$C_6$-alkyl or $C_3$-$C_5$-cycloalkyl,
where alkyl is substituted by 1 to 2 substituents independently of one another selected from the group consisting of hydroxy, $C_1$-$C_4$-alkoxy and haloalkoxy
and
$R^2$ represents hydrogen or $C_1$-$C_4$-alkyl,
or
$R^1$ and $R^2$ together with the nitrogen atom to which they are attached form a 4- to 7-membered N-heterocycle,
where the N-heterocycle may be substituted by 1 to 3 substituents independently of one another selected from the group consisting of oxo, hydroxy, monofluoromethyl, difluoromethyl, trifluoromethyl, hydroxycarbonyl, tert-butoxycarbonyl, aminocarbonyl, $C_1$-$C_4$-alkyl, $C_1$-$C_4$-alkoxy, $C_1$-$C_4$-alkoxy-$C_1$-$C_4$-alkyl, halogen and hydroxyalkyl,
or
where the N-heterocycle may have two substituents which, together with the carbon atom of the N-heterocycle to which they are jointly attached, form a 4- to 6-membered heterocycle,
where this heterocycle for its part may be substituted by 1 to 3 substituents independently of one another selected from the group consisting of oxo, methyl and ethyl,
$R^3$ represents hydrogen, fluorine, methoxy or ethoxy
and
$R^4$ represents hydrogen, fluorine, methoxy or ethoxy,
and the salts thereof.

2. The compound of the formula (I) according to claim 1 in which
$R^1$ represents $C_1$-$C_6$-alkyl,
where alkyl is substituted by 1 to 2 substituents independently of one another selected from the group consisting of hydroxy and $C_1$-$C_4$-alkoxy
and
$R^2$ represents hydrogen or $C_1$-$C_4$-alkyl,
or
$R^1$ and $R^2$ together with the nitrogen atom to which they are attached form a 4- to 7-membered N-heterocycle,
where the N-heterocycle may be substituted by 1 to 3 substituents independently of one another selected from the group consisting of oxo, hydroxy, monofluoromethyl, difluoromethyl, trifluoromethyl, hydroxycarbonyl, tert-butoxycarbonyl, aminocarbonyl, $C_1$-$C_4$-alkyl, $C_1$-$C_4$-alkoxy and halogen,
or
where the N-heterocycle may have two substituents which, together with the carbon atom of the N-heterocycle to which they are jointly attached, form a 4- to 6-membered heterocycle,
where this heterocycle for its part may be substituted by 1 to 3 substituents independently of one another selected from the group consisting of oxo, methyl and ethyl,
$R^3$ represents hydrogen, fluorine, methoxy or ethoxy,
and
$R^4$ represents hydrogen, fluorine, methoxy or ethoxy,
and the salts thereof.

3. The compound of the formula (I) according to claim 1 in which
$R^1$ represents $C_2$-$C_6$-alkyl,
where alkyl is substituted by a substituent selected from the group consisting of hydroxy, methoxy and ethoxy,
and
$R^2$ represents hydrogen,
or
$R^1$ and $R^2$ together with the nitrogen atom to which they are attached form an azetidine, pyrrolidine, piperidine, azepane, piperazine, morpholine, thiomorpholine, 1-oxidothiomorpholine or 1,1-dioxidothiomorpholine,
where azetidine, pyrrolidine, piperidine, azepane, piperazine, morpholine, thiomorpholine, 1-oxidothiomorpholine and 1,1-dioxidothiomorpholine may be substituted by 1 to 2 substituents independently of one another selected from the group consisting of hydroxy, hydroxycarbonyl, $C_1$-$C_3$-alkyl, trifluoromethyl, methoxy and methoxymethyl,
or
where azetidine, pyrrolidine, piperidine, azepane, piperazine and morpholine may have two substituents which, together with the carbon atom of the azetidine, pyrrolidine, piperidine, azepane, piperazine or morpholine to which they are jointly attached, form an azetidine, oxetane or 1,1-dioxidothietane,
where this azetidine, oxetane or 1,1-dioxidothietane for its part may be substituted by 1 to 2 substituents independently of one another selected from the group consisting of methyl and ethyl,
$R^3$ represents hydrogen
and
$R^4$ represents hydrogen, fluorine or methoxy,
or
$R^3$ represents hydrogen, fluorine or methoxy
and
$R^4$ represents hydrogen,
and the salts thereof.

4. The compound of the formula (I) according to claim 1 in which $R^1$ represents $C_2$-$C_4$-alkyl,
where alkyl is substituted by a substituent selected from the group consisting of hydroxy and methoxy, and $R^2$ represents hydrogen, or $R^1$ and $R^2$ together with the nitrogen atom to which they are attached form an azetidine, pyrrolidine, morpholine or 1,1-dioxidothiomorpholine,
where azetidine, pyrrolidine, morpholine or 1,1-dioxidothiomorpholine may be substituted by 1 to 2 substituents selected independently from the group consisting of hydroxycarbonyl, methyl, trifluoromethyl, methoxy and methoxymethyl or $R^1$ and $R^2$ together with the nitrogen atom to which they are attached form an azetidine,
where the azetidine may have two substituents which, together with the carbon atom of the azetidine to which they are jointly attached, form an oxetane or 1,1-dioxidothietane, $R^3$ represents hydrogen, fluorine or methoxy and $R^4$ represents hydrogen, or $R^3$ represents hydrogen, and $R^4$ represents hydrogen, fluorine or methoxy, and the salts thereof.

5. The compound of the formula (I) according to claim 1 in which $R^1$ represents $C_2$-$C_4$-alkyl,
where alkyl is substituted by a substituent selected from the group consisting of hydroxy and methoxy, and $R^2$ represents hydrogen, or $R^1$ and $R^2$ together with the nitrogen atom to which they are attached form an azetidine, pyrrolidine, morpholine or 1,1-dioxidothiomorpholine,
where azetidine, pyrrolidine, morpholine or 1,1-dioxidothiomorpholine may be substituted by 1 to 2 substituents selected independently from the group consisting of hydroxycarbonyl, methyl, trifluoromethyl, methoxy and methoxymethyl or $R^1$ and $R^2$ together with the nitrogen atom to which they are attached form an azetidine,
where the azetidine may have two substituents which, together with the carbon atom of the azetidine to which they are jointly attached, form an oxetane or 1,1-dioxidothietane, $R^3$ represents hydrogen or fluorine, and $R^4$ represents hydrogen, fluorine or methoxy, and the salts thereof.

6. A method of making the compound of the formula (I) of claim 1 or one of the salts thereof, wherein

[A] a compound of the formula (II)

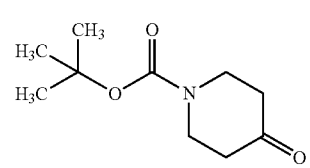

is reacted with a compound of the formula (III)

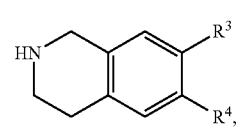

in which $R^3$ and $R^4$ have the meanings given in claim 1, in the presence of a reducing agent to give a compound of the formula (IV)

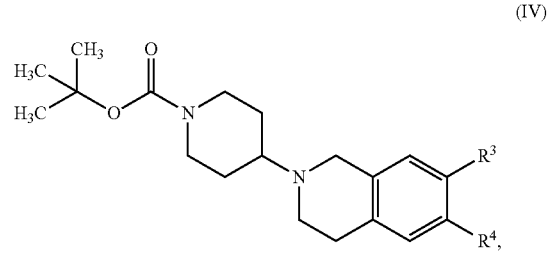

in which $R^3$ and $R^4$ have the meanings given in claim 1, or

[B] compound of the formula (IV)

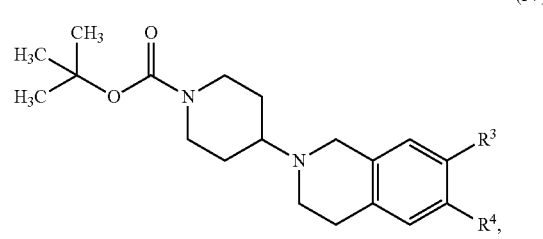

in which $R^3$ and $R^4$ have the meanings given in claim 1, is reacted in the presence of an acid to give a compound of the formula (V)

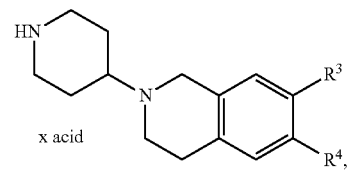

in which $R^3$ and $R^4$ have the meanings given in claim 1, or

[C] a compound of the formula (VI)

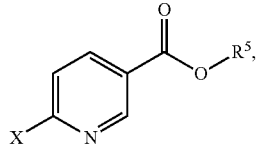
(VI)

in which

X represents halogen, preferably fluorine, chlorine or bromine, or sulphonylmethane and $R^5$ represents $C_1$-$C_4$-alkyl, preferably methyl or ethyl, is reacted in the presence of a base with a compound of the formula (VII)

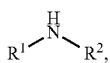
(VII)

in which $R^1$ and $R^2$ have the meaning given in claim 1, to give a compound of the formula (VIII)

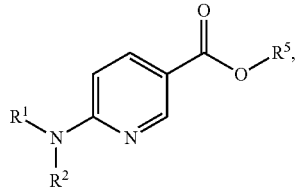
(VIII)

in which $R^1$ and $R^2$ have the meaning given in claim 1 and $R^5$ is as defined above, or

[D] a compound of the formula (IX)

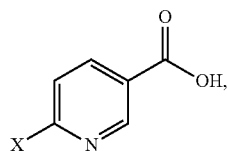
(IX)

in which

X represents halogen, preferably fluorine, chlorine or bromine, or sulphonylmethane, is reacted with a compound of the formula (VII)

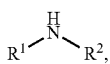
(VII)

in which $R^1$ and $R^2$ have the meaning given in claim 1, to give a compound of the formula (X)

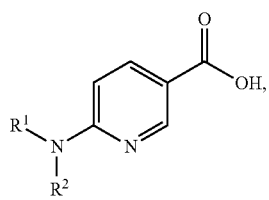
(X)

in which $R^1$ and $R^2$ have the meaning given in claim 1, or

[E] a compound of the formula (X)

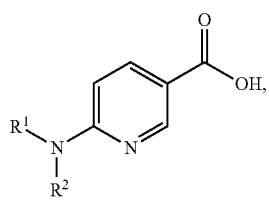
(X)

in which $R^1$ and $R^2$ have the meaning given in claim 1, is reacted with a compound of the formula (V)

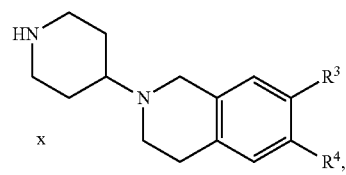
(V)

in which $R^3$ and $R^4$ have the meanings given in claim 1, in the presence of a dehydrating agent to give a compound of the formula (I)

or

[F] a compound of the formula (IX)

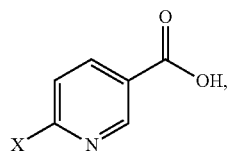
(IX)

in which

X represents halogen, preferably fluorine, chlorine or bromine, or sulphonylmethane, is reacted with compounds of the formula (V)

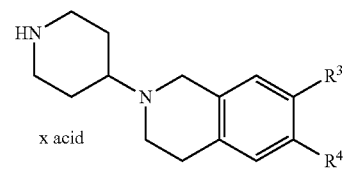
(V)

in which $R^3$ and $R^4$ have the meanings given in claim 1, in the presence of a dehydrating agent to give a compound of the formula (XI)

(XI)

in which
R$^3$ and R$^4$ have the meanings given in claim 1 and
X represents halogen, preferably fluorine, chlorine or bromine, or sulphonylmethane,
or
[G] a compound of the formula (XI)

(XI)

in which
R$^3$ and R$^4$ have the meanings given in claim 1 and
X represents halogen, preferably fluorine, chlorine or bromine, or sulphonylmethane,
is reacted with a compound of the formula (VII)

(VII)

in which R$^1$ and R$^2$ have the meaning given in claim 1,
to give the compound of the formula (I).

7. A compound of the formula (VIII) or (IX)

(VIII)

(IX)

in which
R$^1$ and R$^2$ together with the nitrogen atom to which they are attached form a 1,1-dioxidothiomorpholine or azetidine,
where the azetidine has two substituents which, together with the carbon atom of the azetidine to which they are jointly attached, form an oxetane,
and
R$^5$ represents C$_1$-C$_4$-alkyl, preferably methyl or ethyl, and the salts thereof.

8. A method of antagonizing an adrenoreceptor in an individual that suffers from diabetic ulcers on the extremities comprising administering an effective amount of the compound of claim 1.

9. A medicament comprising the compound of claim 1 in combination with one or more inert non-toxic pharmaceutically suitable auxiliaries.

10. A medicament comprising the compound of claim 1 in combination with one or more further active compounds selected from the group consisting of lipid metabolism-modulating active compounds, antidiabetics, hypotensive agents, agent which lower the sympathetic tone, perfusion-enhancing and/or antithrombotic agents and also antioxidants, aldosterone and mineralocorticoide receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressives and other psychopharmaceuticals.

11. A method of antagonizing an adrenoreceptor in an individual that suffers from at least one of primary and secondary forms of diabetic microangiopathies, diabetic wounds, diabetic ulcers on the extremities, diabetic foot ulcers, diabetic nephropathy, diabetic erectile dysfunction, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies comprising administering an effective amount of the medicament of claim 9.

12. A method of antagonizing an adrenoreceptor in an individual that suffers from at least one of primary and secondary forms of diabetic microangiopathies, diabetic wounds, diabetic ulcers on the extremities, diabetic foot ulcers, diabetic retinopathy, diabetic nephropathy, diabetic erectile dysfunction, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies in humans and animals comprising administering an effective amount of the compound of claim 1.

13. A method of antagonizing an adrenoreceptor in an individual that suffers from diabetic ulcers on the extremities comprising administering an effective amount of the medicament of claim 9.

14. A method of antagonizing an adrenoreceptor in an individual that suffers from diabetic disorders or diabetic diseases comprising administering an effective amount of the compound of claim 1.

15. A method of antagonizing an adrenoreceptor in an individual that suffers from diabetic disorders or diabetic diseases comprising administering an effective amount of the medicament of claim 9.

16. A medicament comprising the compound of claim 1 in combination with one or more further active compounds selected from the group consisting of rivaroxaban, iloprost, and inhibitors of phosphodiesterases (PDE) 1, 2, 3, 4, and/or 5.

17. A method of antagonizing an adrenoreceptor in an individual that suffers from peripheral occlusive disease comprising administering an effective amount of the compound of claim 1.

18. A method of antagonizing an adrenoreceptor in an individual that suffers from at least one of peripheral and cardiac vascular disorders, peripheral circulatory disturbances, or intermittent claudication comprising administering an effective amount of the compound of claim 1.

19. A method of antagonizing an adrenoreceptor in an individual that suffers from peripheral occlusive disease comprising administering an effective amount of the medicament of claim 9.

20. A method of antagonizing an adrenoreceptor in an individual that suffers from at least one of peripheral and cardiac vascular disorders, peripheral circulatory disturbances, or intermittent claudication comprising administering an effective amount of the medicament of claim 9.

* * * * *